US011407725B2

United States Patent
Bearrood et al.

(10) Patent No.: US 11,407,725 B2
(45) Date of Patent: Aug. 9, 2022

(54) SELECTIVE FLUORESCENT PROBE FOR ALDEHYDE DEHYDROGENASE

(71) Applicant: The Board of Trustees of the University of Illinois, Urbana, IL (US)

(72) Inventors: Thomas Edward Bearrood, Urbana, IL (US); Chelsea Diane Anorma, Urbana, IL (US); Jefferson Chan, Savoy, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 309 days.

(21) Appl. No.: 16/719,012

(22) Filed: Dec. 18, 2019

(65) Prior Publication Data

US 2020/0199092 A1  Jun. 25, 2020

Related U.S. Application Data

(60) Provisional application No. 62/783,570, filed on Dec. 21, 2018.

(51) Int. Cl.
| | | |
|---|---|---|
| *C07D 311/82* | (2006.01) | |
| *C07F 7/08* | (2006.01) | |
| *G01N 21/76* | (2006.01) | |
| *G01N 33/573* | (2006.01) | |

(52) U.S. Cl.
CPC .......... *C07D 311/82* (2013.01); *C07F 7/0816* (2013.01); *G01N 21/76* (2013.01); *G01N 33/573* (2013.01)

(58) Field of Classification Search
None
See application file for complete search history.

(56) References Cited

U.S. PATENT DOCUMENTS

2018/0024136 A1    1/2018   Chang et al.

FOREIGN PATENT DOCUMENTS

WO    2011019942 A2    2/2011

OTHER PUBLICATIONS

Anorma et al. ACS Central Science (Jul. 25, 2018) 4: 1045-1055 (Year: 2018).*
Registry file for compound 1136557-90-8, loaded Apr. 19, 2009 downloaded from STN on Dec. 17, 2021 (Year: 2009).*
Registry file for compound 1136807-14-1, loaded Apr. 19, 2009 downloaded from STN on Dec. 17, 2021 (Year: 2009).*
Registry file for compound 1186471-64-6, loaded Apr. 19, 2009 downloaded from STN on Dec. 17, 2021 (Year: 2009).*
Registry file for compound 1255762-18-6 loaded Dec. 7, 2010 downloaded from STN on Dec. 17, 2021 (Year: 2010).*
Mottram et al., "The Pennsylvania Green Fluorophore: A Hybrid of Oregon Green and Tokyo Green for the Construction of Hydrophobic and pH-Insensitive Molecular Probes," Org Lett., 8(4):581-584, Feb. 2006.

* cited by examiner

*Primary Examiner* — Susan M Hanley
(74) *Attorney, Agent, or Firm* — Haukaas Fortius PLLC; Michael H. Haukaas

(57) ABSTRACT

High aldehyde dehydrogenase 1A1 (ALDH1A1) activity has emerged as a reliable marker for the identification of both normal and cancer stem cells. Herein, is presented AlDeSense, a turn-on green fluorescent probe for aldehyde dehydrogenase 1A1 (ALDH1A1) and Ctrl-AlDeSense, a matching non-responsive reagent. AlDeSense exhibits a 20-fold fluorescent enhancement when treated with ALDH1A1. Through the application of surface marker antibody staining, tumorsphere assays, and assessment of tumorigenicity, the disclosed results show that cells exhibiting high AlDeSense signal intensity have properties of cancer stem cells. Herein, is also reported the development of a red congener, red-AlDeSense. Importantly, red-AlDeSense represents one of only a few examples of a turn-on sensor in the red region using the d-PeT quenching mechanism.

23 Claims, 35 Drawing Sheets

B.

E.

Oxidized AlDeSense

A.

B.

1st Representative image (with DAPI nuclear stain)

2nd Representative image (with additional DAPI nuclear stain)

3rd Representative image (without DAPI nuclear stain)

A.

B.

C.

D.

A.

B.

C.

D.

E.

F.

A.

B.

A.

B.

SELECTIVE FLUORESCENT PROBE FOR ALDEHYDE DEHYDROGENASE

RELATED APPLICATIONS

This application claims priority under 35 U.S.C. § 119(e) to U.S. Provisional Patent Application No. 62/783,570, filed Dec. 21, 2018, which is incorporated herein by reference.

GOVERNMENT SUPPORT

This invention was made with government support under Grant No. R35GM133581 awarded by the National Institutes of Health. The government has certain rights in the invention.

BACKGROUND OF THE INVENTION

Cancer stem cells (CSCs) were first discovered in human acute myelogenous leukemia, and have since been identified in breast cancer, glioblastoma, multiple myeloma, gastric cancer, pancreatic cancer, and colon cancer, among others. CSCs have an increased capacity to activate anti-apoptotic and pro-survival pathways, as well as to overexpress ATP-binding cassette transporters which act as potent efflux pumps to extrude small molecules (e.g., chemotherapeutics) from the cancer cells. As such, conventional chemotherapeutics can inadvertently lead to an enrichment of CSCs by killing non-CSCs, which in turn contributes to the emergence of highly aggressive and treatment-resistant phenotypes during relapse.

Unfortunately, the behavior of CSCs, especially in an in vivo context, is insufficiently understood despite the availability of cell cultures and 3D models. A major drawback of these systems is that they cannot mimic the complex microenvironment where CSCs are thought to reside. Moreover, CSCs are rare and represent only a small fraction of cells within a tumor. CSCs also exist in a dynamic equilibrium between undifferentiated and differentiated states, which is modulated by specific properties of the tumor microenvironment (e.g., hypoxia), as well as interactions with a network of cells, signaling molecules, and the extracellular matrix. Thus, methods that can be employed to not only detect CSCs but also to report on specific in vivo properties such as stem cell plasticity are highly desirable.

One approach to image CSCs is to target CSC surface biomarkers with a reporter (e.g., optical dye) conjugated to an antibody. However, this can lead to off-target binding and uneven or incomplete staining because antibody-dye conjugates cannot readily permeate into tumor regions distal from blood vasculature. Alternatively, genetically engineered CSCs expressing fluorescent proteins (e.g., GFP) or luciferase bioluminescent constructs can facilitate lineage tracing experiments. Major limitations are that it can only be used to visualize CSCs that have been previously isolated, transfected, and reintroduced into an animal model, but not all cell types are amenable to genetic manipulation.

In contrast, aldehyde dehydrogenases (ALDHs), in particular the 1A1 isoform, is believed to be a universal marker of CSCs across many cancer types, including prostate, lung, breast, esophageal, and ovarian cancers. In these instances, ALDH1A1 is associated with treatment resistance and poor clinical outcome. In addition to ALDH1A1, there are 18 other ALDH isoforms in humans, many of which display promiscuous and overlapping substrate scopes with ALDH1A1 when catalyzing the oxidation of endogenous and xenobiotic aldehydes to the corresponding carboxylic acid products.

Although challenging, the development of a selective activity-based fluorescent probe for ALDH1A1 would enable detection of CSCs, as well as concurrently report on their degree of stemness. In this regard, there is a gradient of ALDH1A1 activity ranging from high in CSCs to low in differentiated cancer cells (infra vide). Several probes have been developed for ALDH, including BODIPY-aminoacetaldehyde (BAAA). However, these examples suffer from major drawbacks.

Because BAAA is equally fluorescent compared to it turned over carboxylate product, CSCs are identified based on their ability to retain the BAAA product relative to the unactivated probe using efflux pump inhibitors. Additionally, an ALDH inhibitor (i.e., N,N-diethylaminobenzaldehyde (DEAB)) must also be used in tandem to distinguish between signal from ALDH activity non-specific accumulation in cells.

While these are useful tools for isolating CSCs from solid tumors and cell cultures, introduction of efflux pump and ALDH inhibitors to live animals will have unintended consequences. More importantly, BAAA exhibits cross-reactivity with several ALDH isoforms rendering the interpretation of experimental results challenging.

The problem is there are no selective probes for ALDH1A1 that can be independently used without inhibitors for the detection of cancer stem cells. Accordingly, there is a need for the development of a selective activity-based fluorescent probe for ALDH1A1 that would simplify the detection of CSCs without confounding consequences.

SUMMARY

Herein, is described the development of a highly selective, activity-based fluorescent probe to target elevated ALDH1A1 in CSCs. Through the application of established protocols that include identifying CSC surface markers, cultivation of tumorspheres, and assessment of tumorigenicity, we provide evidence the brightest AlDeSense cells possess CSC properties. Finally, we employ our probe to monitor CSC plasticity in a tumor model using live mice.

Accordingly, this disclosure provides a compound of Formula I:

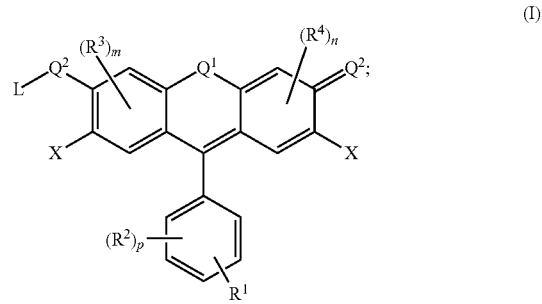

or a salt thereof, wherein $Q^1$ is O, S, $C(R^A)_2$, $Si(R^A)_2$, or $P(=O)R^A$, wherein each $R^A$ is independently H, $-(C_1-C_6)$alkyl, or $-O(C_1-C_6)$alkyl;

each $Q^2$ is independently O, S or $NR^B$, wherein $R^B$ is H or $-(C_1-C_6)$alkyl;

L is H or an enzymatically labile group;

each X is independently H, halo, nitro, or alkylsulfonyl;

$R^1$ is —CH(=O), —C(=O)($C_1$-$C_6$)alkyl, or —CH(OR)$_2$ wherein each R is independently H, —($C_1$-$C_6$)alkyl, or two R taken together form an acetal;

$R^2$, $R^3$ and $R^4$ are each independently halo, OH, —($C_1$-$C_6$)alkyl, —O($C_1$-$C_6$)alkyl, nitro, or phenyl wherein —($C_1$-$C_6$)alkyl and phenyl are optionally substituted with 1-5 substituents;

m and n are independently 0-2; and p is 0-4.

The invention provides novel compounds of Formulas I-V, intermediates for the synthesis of compounds of Formulas I-V, as well as methods of preparing compounds of Formulas I-V. The invention also provides compounds of Formulas I-V that are useful as intermediates for the synthesis of other useful compounds. The invention provides for the use of compounds of Formulas I-V for the manufacture of fluorescent probes useful for the imaging of cancer stem cells.

Also, this disclosure provides a method for imaging a cell comprising:
  a) contacting a cell with the fluorescent probe of Formula I disclosed above, wherein L is a labile group and $R^1$ is —CH(=O); and
  b) determining the difference in fluorescent intensity in the contacted cell relative to a control;
  wherein an enzyme in the cell cleaves the labile group to release a xanthenone moiety from the fluorescent probe, and aldehyde dehydrogenase (ALDH), when present in the contacted cell, oxidizes the aldehyde moiety $R^1$ of the xanthenone to a carboxyl moiety;
  wherein the fluorescent intensity of the contacted cell is modulated by the presence or absence of ALDH, thereby providing an image of aldehyde dehydrogenase activity in the contacted cell.

Additionally, this disclosure provides a method for imaging a cell comprising:
  a) contacting a cell and a fluorescent probe of Formula I disclosed above; and
  b) determining the fluorescent intensity in the contacted cell;
  wherein aldehyde dehydrogenase-$_1A_1$ (ALDH$_1$A$_1$), when present in the contacted cell, oxidizes the aldehyde moiety $R^1$ is —CH(=O) of Formula I to a carboxyl moiety; and
  wherein the fluorescent intensity of the contacted cell is modulated by the amount of ALDH$_1$A$_1$ present in the cell, thereby providing an image of aldehyde dehydrogenase activity in the contacted cell.

The invention provides for the use of the compositions described herein for use in imaging of cancer stem cells. The invention also provides for the use of a composition as described herein for the manufacture of fluorescent probes useful for the imaging of cancer stem cells.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

VioBlue®, (e) CD38− APC and (f) merged view. Pearson's R coefficients displayed were calculated between the signal of AlDeSense AM and each antibody for each cell with AlDeSense signal. Scale bar is 20 µm.

Figure 22:
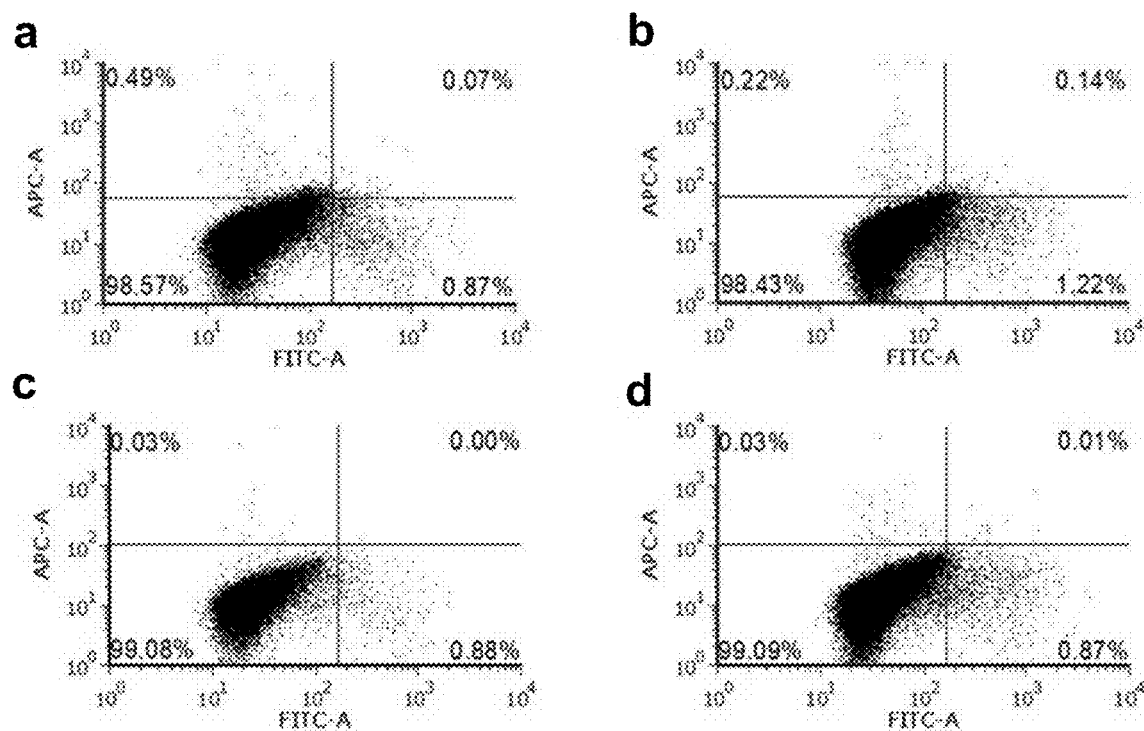

FIG. 22. Flow cytometry analysis of (a) patterned B16F0 melanoma stained with CD271-APC and Ctrl-AlDeSense, (b) patterned B16F0 melanoma stained with CD271-APC and AlDeSense, (c) nonpatterned B16F0 melanoma stained with CD271-APC and Ctrl-AlDeSense, and (d) nonpatterned B16F0 melanoma stained with CD271-APC and Ctrl-AlDeSense. Quadrants were set using unstained cells for CD271 (APC-A) signal and Ctrl-AlDeSense AM stained cells for AlDeSense (FITC) signal. Increased CD271 and AlDeSense staining was observed in patterned cells (upper right quadrant, b).

Figure 23:
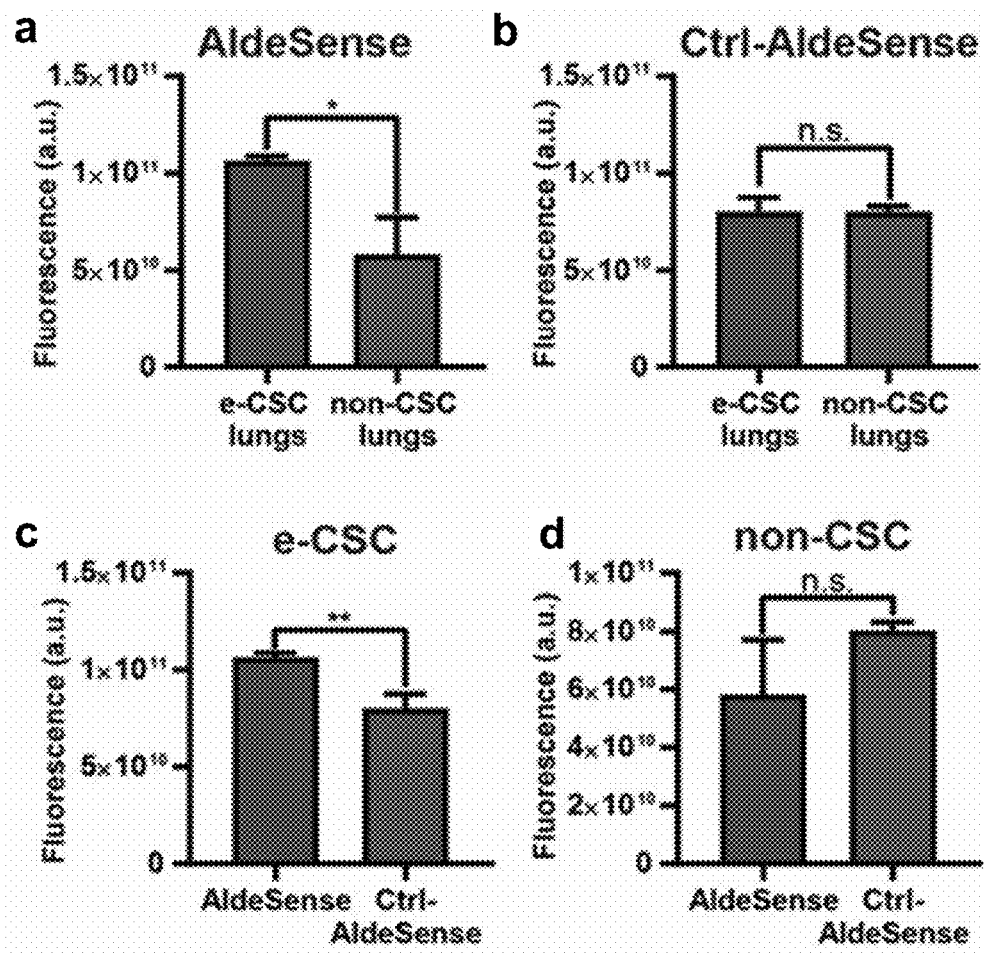

FIG. 23. Quantified fluorescence signal from lung metastases collected at day 7. Staining with AlDeSense (a) led to a significant difference in signal between e-CSC metastases and non-CSC metastases but staining with Ctrl-AlDeSense (b) did not show a difference between e-CSC and non-CSC. Furthermore, when analysing the e-CSC samples, AlDeSense showed a significant increase in signal in comparison to Ctrl-AlDeSense (c). However, this difference was not observed when analysing non-CSC samples (d). For graphs (a)-(d) error bars are ±SD, n=3 for each condition.

Figure 24:
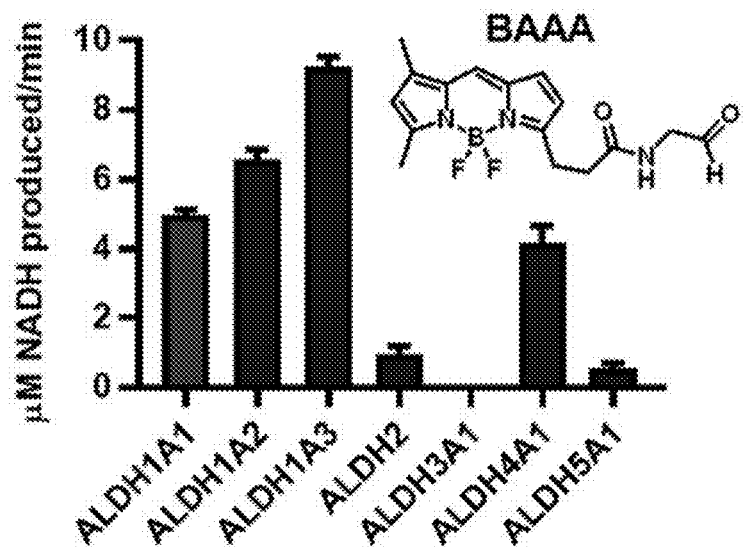

FIG. 24. Comparison of the reactivity of BAAA with various ALDH isoforms. UV/Vis activity of BAAA (18 µM) with 20 units of each ALDH isoform for 30 min at room temperature expressed as µM NADH produced/min (nd=not detected). All measurements were done in triplicate, error bars are ±SD.

Figure 25:
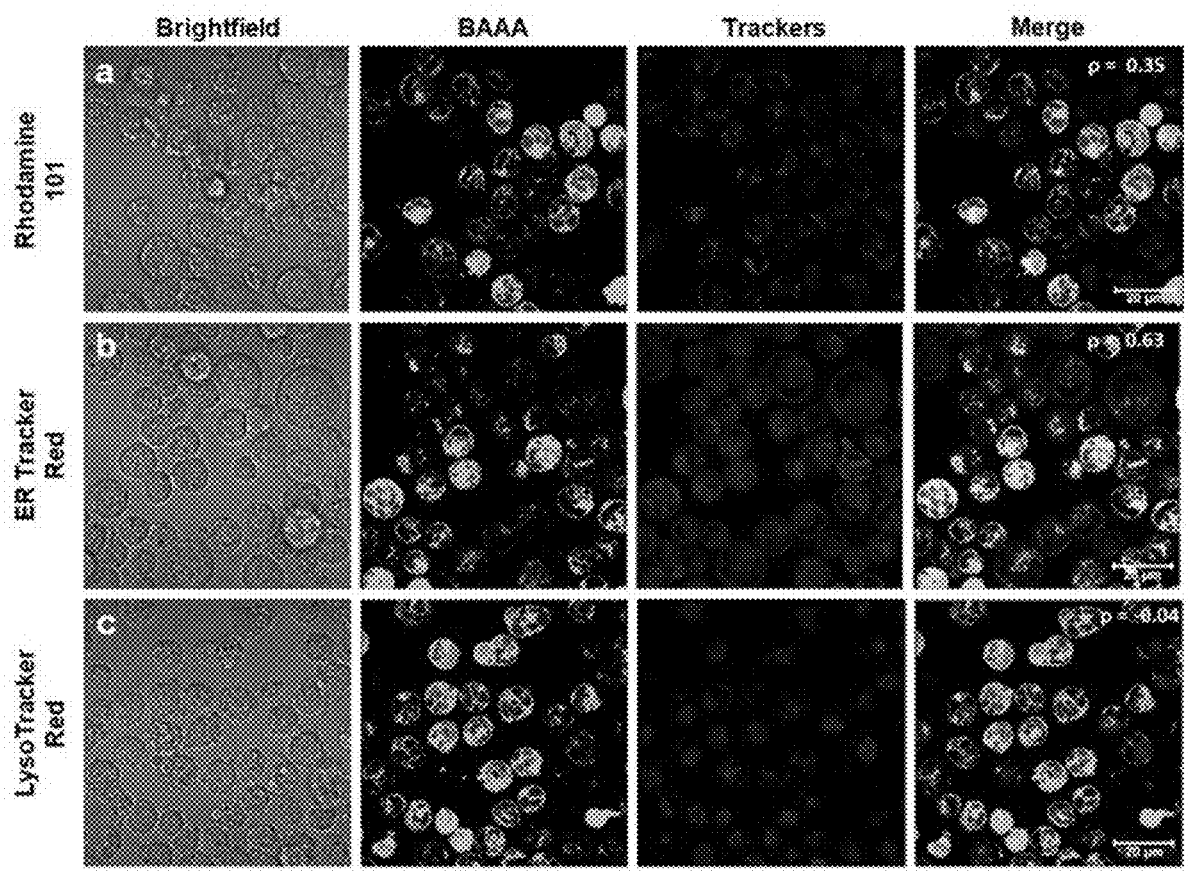

FIG. 25. Colocalization study of BAAA with various organelle-specific trackers. (a) Colocalization of AF with Rhodamine 101 methyl ester, (b) colocalization of AF with ER Tracker Red, and (c) colocalization of AF with LysoTracker Red. Pearson's R coefficients (p) are averages of 18 measurements over three images. Scale bar is 20 µm.

Figure 26:
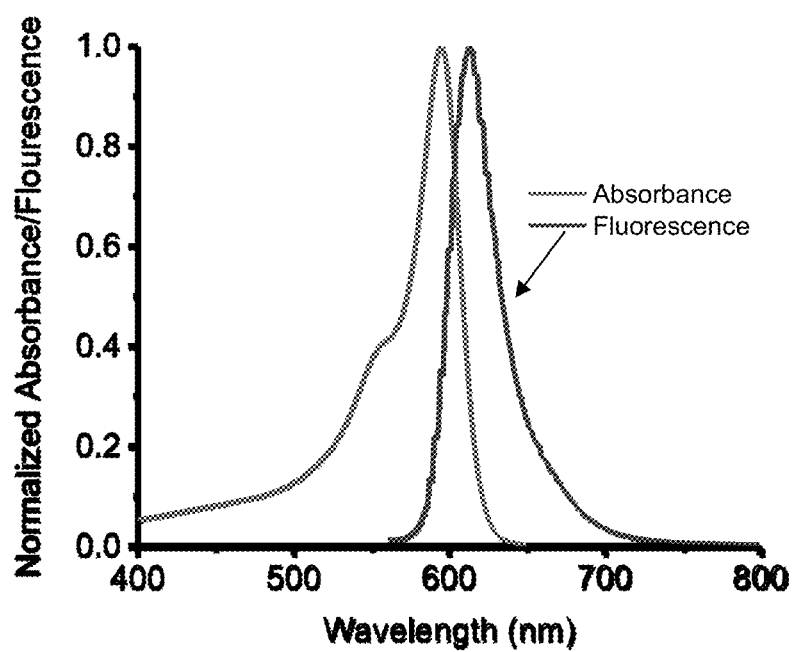
Figure 26:
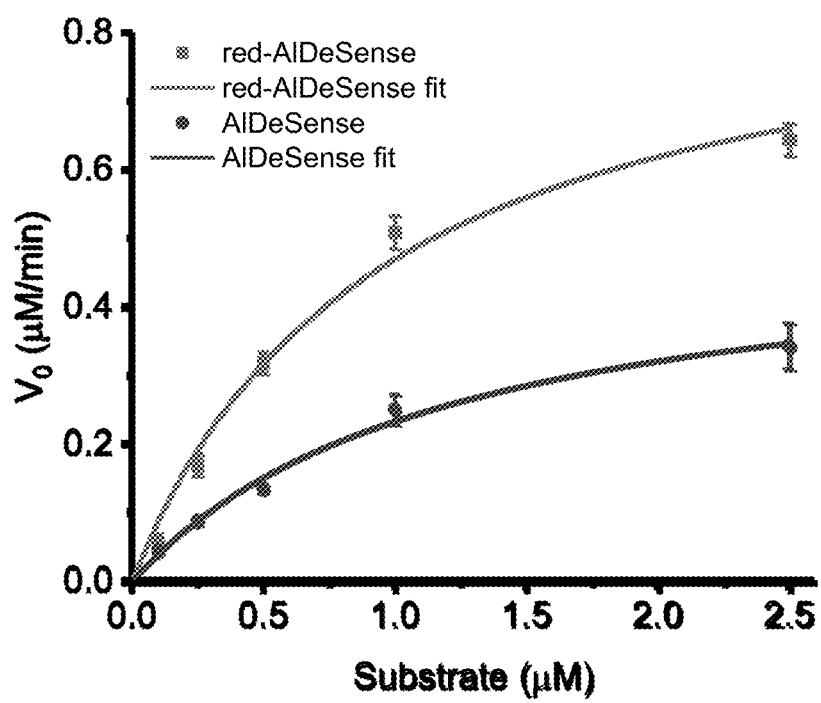
Figure 26:
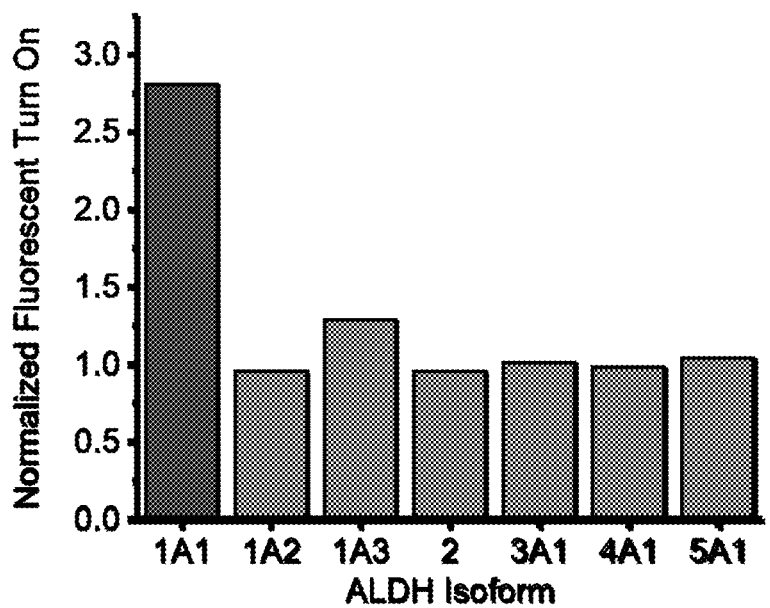
Figure 26:
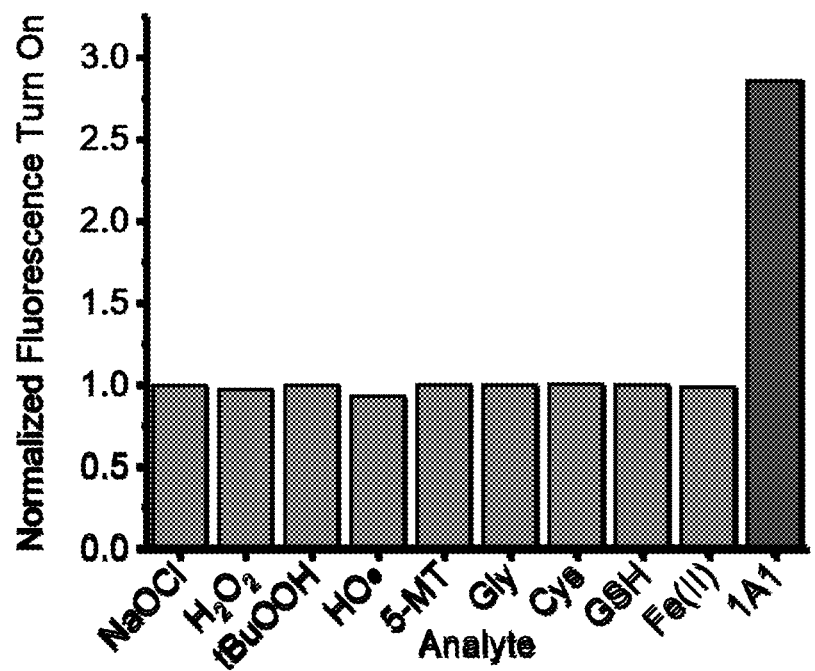

FIG. 26. (a) Normalized absorption and emission spectra (upon excitation at 594 nm) of red-AlDeSense. Normalized fluorescence turn on of red-AlDeSense by (b) ALDH1A1, (c) multiple ALDH isoforms, and (d) multiple biologically-relevant, reactive species. All assays were performed in 50 mM triethanolamine buffer red-AlDeSense was used at 2 µM. Enzyme concentrations affording 1 nmol substrate/ minute were used. Reactive species were tested at 100 µM, except glutathione which was at 1 mM. 5-MT=5-methoxytryptamine.

Figure 27:
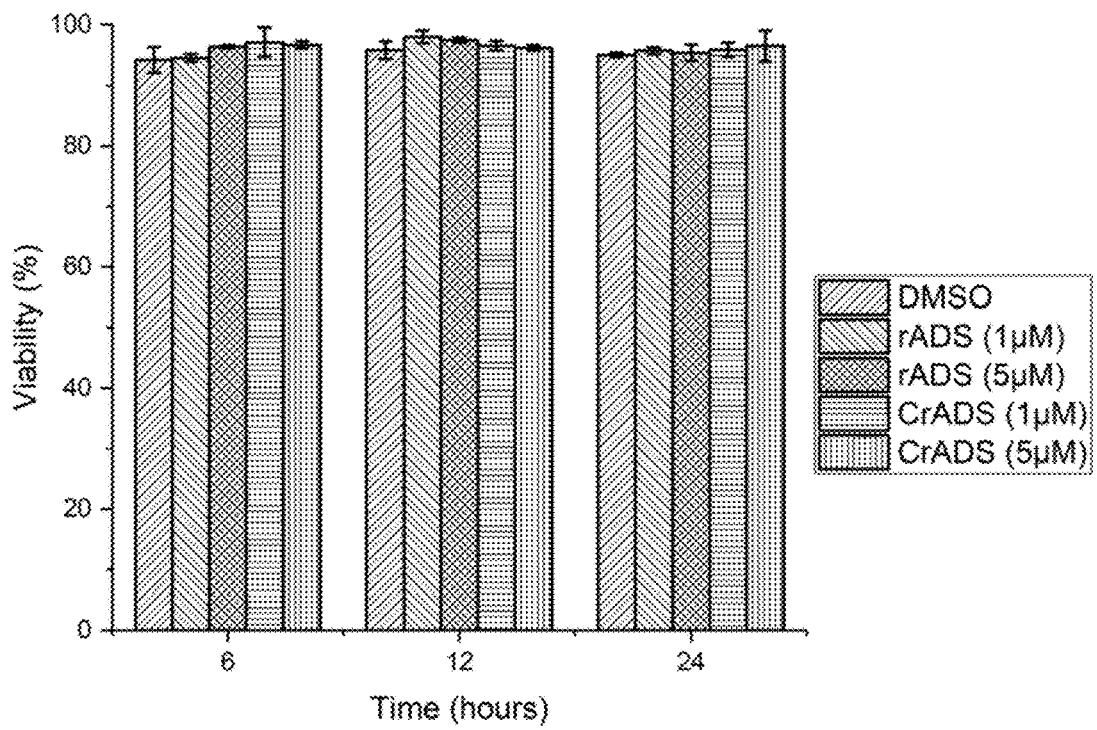

FIG. 27. Trypan blue cytotoxicity assay using K562 cells for red-AlDeSense (rADS) and Ctrl-red-AlDeSense (CrADS) over 6, 12, and 24 hours.

Figure 28:
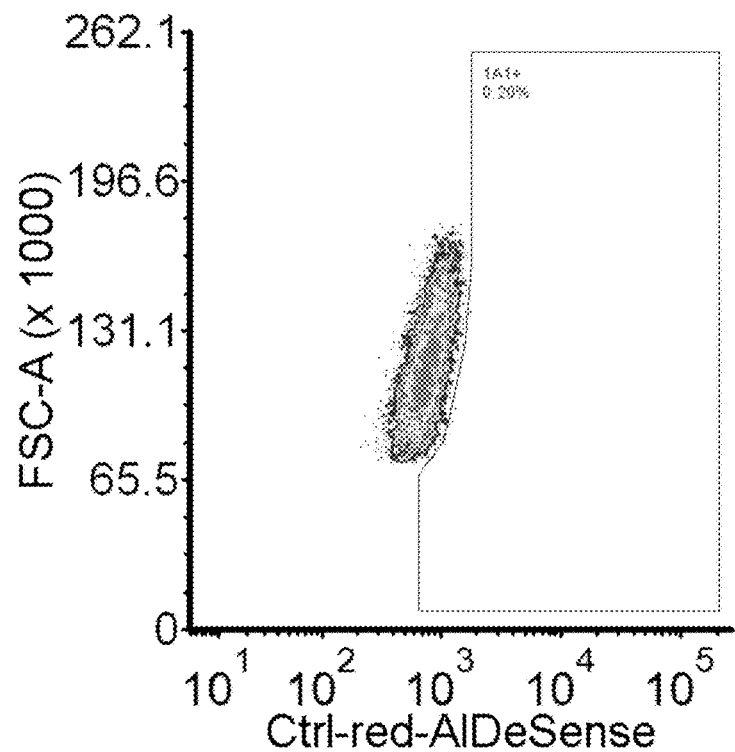
Figure 28:
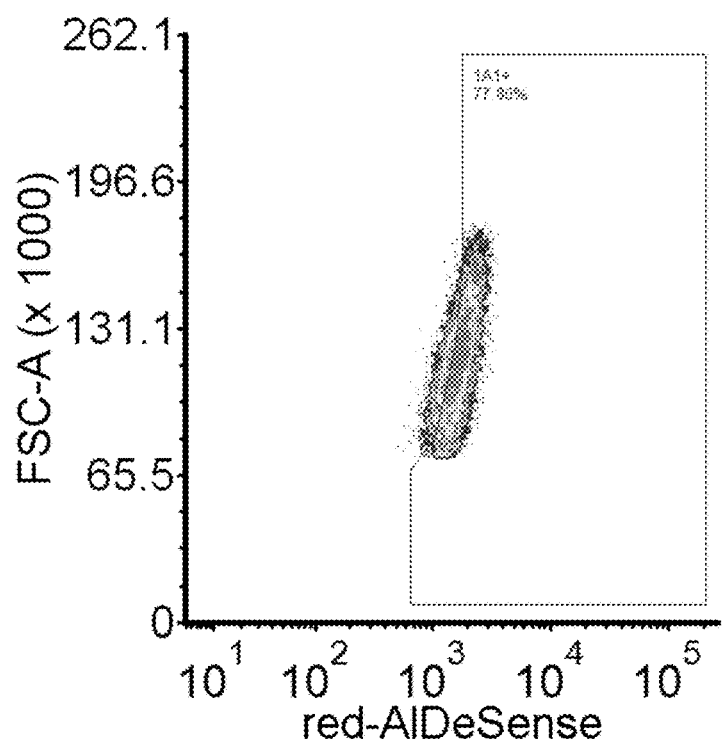
Figure 28:
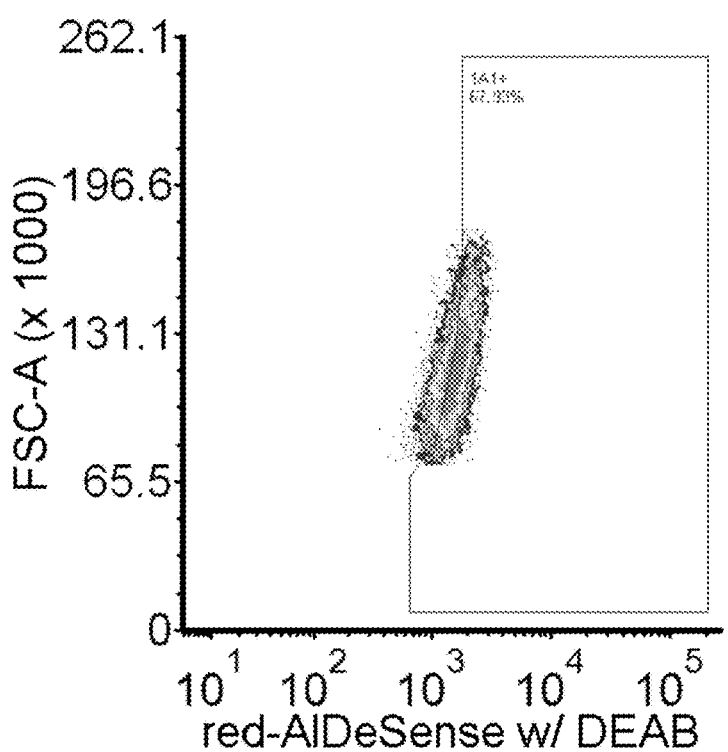
Figure 28:
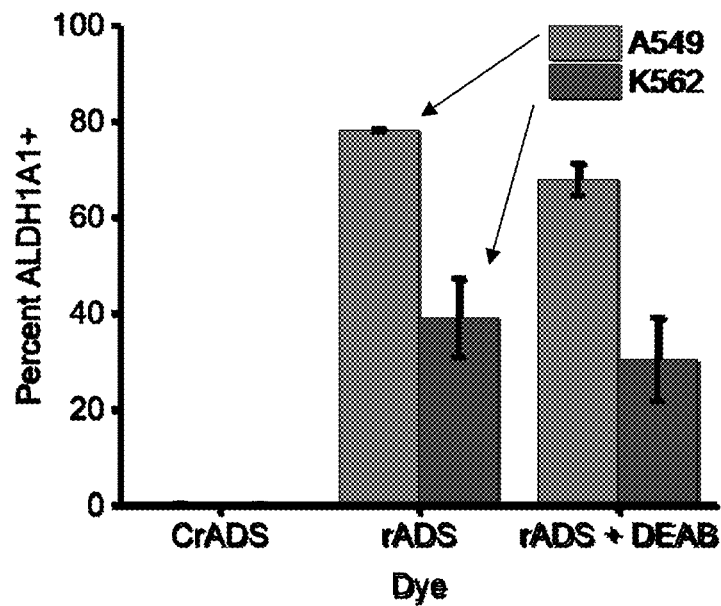
Figure 28:
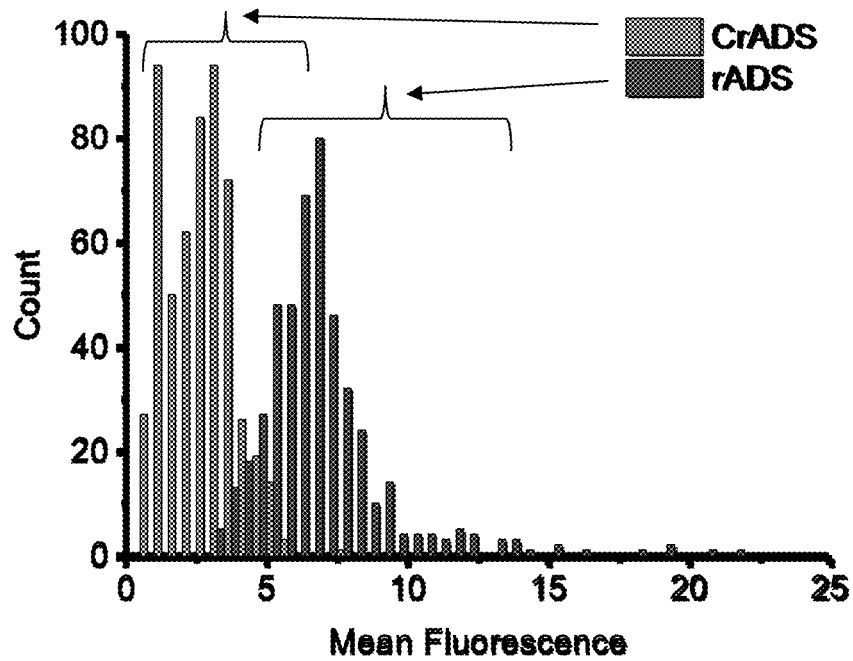
Figure 28:
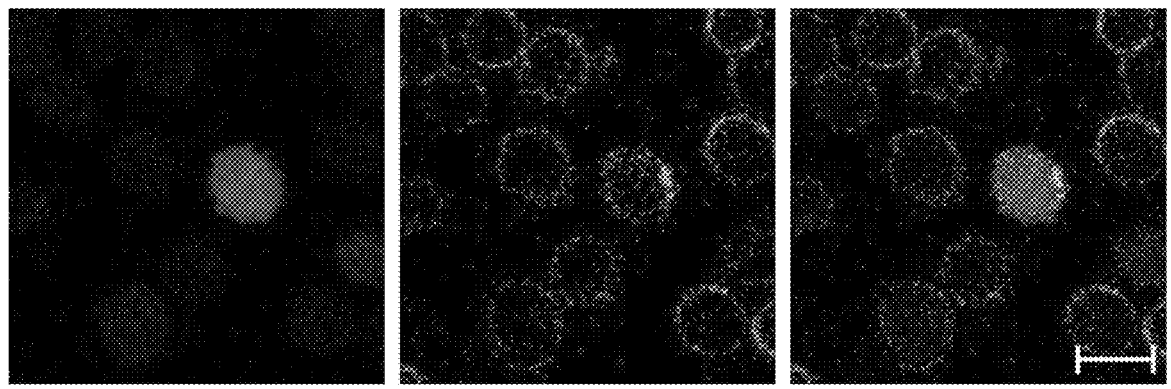

FIG. 28. Representative plots of the flow cytometry analysis of A549 cells stained for 10 minutes at 0° C. with (a) Ctrl-red-AlDeSense, (b) red-AlDeSense, and (c) red-AlDeSense plus 20 µM DEAB. (d) Quantified data of each assay performed in triplicate with A549 and K562 cells. (e) Histogram of the mean fluorescence of cells stained for 10 minutes at room temperature with Ctrl-red-AlDeSense or red-AlDeSense. (f) Representative confocal images of A549 cells co-stained with red-AlDeSense (red) and a FITC-labeled anti-CD44 antibody (CD44, green). All assays were performed using 1 µM Ctrl-red-AlDeSense or red-AlDeSense.

Figure 29:
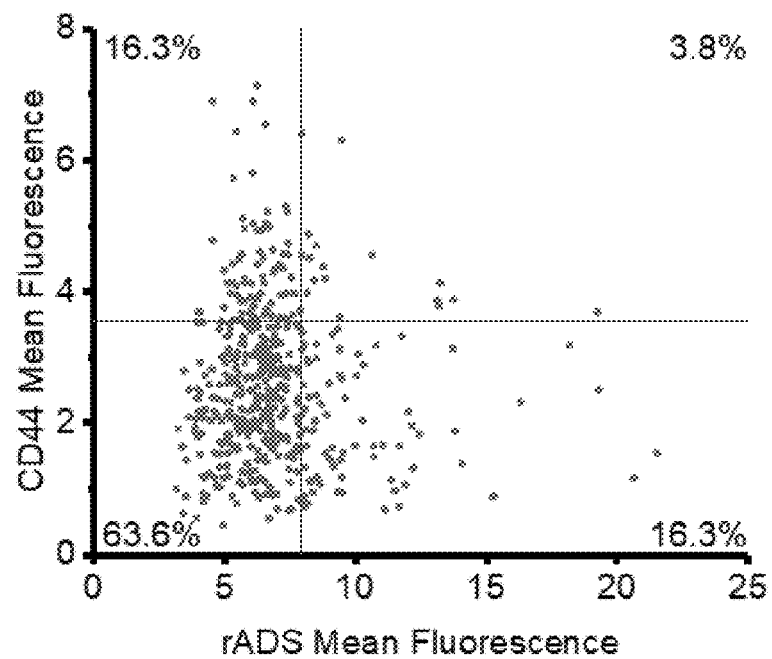
Figure 29:
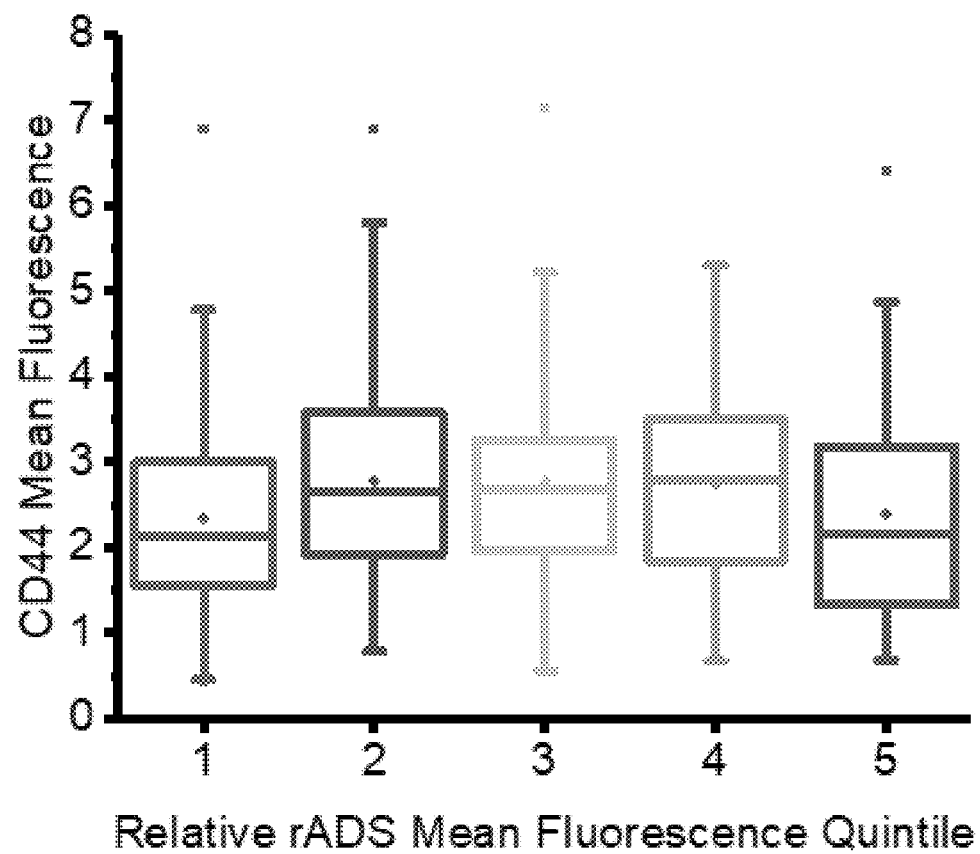

FIG. 29. A549 were cells co-stained with red-AlDeSense or Ctrl-red-AlDeSense and a FITC-labeled anti-CD44 antibody (CD44). Mean fluorescence values of both CD44 and red-AlDeSense were quantified for every cell. This was (a) plotted with quadrants indicating the top 20% of each population and (b) sorted into quintiles, wherein the first quintile comprises the lowest red-AlDeSense mean fluorescence. All assays were performed using 1 µM red-AlDeSense or Ctrl-AlDeSense.

Figure 30:
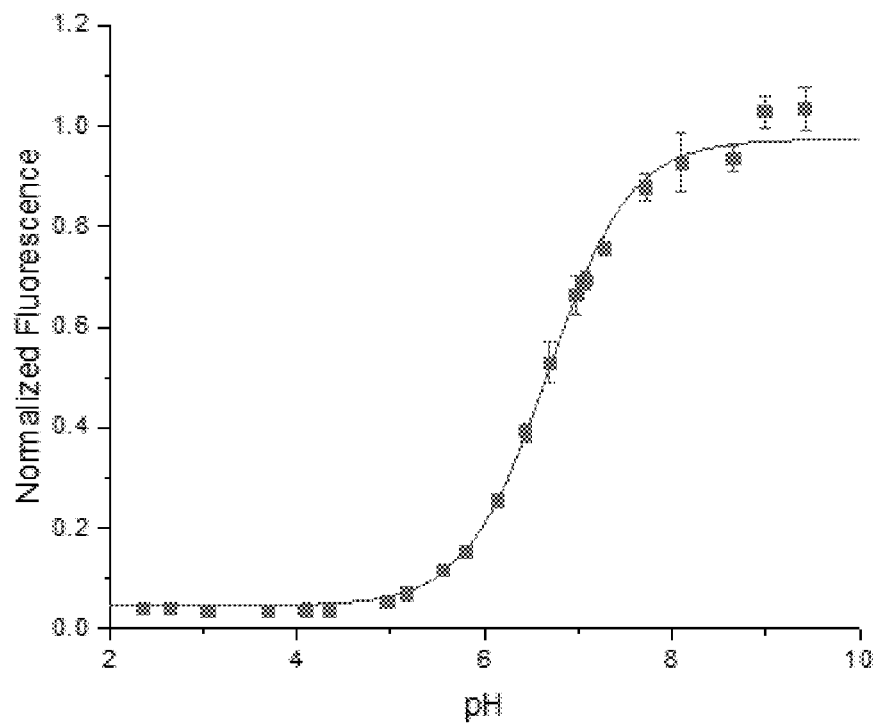
Figure 30:
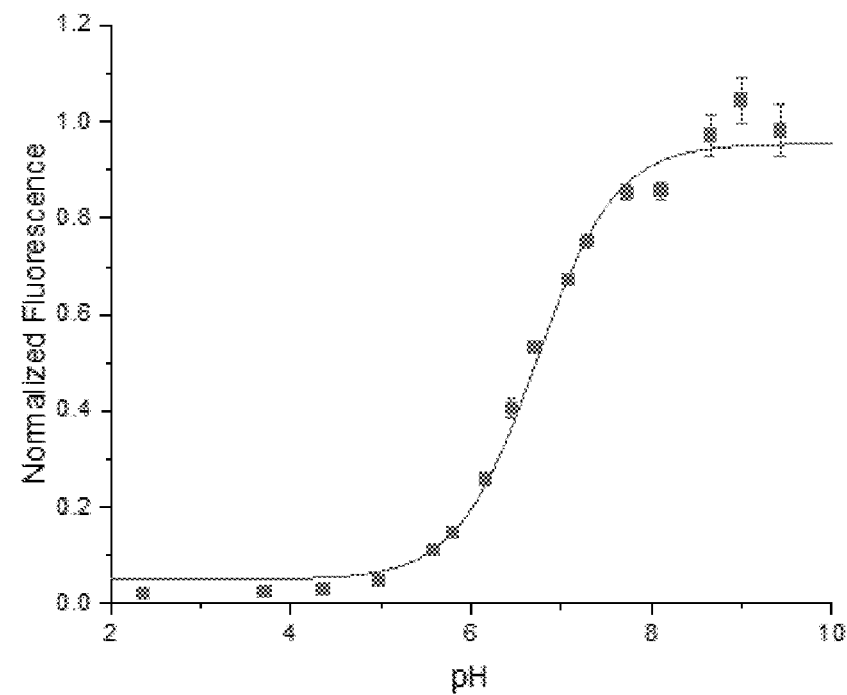

FIG. 30. pH profiles of (a) red-AlDeSense and (b) Ctrl-red-AlDeSense.

DETAILED DESCRIPTION

Cancer stem cells (CSCs) are progenitor cells that contribute to treatment-resistant phenotypes during relapse. CSCs exist in specific tissue microenvironments that cell cultures and more complex models cannot mimic. Therefore, the development of new approaches that can detect CSCs and report on specific properties (e.g., stem cell plasticity) in their native environment have profound implications for studying CSC biology.

Design of AlDeSense

Our ALDH1A1 probe, AlDeSense, is based on the photostable Pennsylvania Green dye platform and is equipped with a pendant benzaldehyde moiety (Table 1). Electron deficient aryl groups such as benzaldehyde can attenuate fluorescence via the donor-photoinduced electron transfer (d-PeT) quenching mechanism. This provides the desired signal enhancement upon conversion to the unquenched carboxylic acid by ALDH1A1.

Figure 6:
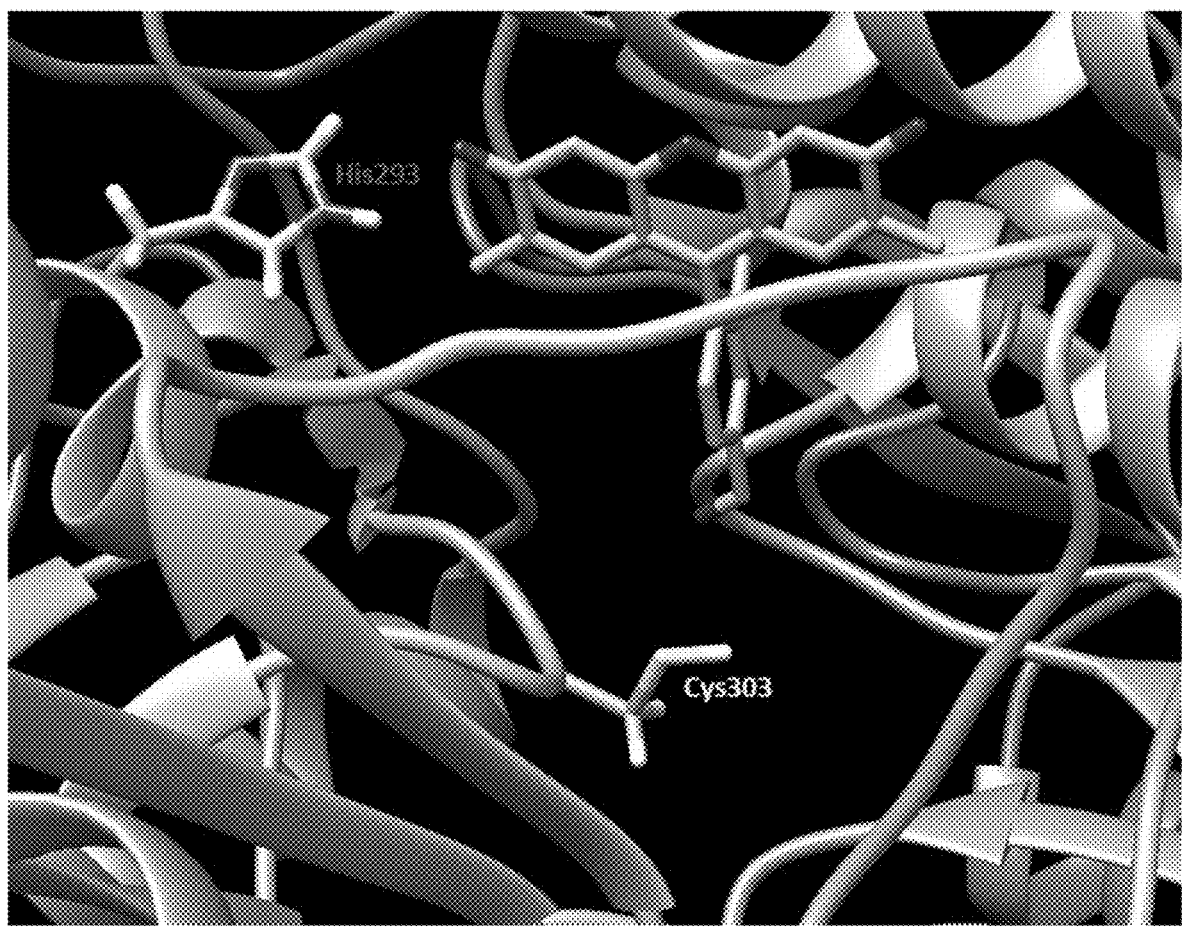
FIG. 6. Using Gaussian 03W, Hartree-Fock optimization was performed for deprotonated AlDeSense using the 3-21G basis set. All non-peptidic residues in the ALDH1A1 crystal structure (PDB ID: 4WB9) were removed prior to docking. Unbiased docking studies were performed using the AutoDock Vina application within UCSF Chimera.

We rationally selected the Pennsylvania Green scaffold because at physiological pH it is negatively charged (apparent pKa=4.81). The negative charge on the dye is expected to negate the need for efflux pump inhibitors because the turned over product will be dianionic and less able to cross the cell membrane. The low pKa serves a second purpose since it can presumably form an ionic interaction with His-293 located at the entrance of the active site (FIG. 6). This imparts selectivity because the corresponding His residue is not present in the other ALDH isoforms.

Figure 7:
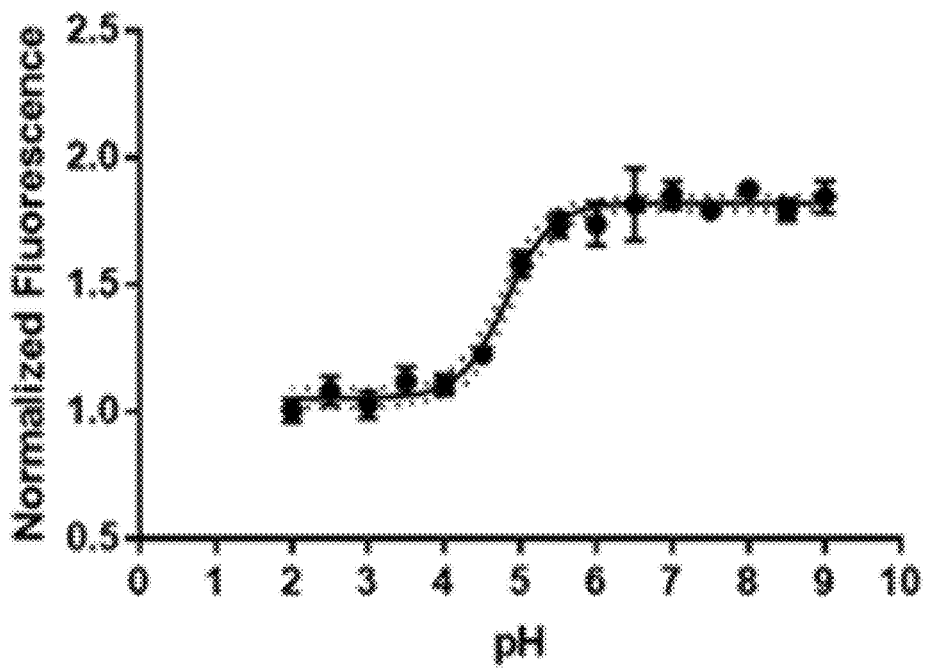
FIG. 7. pH profiles of AlDeSense and Ctrl-AlDeSense. The fluorescence of 1 µM of each compound was measured in 40 mM Britton-Robinson buffer at pH 2-9 in 0.5 pH intervals. Each measurement was performed in triplicate. Graphpad Prism (version 7.03) was used to plot the data with a sigmoidal fit. Error bars are ±standard deviation (SD).
Figure 7:
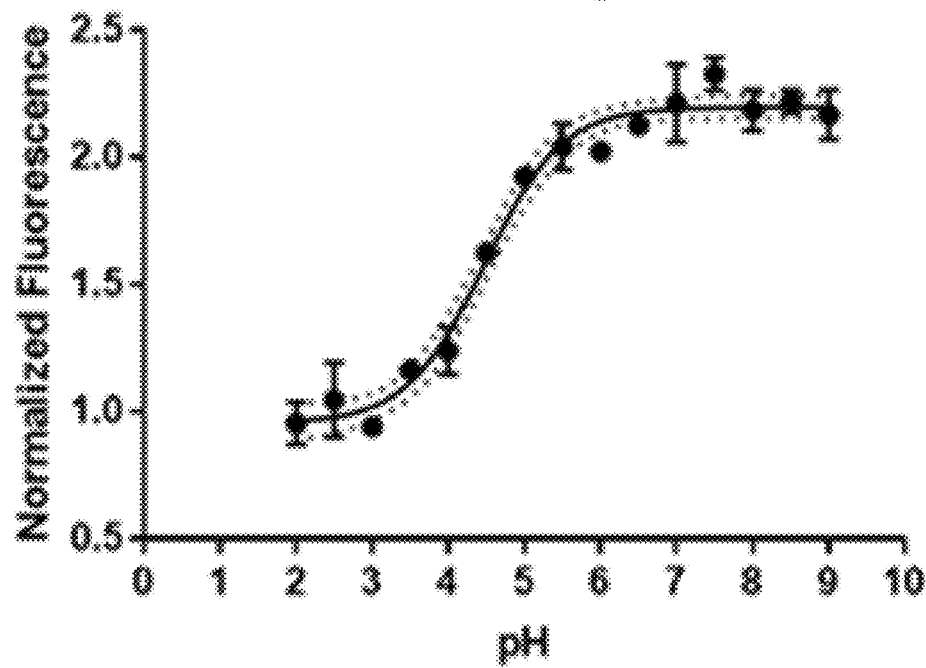
Figure 8:
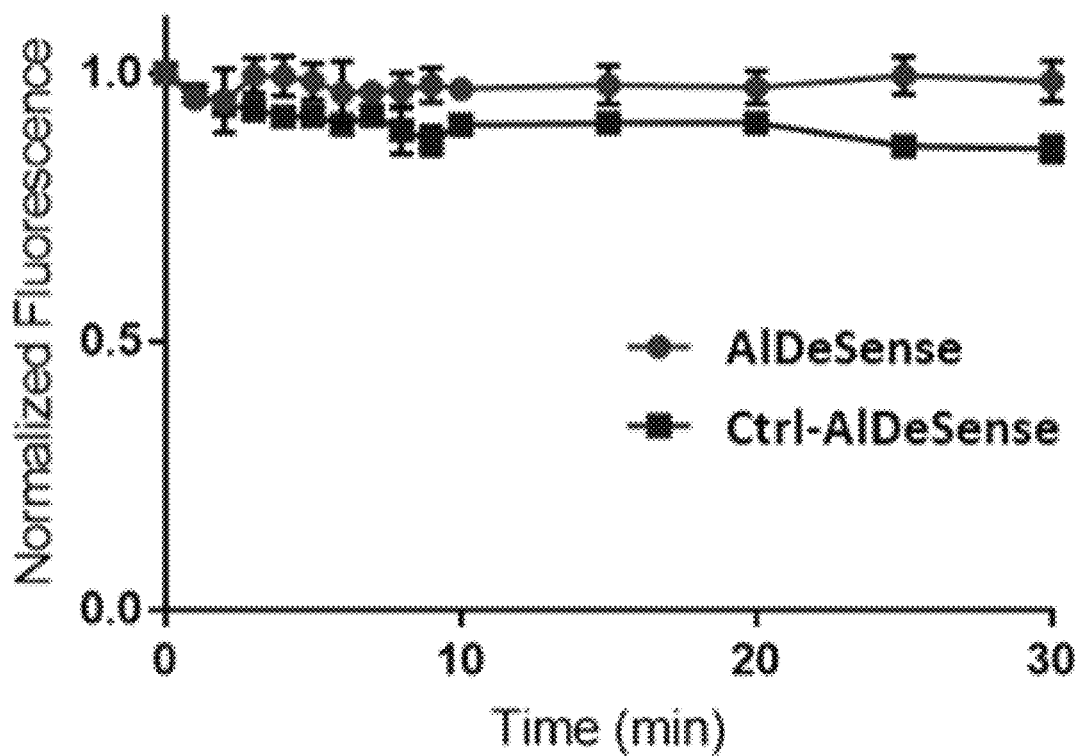
FIG. 8. Normalized fluorescence of AlDeSense and Ctrl-AlDeSense over time after repeated irradiation at 480 nm in an IVIS spectrum imaging system. Measurements were performed in triplicate; error bars are ±SD.

As predicted, the benzaldehyde moiety will also augment isoform selectivity, since benzaldehydes are better substrates for ALDH1A1 than many of the other ALDH isoforms. Despite the fact that AlDeSense is weakly fluorescent until activated, non-specific staining can still contribute to misidentification of non-CSC populations. To account for this and circumvent the need for ALDH inhibitors, we developed Ctrl-AlDeSense, a non-responsive matching control reagent (Table 1). Although Ctrl-AlDeSense is structurally similar to AlDeSense and displays nearly identical physical properties, replacing the benzaldehyde moiety with an acetophenone group renders it unreactive to ALDH1A1 (Table 1, FIG. 7 and FIG. 8).

TABLE 1

Chemical structures of AlDeSense and Ctrl-AlDeSense. Comparison of photophysical and chemical properties of AlDeSense and Ctrl-AlDeSense.

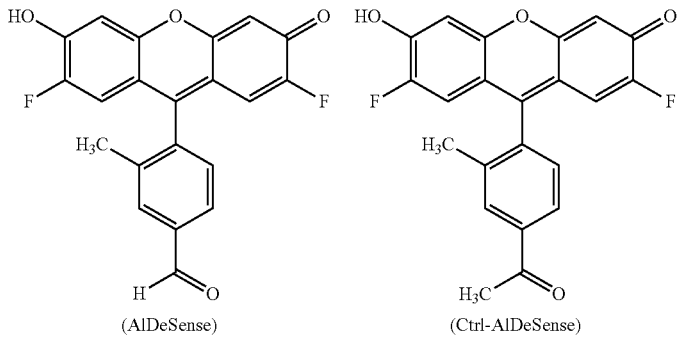

(AlDeSense)     (Ctrl-AlDeSense)

| Compound | $\lambda_{abs}$ (nm) | $\lambda_{em}$ (nm) | $\varepsilon$ ($M^{-1}cm^{-1}$) | $\Phi_F$ | $pK_a$ | Log $D_{7.4}$ | Turn-on (fold) |
|---|---|---|---|---|---|---|---|
| AlDeSense | 496 | 516 | $6.1 \times 10^4$ | 0.041 | 4.81 | 0.88 | 20.0 |
| Ctrl-AlDeSense | 496 | 518 | $6.8 \times 10^4$ | 0.039 | 4.47 | 0.87 | 0 |

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as Hawley's Condensed Chemical Dictionary 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, +10%, +20%, or +25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of the compounds or compositions of the disclosure into a subject (or cells) by a method or route which results in at least partial localization of the composition to a desired site. The compositions can be administered (in vivo or in vitro) by any appropriate route which results in delivery to a desired location in the subject.

The compositions described herein may be administered with additional compositions to prolong stability and activity of the compositions.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

This disclosure provides methods of making the compounds and compositions of the invention. The compounds and compositions can be prepared by any of the applicable techniques described herein, optionally in combination with standard techniques of organic synthesis. Many techniques such as etherification and esterification are well known in the art. However, many of these techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as March's Advanced Organic Chemistry: Reactions, Mechanisms, and Structure, 5th Ed., by M. B. Smith and J. March (John Wiley & Sons, New York, 2001); Comprehensive Organic Synthesis. Selectivity, Strategy & Efficiency in Modern Organic Chemistry. In 9 Volumes, Barry M. Trost, Editor-in-Chief (Pergamon Press, New York, 1993 printing); Advanced Organic Chemistry, Part B: Reactions and Synthesis, Second Edition, Cary and Sundberg (1983);

The formulas and compounds described herein can be modified using protecting groups. Suitable amino and carboxy protecting groups are known to those skilled in the art (see for example, Protecting Groups in Organic Synthesis, Second Edition, Greene, T. W., and Wutz, P. G. M., John Wiley & Sons, New York, and references cited therein; Philip J. Kocienski; Protecting Groups (Georg Thieme Verlag Stuttgart, New York, 1994), and references cited therein); and Comprehensive Organic Transformations, Larock, R. C., Second Edition, John Wiley & Sons, New York (1999), and referenced cited therein.

As used herein, the term "substituted" or "substituent" is intended to indicate that one or more (for example, 1-20 in various embodiments, 1-10 in other embodiments, 1, 2, 3, 4, or 5; in some embodiments 1, 2, or 3; and in other embodiments 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Additionally, non-limiting examples of substituents that can be bonded to a substituted carbon (or other) atom include F, $C_1$, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted. When a substituent is monovalent, such as, for example, F or $C_1$, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, wherein the C and the O are double bonded. Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms and often 1-12, 1-10, 1-8, 1-6, 1-4 carbon atoms, or any range in-between (such as 2-6 or 3-6 carbon atoms). As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group can include both alkenyl and alkynyl groups. The alkyl can be a monovalent hydrocarbon radical, as described and exemplified above, or it can be a divalent hydrocarbon radical (i.e., an alkylene).

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. In other embodiments, the aryl group can have 6 to 60 carbons atoms, 6 to 120 carbon atoms, or 6 to 240 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted.

The term "enzymatically labile group" refers to a group that can be removed from a parent molecule via an enzyme. The enzymatically labile group can be considered to be like a protecting group of a functional group. For example, an ester group can mask a hydroxyl or phenolic group. The particular ester group is selected by persons skilled in the art to be chemically stable in certain environments, but unstable when in contact with certain enzymes. Such a masking ester group may be removed enzymatically to unmask the hydroxyl or phenolic group, and is therefore an example of a enzymatically labile group.

Embodiments of the Invention

This disclosure provides a compound of Formula I:

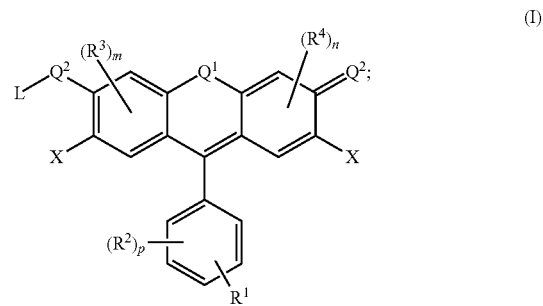

or a salt thereof, wherein $Q^1$ is O, S, C(R$^4$)$_2$, Si(R$^4$)$_2$, or P(=O)R$^4$, wherein each R$^4$ is independently H, —(C$_1$-C$_6$)alkyl, or —O(C$_1$-C$_6$)alkyl;

each $Q^2$ is independently O, S or $NR^B$, wherein $R^B$ is H or $—(C_1-C_6)$alkyl;

L is H or an enzymatically labile group;

each X is independently H, halo, nitro, or alkylsulfonyl;

$R^1$ is $—CH(=O)$, $—C(=O)(C_1-C_6)$alkyl, or $—CH(OR)_2$ wherein each R is independently H, $—(C_1-C_6)$alkyl, or two R taken together form an acetal;

$R^2$, $R^3$ and $R^4$ are each independently halo, OH, $—(C_1-C_6)$alkyl, $—O(C_1-C_6)$alkyl, or phenyl wherein phenyl is optionally substituted with 1-5 substituents;

m and n are independently 0-2; and p is 0-4.

In some embodiments the compound of Formula I is not:

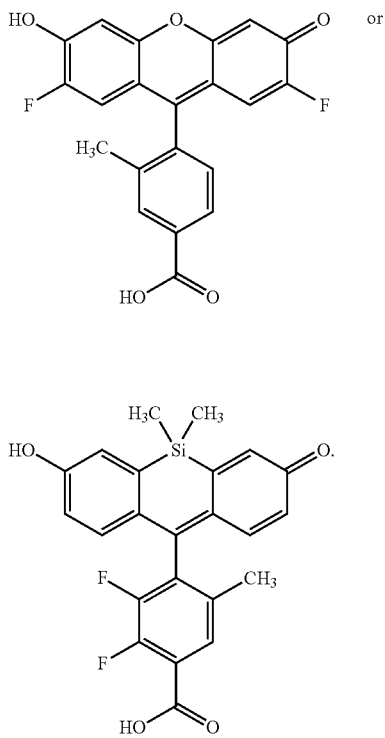

In additional embodiments:
$Q^1$ is O, S, $C(R^4)_2$, $Si(R^4)_2$, or $P(=O)R^A$, wherein each $R^A$ is independently H, $(C_1-C_6)$alkyl, or $—O(C_1-C_6)$alkyl;

each $Q^2$ is independently O, S or $NR^B$, wherein $R^B$ is H or $—(C_1-C_6)$alkyl;

L is H or an enzymatically labile group;

each X is independently H, halo, nitro, or alkylsulfonyl;

$R^1$ is $—CH(=O)$, $—CH(OR)_2$, or $—C(=O)R$, wherein R is H, $—(C_1-C_6)$alkyl, or two R taken together optionally form a ketal when $R^1$ is $—CH(OR)_2$;

$R^2$, $R^3$ and $R^4$ are each independently halo, OH, $—(C_1-C_6)$alkyl, $—O(C_1-C_6)$alkyl, nitro, or phenyl wherein $—(C_1-C_6)$alkyl and phenyl are optionally substituted with 1-5 substituents;

m and n are independently 0-2; and p is 0-4.

In some other embodiments, $R^1$ is $—C(=O)OR$ wherein R is $—(C_1-C_6)$alkyl. In other various embodiments, L is a labile group. In some further embodiments, the labile group is an ester or comprises an ester. In additional embodiments, the labile group is $—C(R^C)_2OC(=O)$alkyl wherein each $R^C$ is independently H or $—(C_1-C_6)$alkyl. In yet other embodiments, each Q is O and $R^2$ is $—(C_1-C_6)$alkyl. In further embodiments, X is halo and $R^1$ is $—CH(=O)$, $—CH(OR)_2$, $—C(=O)R$, or $—C(=O)OR$. In various other embodiments, $R^1$ is $—CH(=O)$, $—CH(OR)_2$, or $—C(=O)R$, wherein R is H, $—(C_1-C_6)$alkyl, or two R taken together optionally form a ketal when $R^1$ is $—CH(OR)_2$.

In some embodiments, L is the enzymatically labile group and the labile group comprises an ester moiety. In other embodiments, the labile group is $—C(R^C)_2OC(=O)$alkyl wherein each $R^C$ is independently H or $—(C_1-C_6)$alkyl. In other embodiments, $Q^1$ and $Q^2$ are O, and $R^2$ is $—(C_1-C_6)$alkyl. In further embodiments, $Q^1$ is $Si(R^4)_2$. In some other embodiments, X is halo and each $R^2$ is independently halo or $—(C_1-C_6)$alkyl. In yet other embodiments, X is H and each $R^2$ is independently halo or $—(C_1-C_6)$alkyl wherein at least one $R^2$ comprises halo.

In additional embodiments, the compound of Formula I is a compound of Formula II:

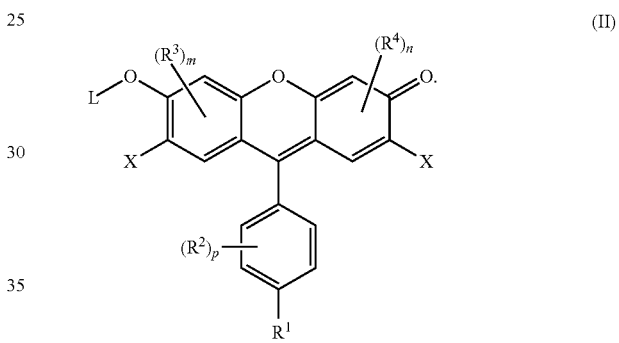

In some other embodiments, the labile group L comprises an ester moiety. In yet other embodiments, X is halo and $R^2$ is $—(C_1-C_6)$alkyl.

In additional embodiments, the compound of Formula I is a compound of Formula IIB:

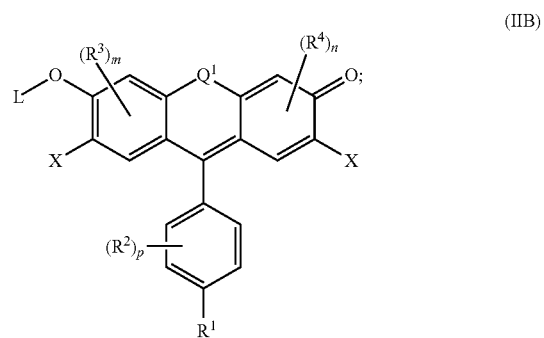

wherein $Q^1$ is O or $Si(R^4)_2$. In other embodiments, each X is independently H or halo; and each $R^2$ is independently halo or $—(C_1-C_6)$alkyl.

In yet other various embodiments, the compound of Formula I is a compound of Formula III:

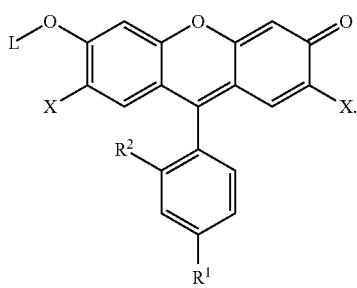

(III)

In additional embodiments, L is a labile group. In some embodiments, the labile group is —CH₂OC(=O)alkyl. In further embodiments, L is H and R² is —(C₁-C₆)alkyl. In yet other embodiments, R¹ is —CH(=O), —CH(OCH₃)₂, —C(=O)CH₃, or —C(=O)OH. In some other embodiments, X is halo and R² is —(C₁-C₆)alkyl. In various other embodiments, X is fluoro, L is H and R² is —(C₁-C₆)alkyl. In yet further embodiments, X is fluoro and L is —CH₂OC(=O)CH₃. In other embodiments, R¹ is —CH(=O) or —C(=O)OH. In other additional embodiments, R¹ is —C(=O)CH₃. In some further embodiments, R² is CH₃.

In other additional embodiments, the compound of Formula I is a compound of Formula IIIB:

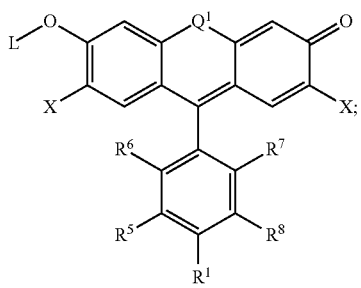

(IIIB)

wherein

Q¹ is O or Si(R^A)₂;

L is H or —CH₂OC(=O)alkyl;

X is H or halo; and

R⁵, R⁶, R⁷ and R⁸ are each independently H, halo, OH, —(C₁-C₆)alkyl, —O(C₁-C₆)alkyl, or nitro wherein —(C₁-C₆)alkyl is optionally substituted with 1-5 substituents.

In some embodiments, R⁷ is —(C₁-C₆)alkyl, —(C₂-C₆)alkyl, or —(C₃-C₆)alkyl; or R⁷ is —CH₃. In other embodiments, R⁵, R⁶ and R⁸ are each independently H or halo. In further embodiments, R⁵, R⁶ and R⁸ are H; and L is H and R⁷ is —(C₁-C₆)alkyl; or R¹ is —CH(=O), —CH(OCH₃)₂, or —C(=O)CH₃; or X is halo and R⁷ is —(C₁-C₆)alkyl; or X is fluoro, L is H and R⁷ is —(C₁-C₆)alkyl.

In yet other embodiments, X is fluoro and L is —CH₂OC(=O)CH₃. In other embodiments, R¹ is —CH(=O); or R¹ is —C(=O)CH₃.

In other various embodiments, the compound of Formula I is a compound of Formula (IV):

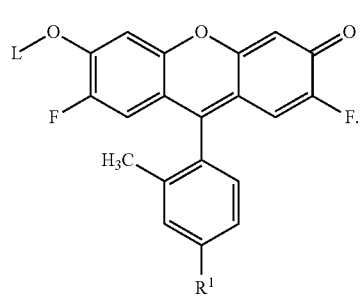

(IV)

In some embodiments, L is —CH₂OC(=O)CH₃; and R¹ is —CH(=O). In other embodiments, the compound of Formula I is:

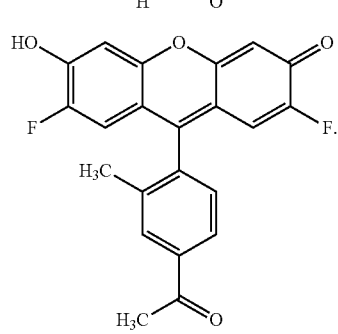

(AlDeSense)

or

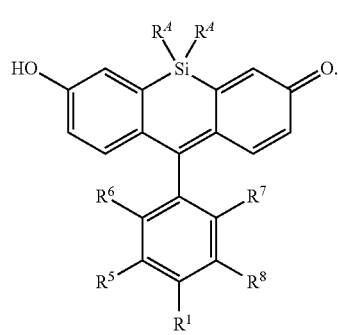

(Ctrl-AlDeSense)

In yet further embodiments, a compound of Formula I is a compound of Formula V:

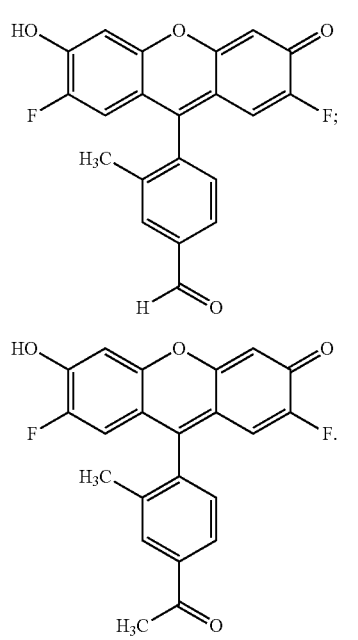

(V)

In some embodiments:

$R^4$ and $R^7$ are —$(C_1$-$C_6)$alkyl;

$R^1$ is —CH(=O), —CH(OCH$_3$)$_2$, or —C(=O)CH$_3$; and $R^5$, $R^6$ and $R^8$ are each independently H or halo.

In other embodiments, $R^5$ and $R^6$ are halo and $R^8$ is H. In further embodiments, the compound of Formula I is:

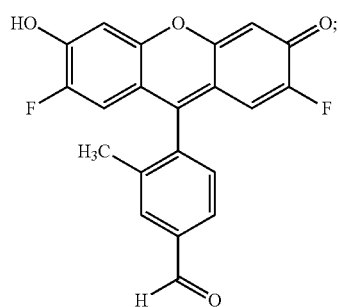
(AlDeSense)

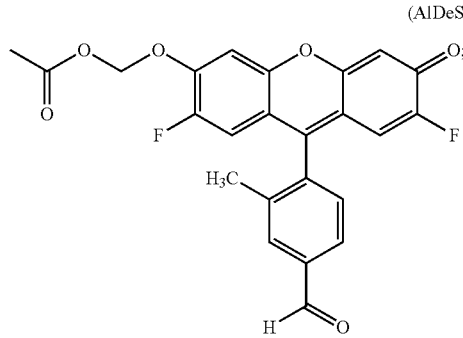
(AlDeSense AM)

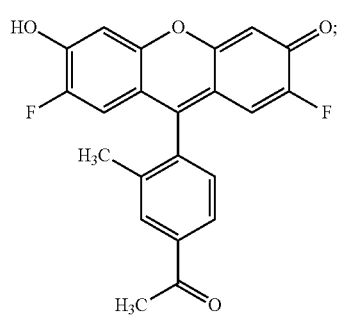
(Ctrl-AlDeSense)

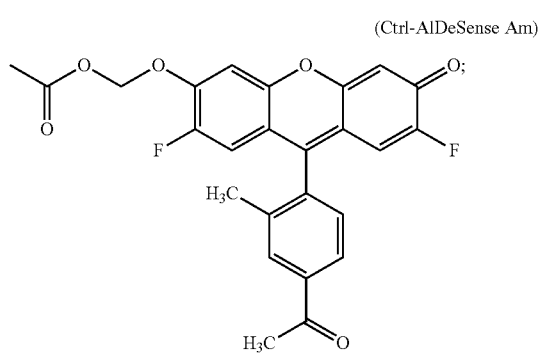
(Ctrl-AlDeSense Am)

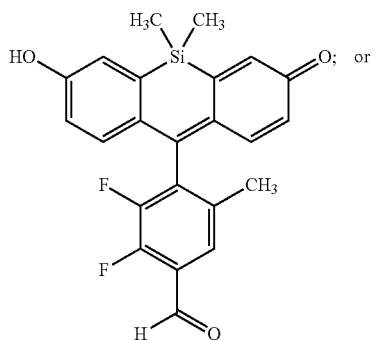
(red-AlDeSense)

or

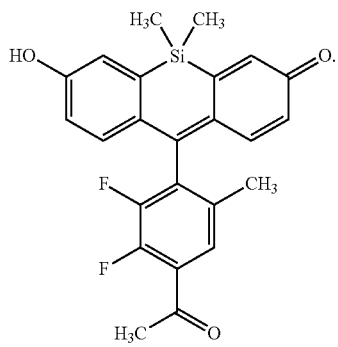
(Ctrl-red-AlDeSense)

This disclosure also provides a method for imaging a cell comprising:
a) contacting a cell with a fluorescent probe according to the compounds disclosed herein, wherein L is a labile group and $R^1$ is —CH(=O) in the fluorescent probe of Formulas I-IV; and
b) determining the difference in fluorescent intensity in the contacted cell relative to a control;
wherein an enzyme in the cell cleaves the labile group (when present) to release a xanthenone moiety from the fluorescent probe, and aldehyde dehydrogenase (ALDH), when present in the contacted cell, oxidizes the aldehyde moiety $R^1$ of the xanthenone to a carboxyl moiety;
wherein the fluorescent intensity of the contacted cell is modulated by the presence or absence of ALDH, thereby providing an image of aldehyde dehydrogenase activity in the contacted cell.

Additionally, this disclosure provides a method for imaging a cell comprising:
a) contacting a cell with a fluorescent probe of Formula I:

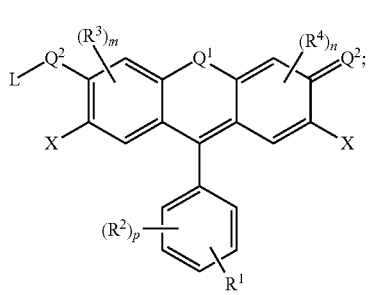

or a salt thereof, wherein
$Q^1$ is O, S, C($R^4$)$_2$, Si($R^4$)$_2$, or P(=O)$R^4$, wherein each $R^4$ is independently H, —$(C_1$-$C_6)$alkyl, or —O$(C_1$-$C_6)$alkyl;

each $Q^2$ is independently O, S or $NR^B$, wherein $R^B$ is H or —$(C_1-C_6)$alkyl;

L is an enzymatically labile group;

each X is independently H, halo, nitro, or alkylsulfonyl;

$R^1$ is —CH(=O), —C(=O)$(C_1-C_6)$alkyl, or —CH$(OR)_2$ wherein each R is independently H, —$(C_1-C_6)$alkyl, or two R taken together form an acetal;

$R^2$, $R^3$ and $R^4$ are each independently halo, OH, —$(C_1-C_6)$alkyl, —O$(C_1-C_6)$alkyl, or phenyl wherein phenyl is optionally substituted with 1-5 substituents;

m and n are independently 0-2; and p is 0-4; and b) determining the fluorescent intensity in the contacted cell;

wherein an enzyme in the cell cleaves the labile group (when present) to release a xanthenone moiety from the fluorescent probe, and aldehyde dehydrogenase (ALDH), when present in the contacted cell, oxidizes the aldehyde moiety $R^1$ of the xanthenone to a carboxyl moiety;

wherein the fluorescent intensity of the contacted cell is modulated by the presence or absence of ALDH, thereby providing an image of aldehyde dehydrogenase activity in the contacted cell.

In various additional embodiments, the cell is a normal stem cell cancer stem cell. In other embodiments, the fluorescent probe is cell permeable. In some additional embodiments, ALDH is the isoform ALDH-1A1 and the fluorescent probe is selective for ALDH-1A1. In various other embodiments, the fluorescent probe is AlDeSense AM or red-AlDeSense; the xanthenone moiety is (i):

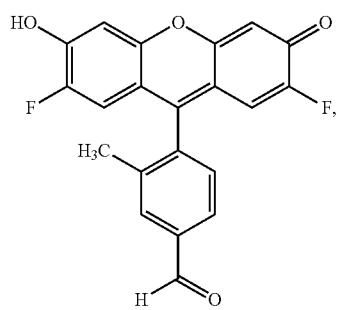

or a salt thereof; and
the oxidized compound of Formula I is (ii) or (iii):

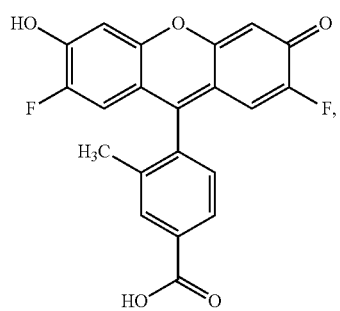

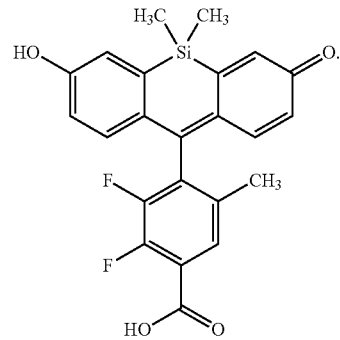

or a salt thereof.

In some embodiments, the control comprises a control cell and Ctrl-AlDeSense or Ctrl-AlDeSense AM, or a salt thereof.

In other embodiments, the fluorescent intensity of the contacted cell is 2-40 times more intense than the control cell when ALDH-1A1 is present in the contacted cell and the control cell.

This disclosure additionally provides compounds described herein for use in monitoring cancer stem cell differentiation in a cell culture, or for use in identifying a cancer stem cell in a cell culture. In some embodiments, the disclosed compounds are for use in ex-vivo or in-vivo imaging of ALDH-1A1 activity in a cancer stem cell.

In various embodiments of the disclosed Formulas and compounds, the salts of the said Formulas and compounds may also be formed in-vitro or in-vivo, and the counter-ion of the salt may be any naturally occurring cationic species found in a biological system (including cancer cells or cancer stem cells), such as, but not limited to sodium ion, potassium ion, or calcium ion.

This disclosure additionally provides a method for imaging a cell comprising:

a) contacting a cell and a fluorescent probe of Formula I:

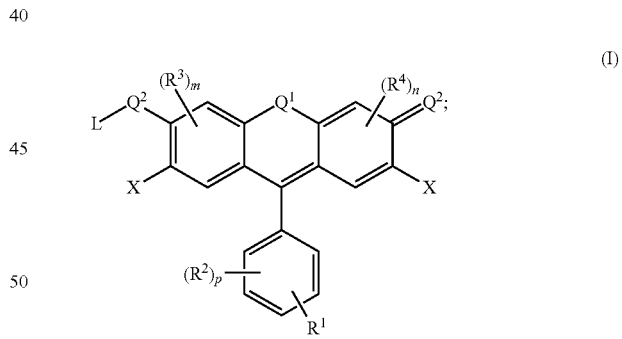

or a salt thereof, wherein $Q^1$ is O, S, $C(R^4)_2$, $Si(R^4)_2$, or P(=O)$R^4$, wherein each $R^4$ is independently H, —$(C_1-C_6)$alkyl, or —O$(C_1-C_6)$alkyl;

each $Q^2$ is independently O, S or $NR^B$, wherein $R^B$ is H or —$(C_1-C_6)$alkyl;

L is H or an enzymatically labile group;

each X is independently H, halo, nitro, or alkylsulfonyl;

$R^1$ is —CH(=O), —C(=O)$(C_1-C_6)$alkyl, or —CH$(OR)_2$ wherein each R is independently H, —$(C_1-C_6)$alkyl, or two R taken together form an acetal;

$R^2$, $R^3$ and $R^4$ are each independently halo, OH, —$(C_1-C_6)$alkyl, —O$(C_1-C_6)$alkyl, nitro, or phenyl wherein —$(C_1-C_6)$alkyl and phenyl are optionally substituted with 1-5 substituents;

m and n are independently 0-2; and
p is 0-4; and
b) determining the fluorescent intensity in the contacted cell;
wherein aldehyde dehydrogenase-$_1$A$_1$ (ALDH$_1$A$_1$), when present in the contacted cell, oxidizes the aldehyde moiety R$^1$ is —CH(=O) of Formula I to a carboxyl moiety; and
wherein the fluorescent intensity of the contacted cell is modulated by the amount of ALDH$_1$A$_1$ present in the cell, thereby providing an image of aldehyde dehydrogenase activity in the contacted cell.

In various additional embodiments, the methods disclosed comprises contacting the cell and a control compound of Formula I wherein R$^1$ is —C(=O)(C$_1$-C$_6$)alkyl. In other embodiments, the method comprises determining the difference in fluorescent intensity in the contacted cell relative to the control.

In further embodiments, an enzyme in the cell cleaves the enzymatically labile group L of Formula I to release a phenolic compound from the fluorescent probe, and ALDH$_1$A$_1$, when present in the contacted cell, oxidizes the aldehyde moiety R$^1$ is —CH(=O) of the phenolic compound to a carboxyl moiety; wherein the fluorescent intensity of the contacted cell is modulated by the amount of ALDH$_1$A$_1$ present in the cell, thereby providing an image of aldehyde dehydrogenase activity in the contacted cell.

Surveillance of Cancer Stem Cell Plasticity Using an Isoform-Selective Fluorescent Probe for Aldehyde Dehydrogenase 1A1

Herein, we present AlDeSense, a turn-on fluorescent probe for aldehyde dehydrogenase 1A1 (ALDH1A1) and Ctrl-AlDeSense, a matching non-responsive reagent. Although ALDH1A1 contributes to the detoxification of reactive aldehydes, it is also associated with stemness and is highly elevated in CSCs. AlDeSense exhibits a 20-fold fluorescent enhancement when treated with ALDH1A1. Moreover, we established that AlDeSense is selective against a panel of common ALDH isoforms and exhibits exquisite chemostability against a collection of biologically relevant species. Through the application of surface marker antibody staining, tumorsphere assays, and assessment of tumorigenicity, we demonstrate that cells exhibiting high AlDeSense signal intensity have properties of CSCs. Using these probes in tandem we have identified CSCs at the cellular level via flow cytometry and confocal imaging, as well as monitored their states in animal models.

Results

Synthesis of AlDeSense.

The synthesis of AlDeSense involved DIBAL reduction of methyl 4-bromo-3-methylbenzoate to afford the corresponding benzyl alcohol 1, which was protected with tert-butyldimethylsilyl chloride to give 2 in 93% yield over two steps. Lithium halogen exchange enabled coupling to MEM-protected difluoroxanthone giving the Pennsylvania Green intermediate 3 in 48% yield after acid mediated global deprotection. IBX oxidation of the benzyl alcohol then afforded AlDeSense in 79% yield. Preparation of AlDeSense AM, a cell permeable derivative, could be achieved via alkylation of AlDeSense with bromomethyl acetate in 60% yield (Scheme 1). Once internalized, intracellular esterases can hydrolyze the AM group to afford the parent AlDeSense reagent. The synthesis of Ctrl-AlDeSense involved similar chemistry and the details can be found in the supplemental information document. Of note, both AlDeSense and AlDeSense AM will herein be referred to as AlDeSense for simplicity. AM protected versions were utilized for all cellular and animal studies.

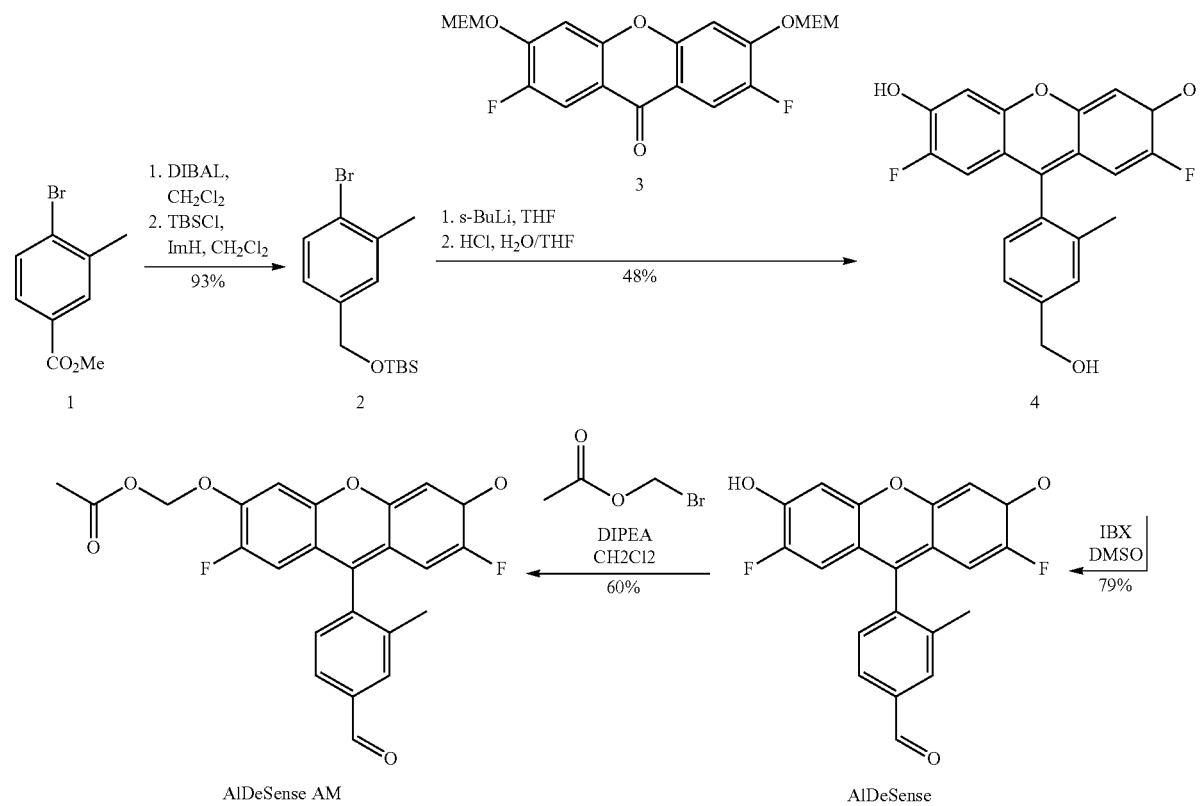

Scheme 1. Synthesis of AlDeSense and AlDeSense AM.

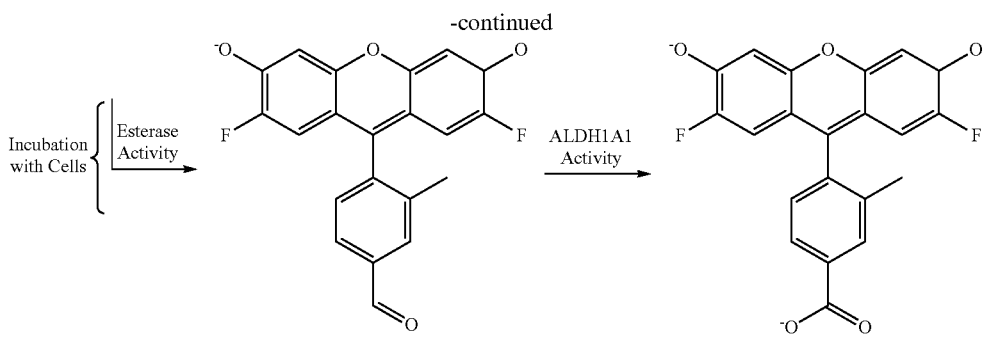

Figure 1:
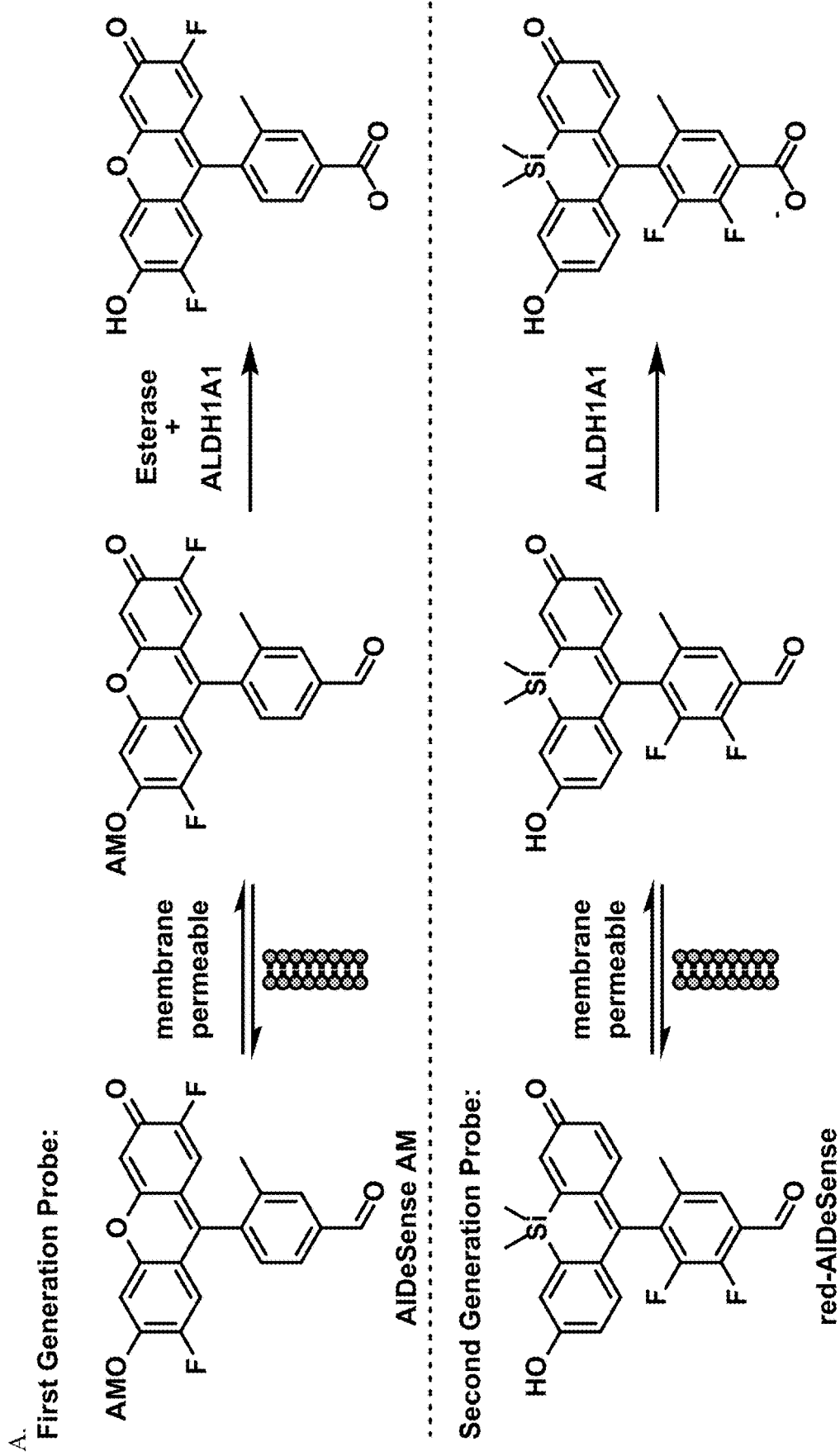
FIG. 1. (a) Comparison of the enzymatic requirements for accumulation and fluorescent turn on of AlDeSense AM and red-AlDeSense. (b) Fluorescence spectra of AlDeSense upon incubation with recombinant ALDH1A1 at room temperature. Inset shows fluorescence increase over time under the same conditions. (c) Comparison of fluorescence signal from ALDH1A1 reacting with the following: AlDeSense, AlDeSense with additional inhibition with DEAB (100 nM), and Ctrl-AlDeSense. (e) Normalized fluorescence turn-on of AlDeSense after incubation with 20 units of each ALDH isoform for 30 min at room temperature. Units are defined as 1 μmol substrate turned over/μmol enzyme/min. (e) Response of AlDeSense to various reactive oxygen species, biological thiols, and amines at concentrations of 100 μM (GSH was tested at 1 mM). For all assays, AlDeSense was used at 1 μM final concentration.
Figure 1:
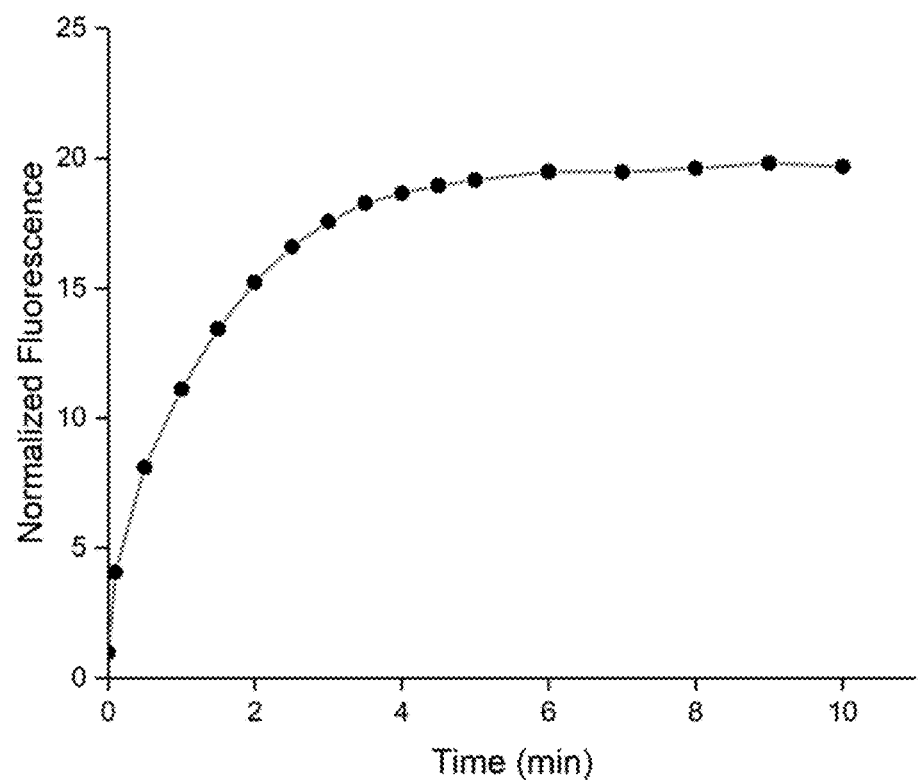
Figure 1:
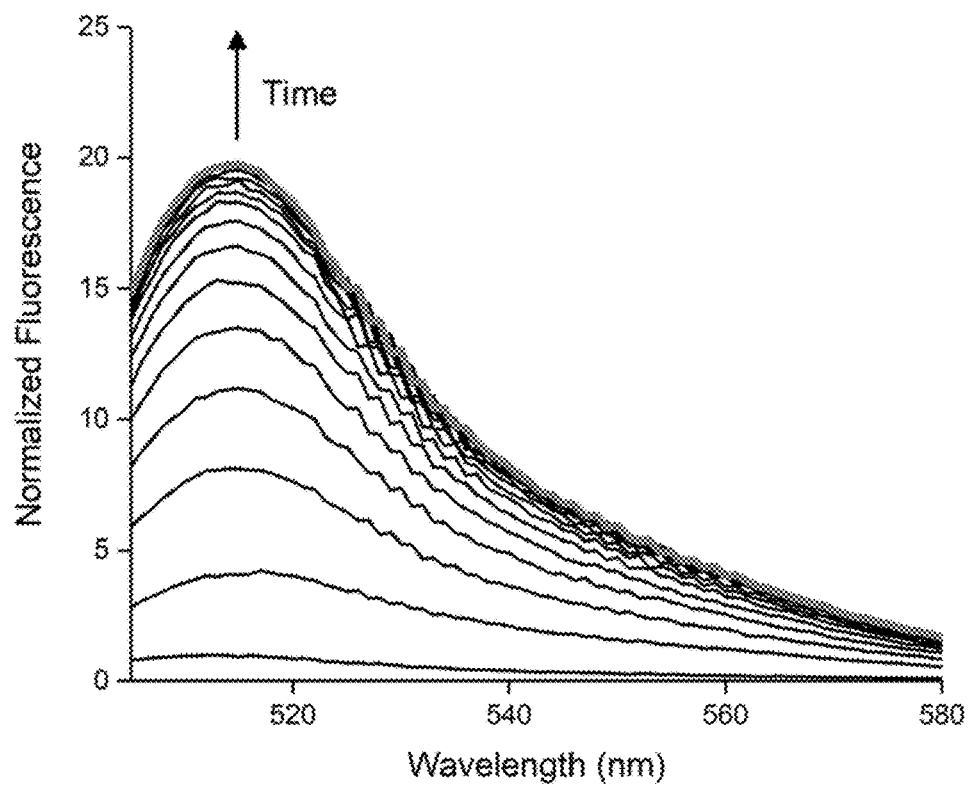
Figure 1:
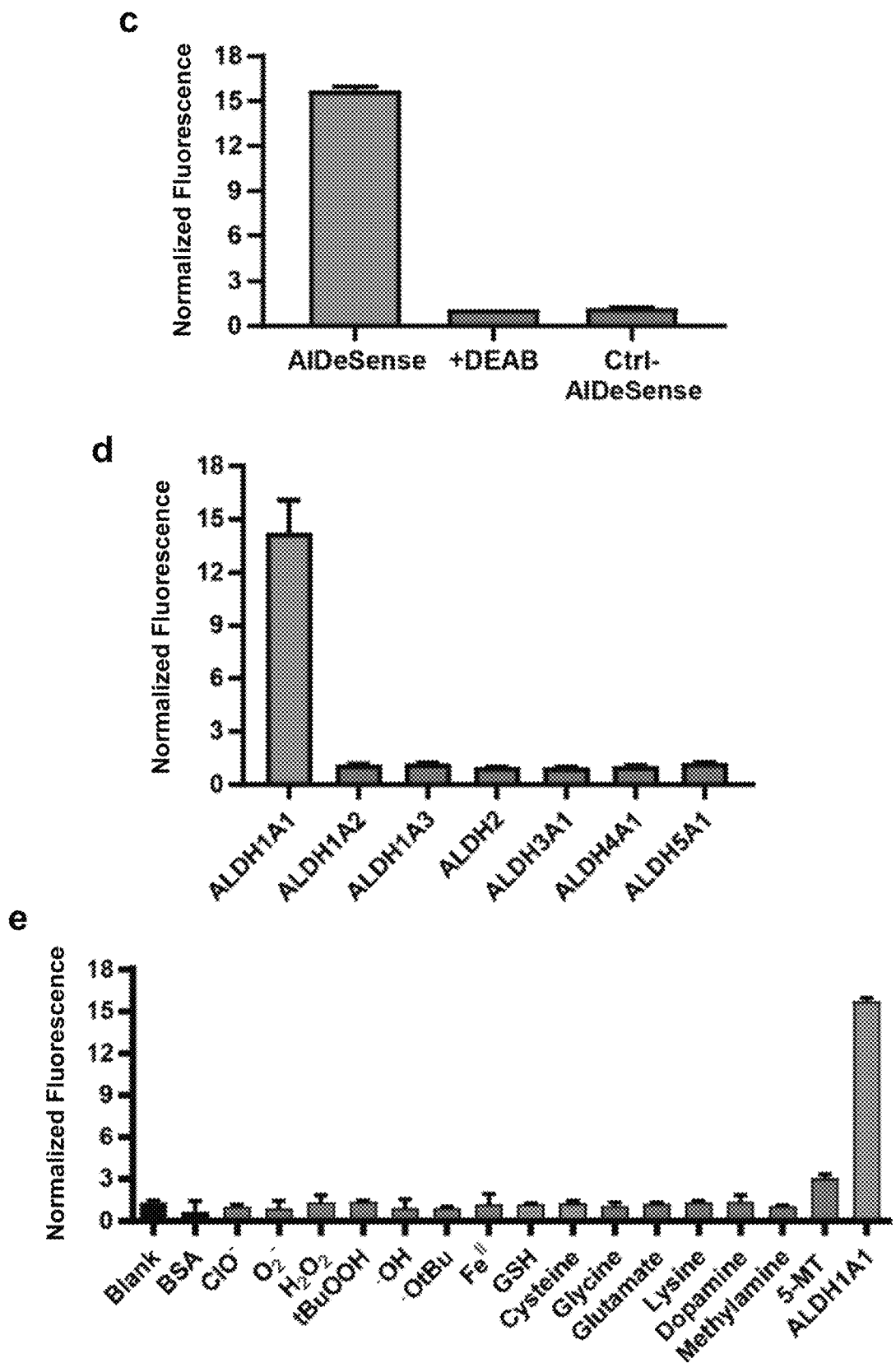
Figure 9:
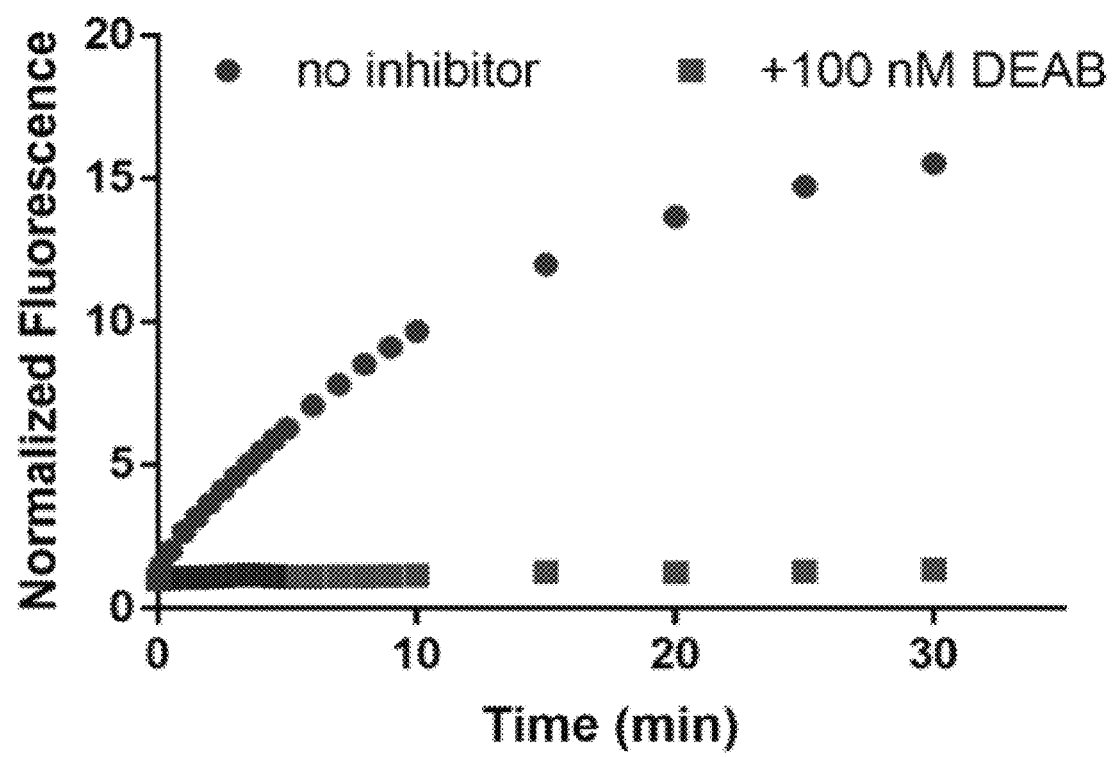
FIG. 9. Comparison of normalized fluorescence turn-on of 1 µM AlDeSense incubated with 100 nM ALDH1A1 and 1 µM AlDeSense incubated with 100 nM ALDH1A1 supplemented with 100 nM 4-diethylaminobenzaldehyde (DEAB). Both reactions were done with 2.5 mM $NAD^+$ and 50 mM TEA (pH 7.4) at room temperature.
Figure 10:
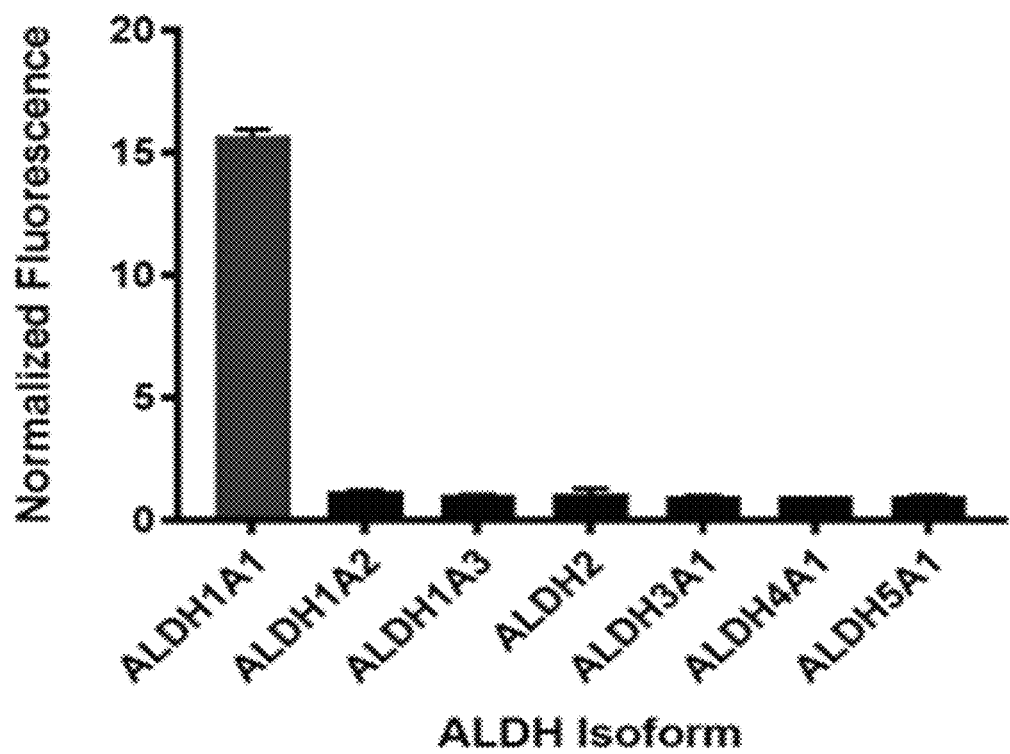
FIG. 10. Normalized fluorescence turn-on of AlDeSense after incubation with 100 nM concentration of each ALDH isoform for 30 min at room temperature. Measurements were performed in triplicate; error bars are ±SD.
Figure 11:
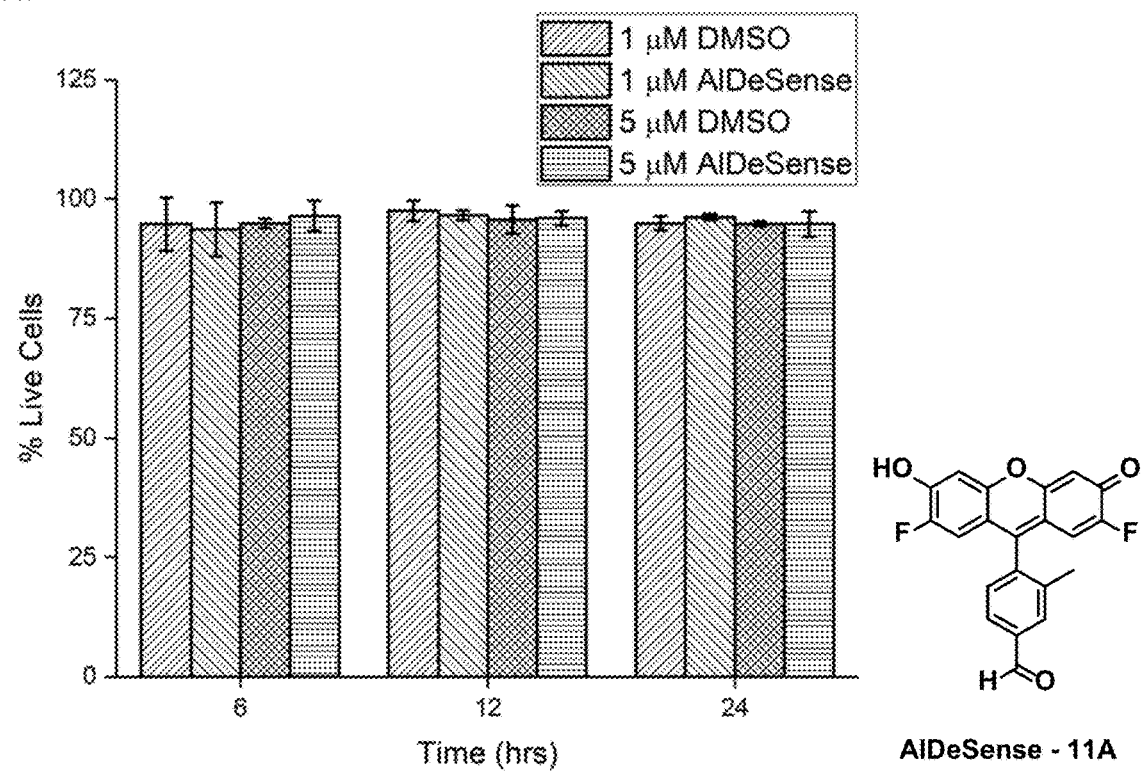
FIG. 11. Trypan blue cytotoxicity assay for (a) AlDeSense and (b) Ctrl-AlDeSense in K562 cells over 6, 12, and 24 hours. Each sample was matched with a DMSO vehicle control and done in triplicate. Error bars are ±SD.
Figure 11:
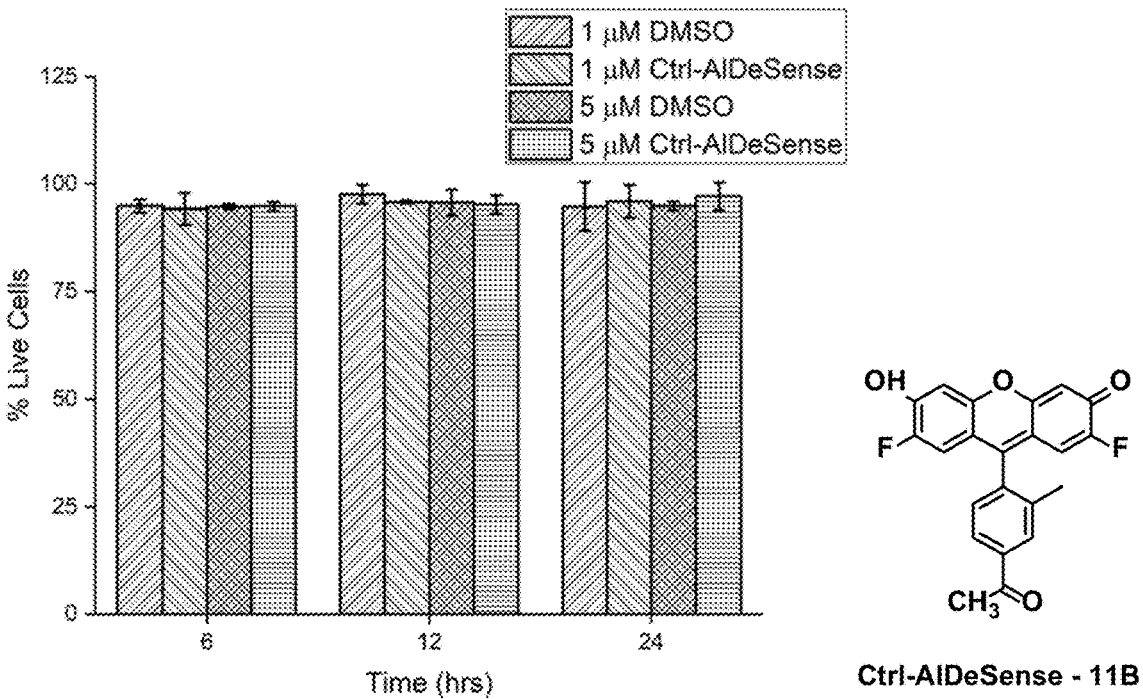
Figure 12:
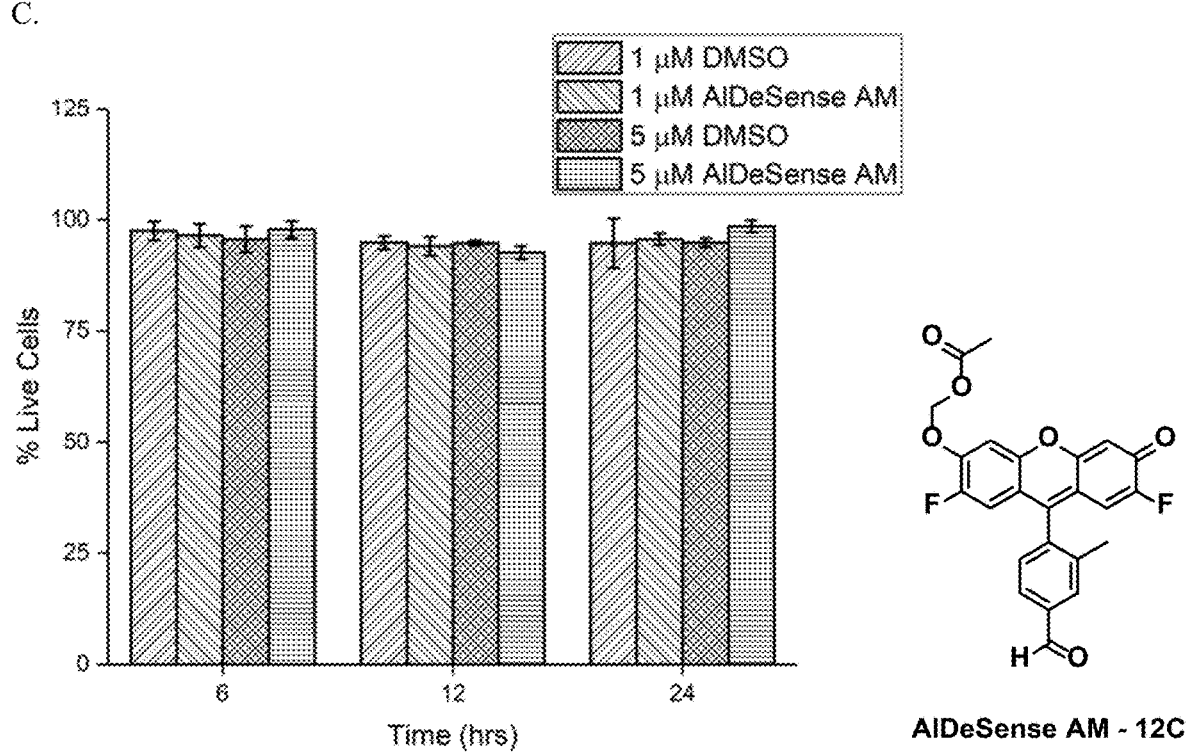
FIG. 12. Trypan blue cytotoxicity assay for (c) AlDeSense AM, (d) Ctrl-AlDeSense AM, and (e) oxidized AlDeSense (the turned-over product) in K562 cells over 6, 12, and 24 hours. Each sample was matched with a DMSO vehicle control and done in triplicate. Error bars are ±SD.
Figure 12:
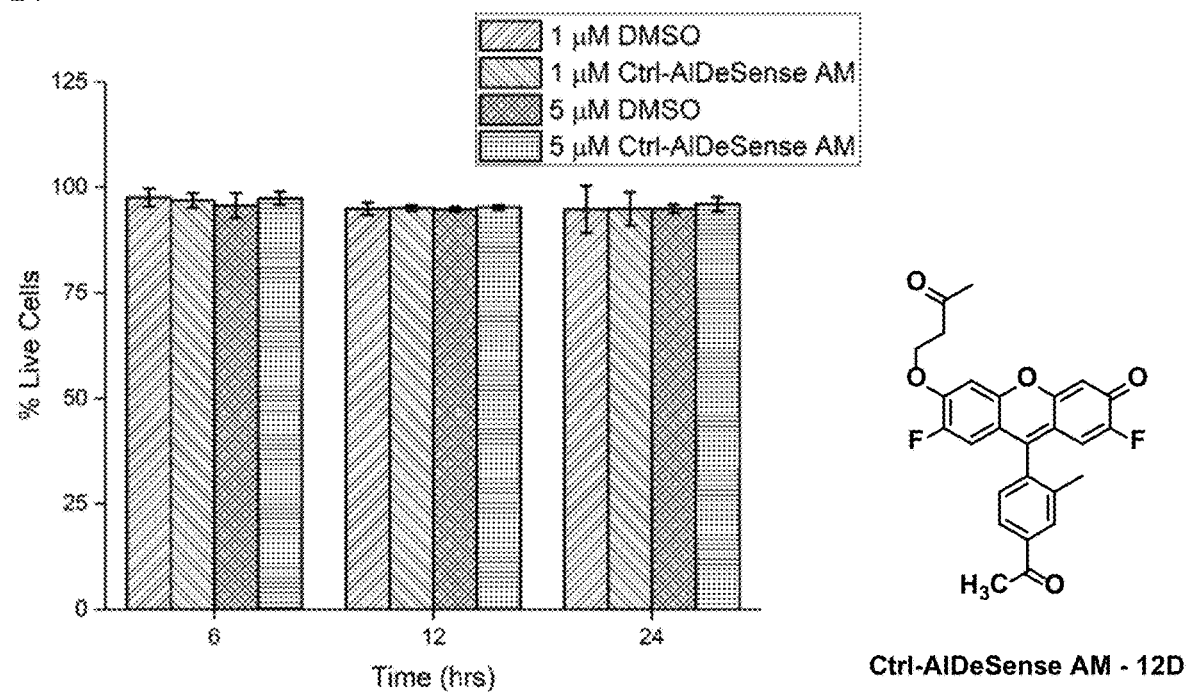
Figure 12:
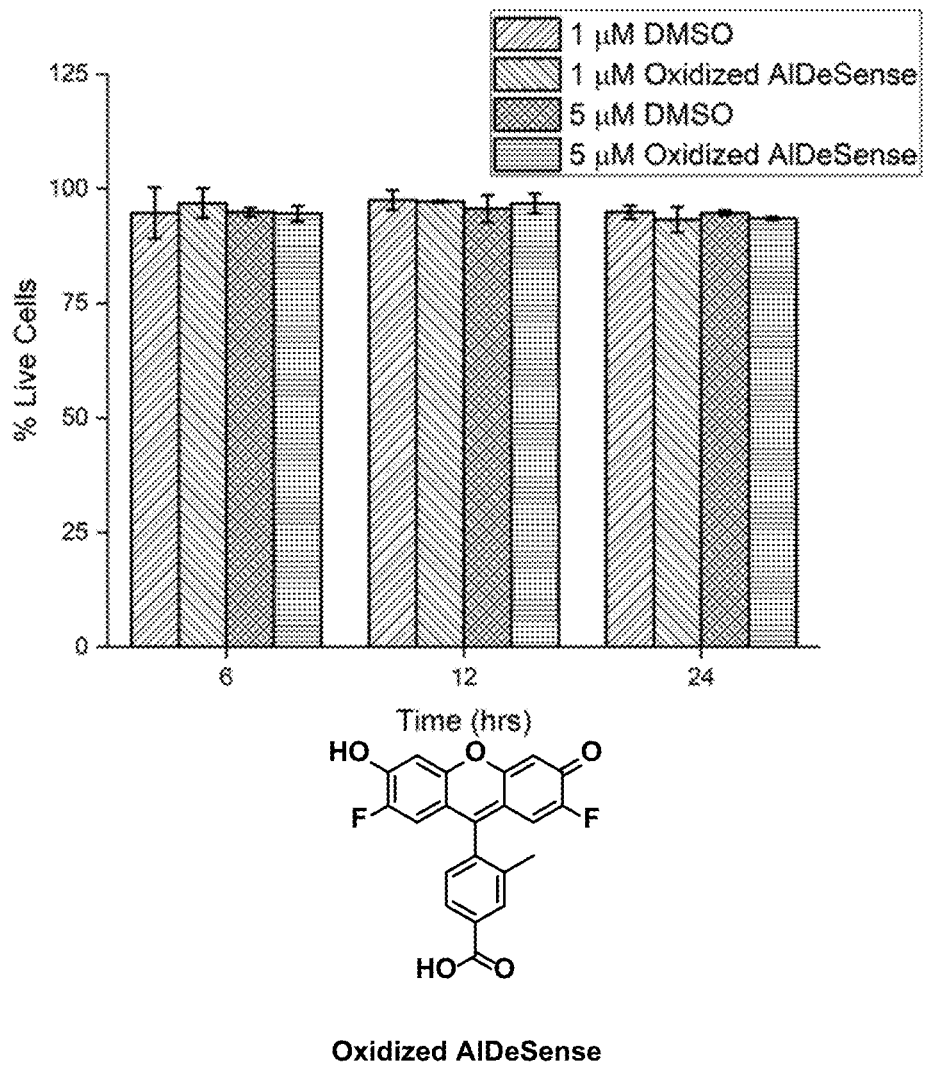
Figure 13:
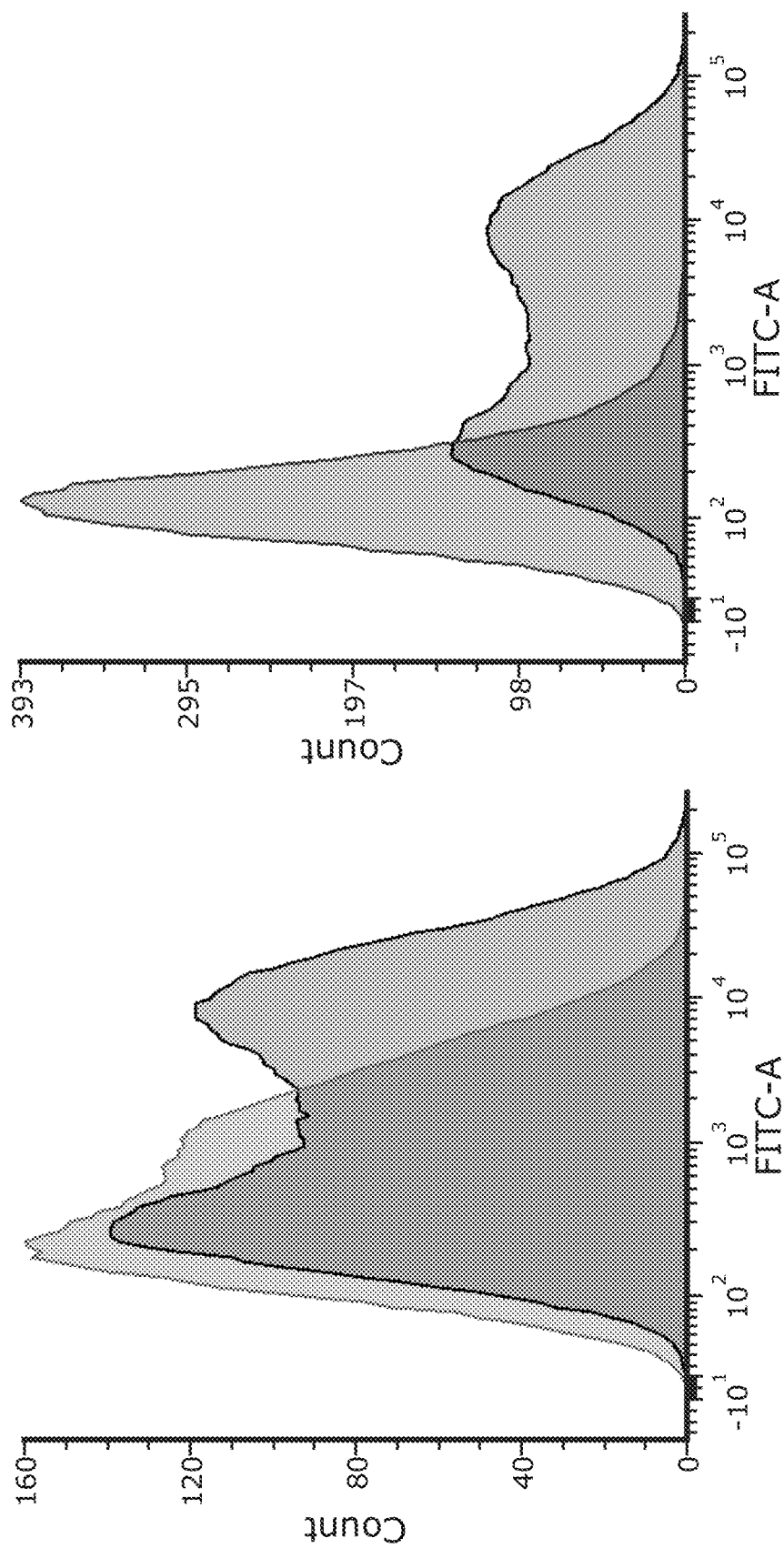
FIG. 13. Flow cytometry analysis of K562 cells stained with 2 µM AlDeSense (right-skewed curve in graphs of both panes), 2 µM Ctrl-AlDeSense (left-skewed curve in graph of right pane) and 2 µM AlDeSense after inhibition with 25 µM disulfiram (left-skewed curve in graph of left pane). Inhibition was accomplished by preincubating the cells in 25 µM disulfiram for 60 min before staining with dye for 30 min at room temperature. Data analyzed on FCS Express 6.04.

In vitro characterization. With AlDeSense in hand, we first evaluated its response to purified ALDH1A1. Prior to activation, AlDeSense was weakly fluorescent ($\Phi_F=0.04$); however, addition of ALDH1A1 resulted in a robust ~20-fold fluorescent enhancement (FIG. 1d). Inhibition of ALDH1A1 with DEAB completely abolished the turn-on response, and the resulting fluorescent signal was comparable to that of Ctrl-AlDeSense (FIG. 1e, FIG. 9). Next, we screened for potential cross-reactivity against a panel of the most common ALDH isoforms and found that only ALDH1A1 led to probe activation. (Figure if, FIG. 10). To ensure that AlDeSense is only activated by ALDH1A1 when in cells, we assessed potential off-target responses against various biologically relevant analytes. Although aldehyde groups are prone to oxidation, we did not observe any oxidized fluorescent products when screened against a panel of reactive oxygen species (FIG. 1g). Similarly, when AlDeSense was incubated with various thiols and amines we did not detect formation of fluorescent hemithioacetal and Schiff base products, respectively (FIG. 1g). We also established that AlDeSense, its turned-over product, and the control reagent are non-toxic using standard cell viability assays (FIG. 11). Moreover, LC-MS shows that AM deprotection, as well as ALDH1A1-catalyzed oxidation occurs upon cell uptake (FIG. 12). Together, these key experiments indicate that AlDeSense is suitable for detecting ALDH1A1 activity in living systems.

Figure 2:
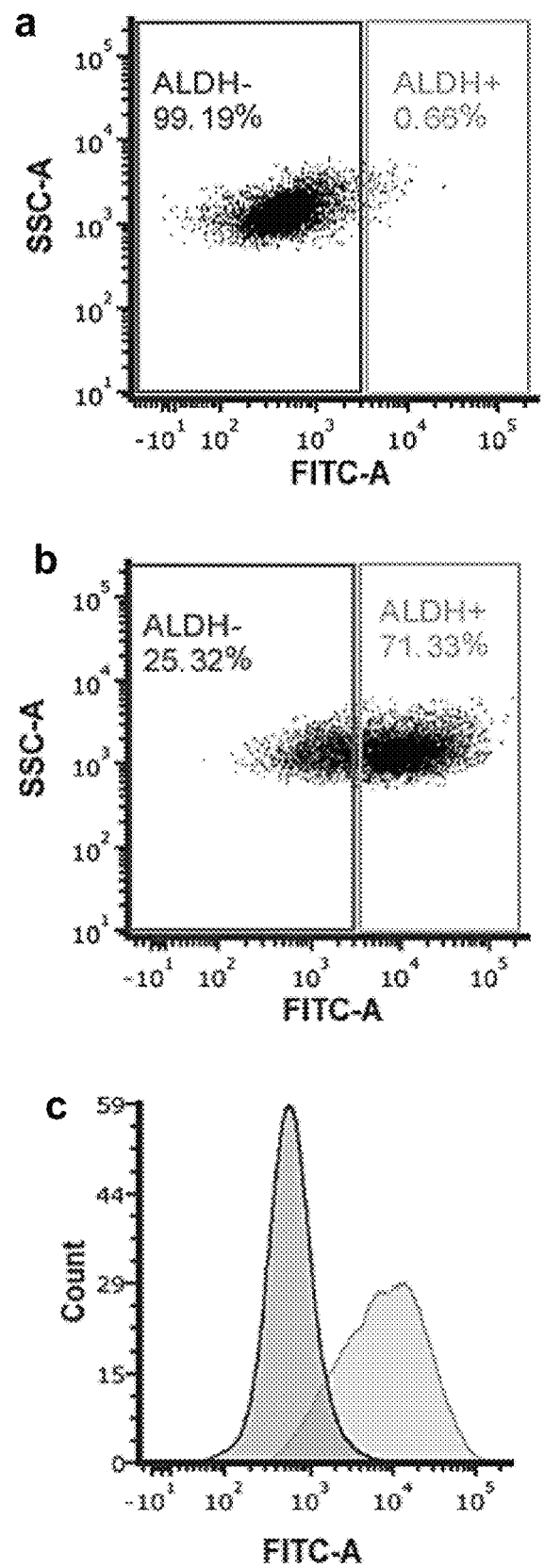
FIG. 2. Application of AlDeSense and Ctrl-AlDeSense in live K562 cells. Flow cytometry analysis of K562 cells stained with (a) Ctrl-AlDeSense (1.5 μM) or (b) AlDeSense (1.5 μM). (c) Histographic profiles of (a) and (b) shown in left- and right-panes of graphs, respectively. Confocal images of K562 cells stained with (d) AlDeSense or (e) Ctrl-AlDeSense both at 2 μM. Scale bars are 100 μm. (f) Percentage of total cells showing fluorescence using each of these stains. (Error bars are ±SD, n=9, unpaired t-test with Welch's correction.) (g) Knockdown of ALDH1A1 using siRNA showed an ablation of signal compared to cells treated with a scrambled siRNA as a negative control (Error bars are SD, n=15, unpaired t-test with Welch's correction).
Figure 2:
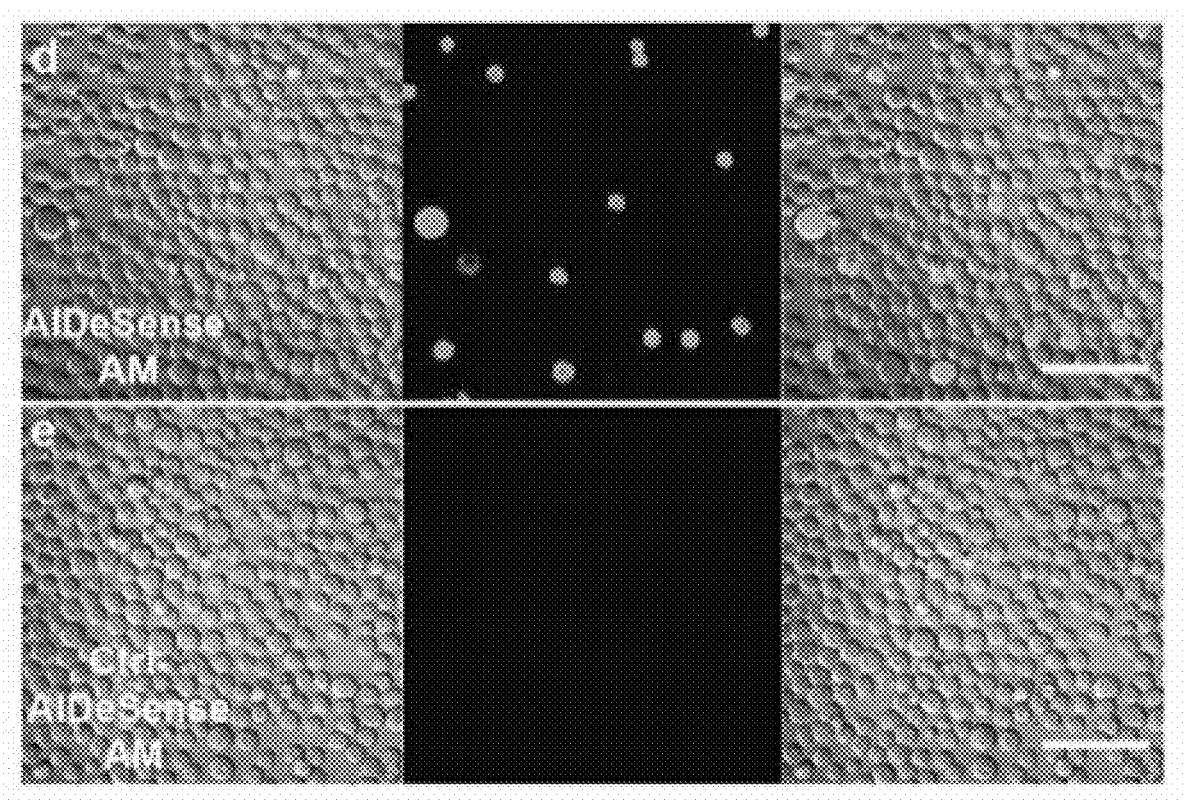
Figure 3:
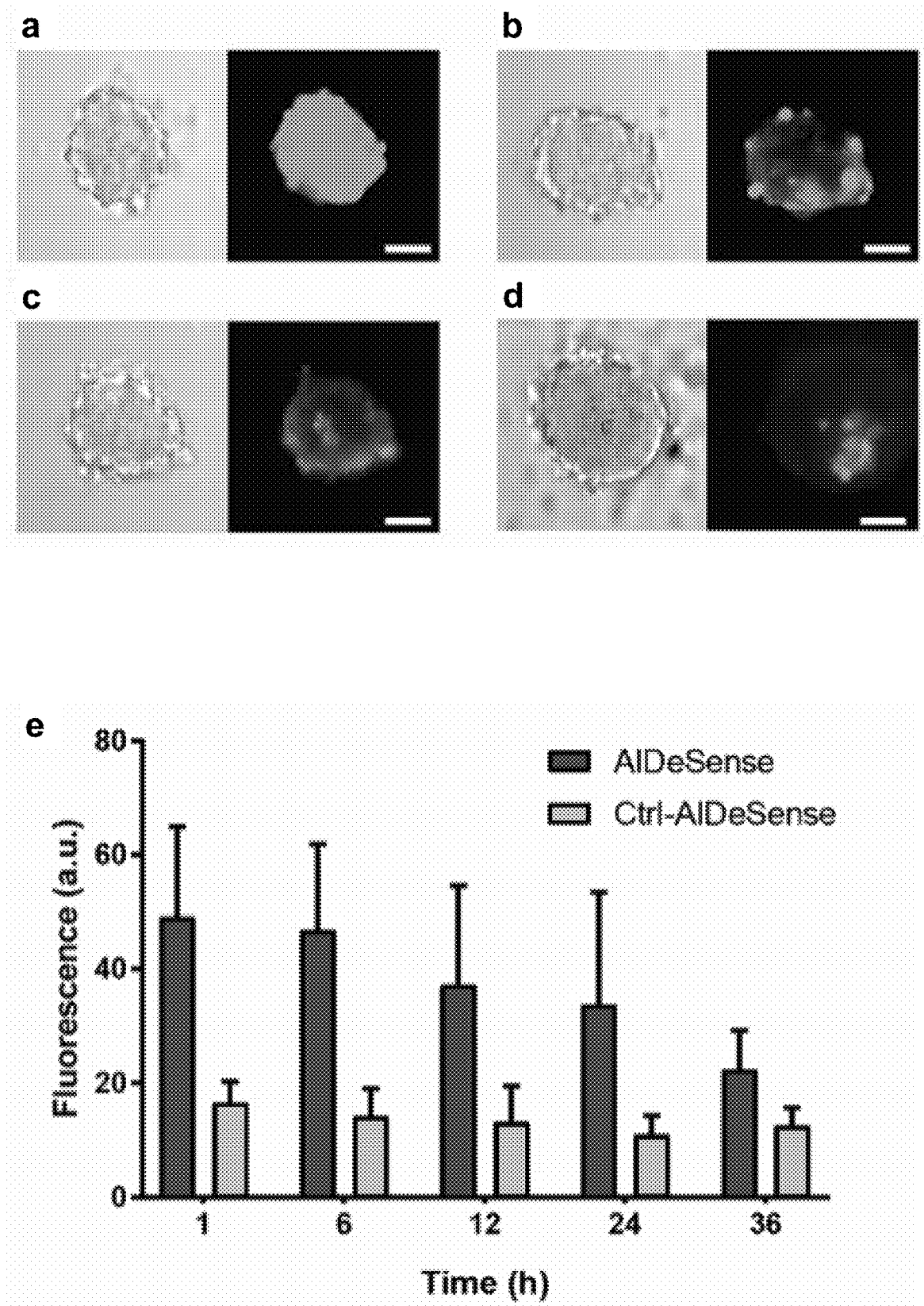
FIG. 3. Imaging of enriched-CSC cell cultures. Representative brightfield and fluorescence images of mammospheres stained with (a) AlDeSense and (b) Ctrl-AlDeSense. Representative brightfield and fluorescence images of mammospheres after 36 h in normal cell culture media, stained with (c) AlDeSense and (d) Ctrl-AlDeSense. e) Mean fluorescence signals from mammospheres for both dyes at several time points throughout differentiation. Error bars are ±SD, n≥7. Confocal imaging of patterned (e-CSC) B16F0 melanoma versus non-patterned (non-CSC) melanoma using AlDeSense (AS) and Ctrl-AlDeSense (Ctrl). Representative composite brightfield and fluorescence images of (f) e-CSCs stained with AlDeSense, (g) e-CSCs stained with Ctrl-AlDeSense, (h) non-CSCs stained with AlDeSense, and (i) non-CSCs stained with Ctrl-AlDeSense. Quantification of the fluorescence intensity (j). For each condition, n≥21 μmages were taken across three different sample preparations. Error bars are ±SD. Scale bars are 50 μm.
Figure 3:
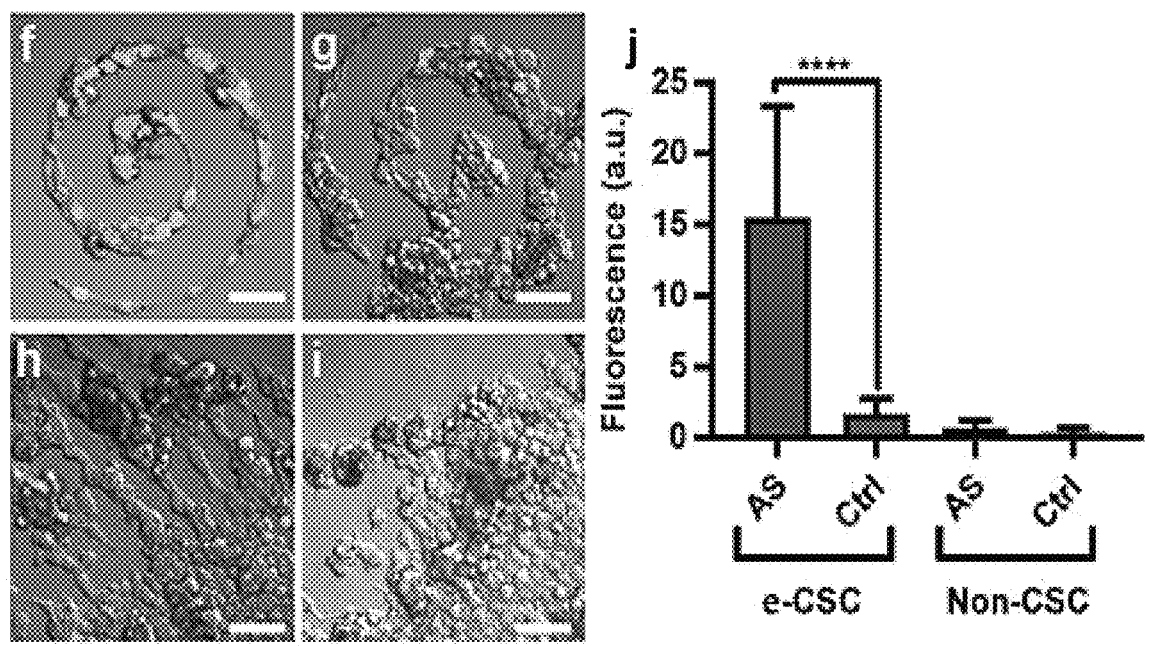
Figure 14:
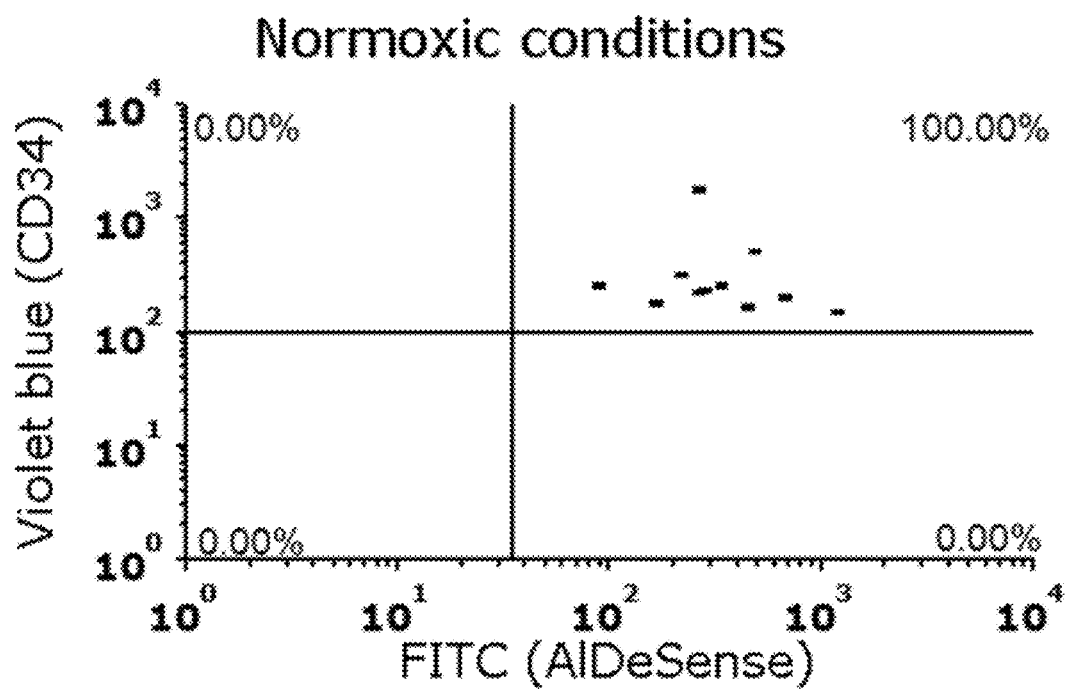
FIG. 14. Comparison of CSC-like populations within wild-type K562 cells using flow cytometry analysis of staining with AlDeSense, CD34, and CD38. To locate these populations, the live singlets from the bulk cell population were gated for cells with higher signal compared to Ctrl-AlDeSense as well as cells that were CD38–. (a) The remaining cells were CD34+, CD38– and AlDeSense+, the expected staining pattern for leukemic stem cells. (b) Growing cells under hypoxic conditions increases the population of CSC-like cells by 1.6-fold. Data was collected and averaged over duplicate runs.
Figure 14:
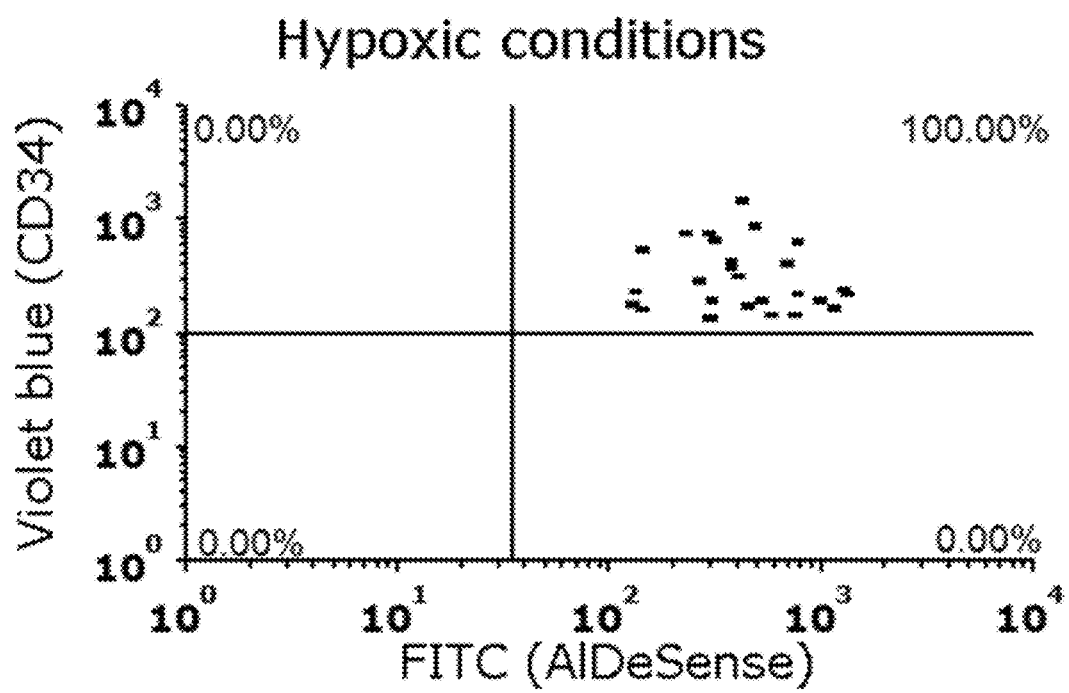
Figure 15:
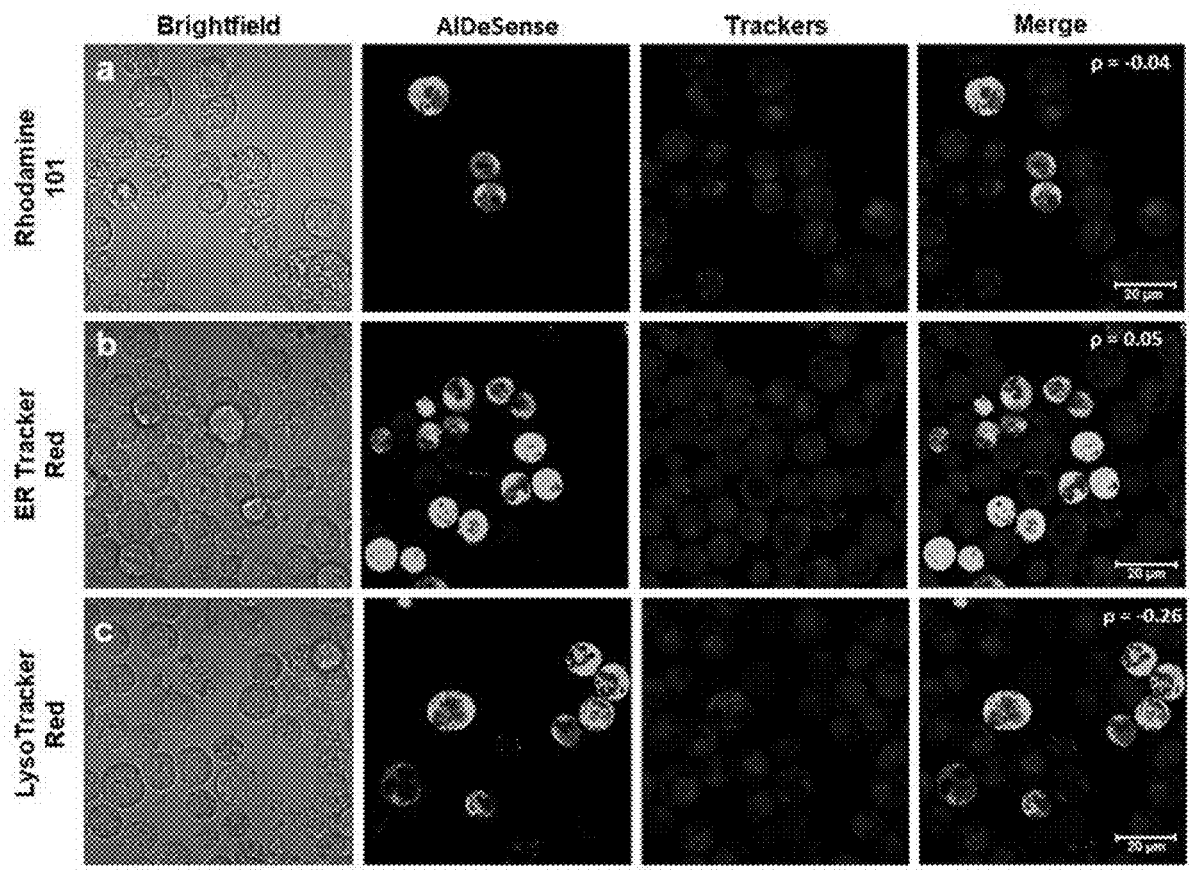
FIG. 15. Colocalization study of AlDeSense with various organelle trackers in K562 cells. (a) Colocalization of AlDeSense with Rhodamine 101 methyl ester, (b) colocalization of AlDeSense with ER Tracker Red, and (c) colocalization of AlDeSense with LysoTracker Red. Pearson's R coefficients (p) are averages of 18 measurements over three images. Scale bar is 20 µm.
Figure 16:
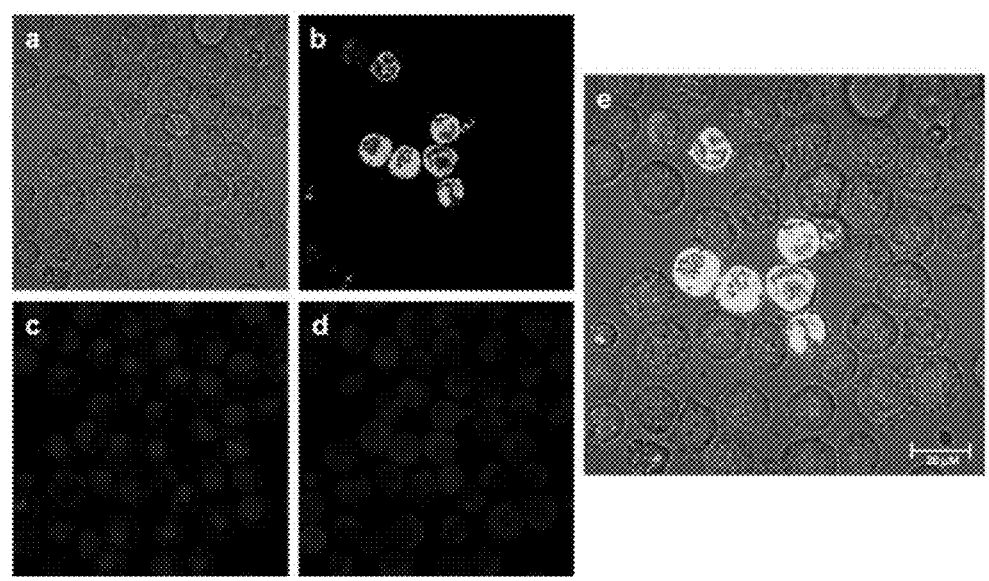
FIG. 16. Colocalization study of AlDeSense including nuclear stain in K562 cells. Signals from (a) brightfield, (b) AlDeSense, (c) LysoTracker Red, and (d) Hoescht 33342, as well as (e) merged image of all four signals. Scale bar is 20 µm.
Figure 17:
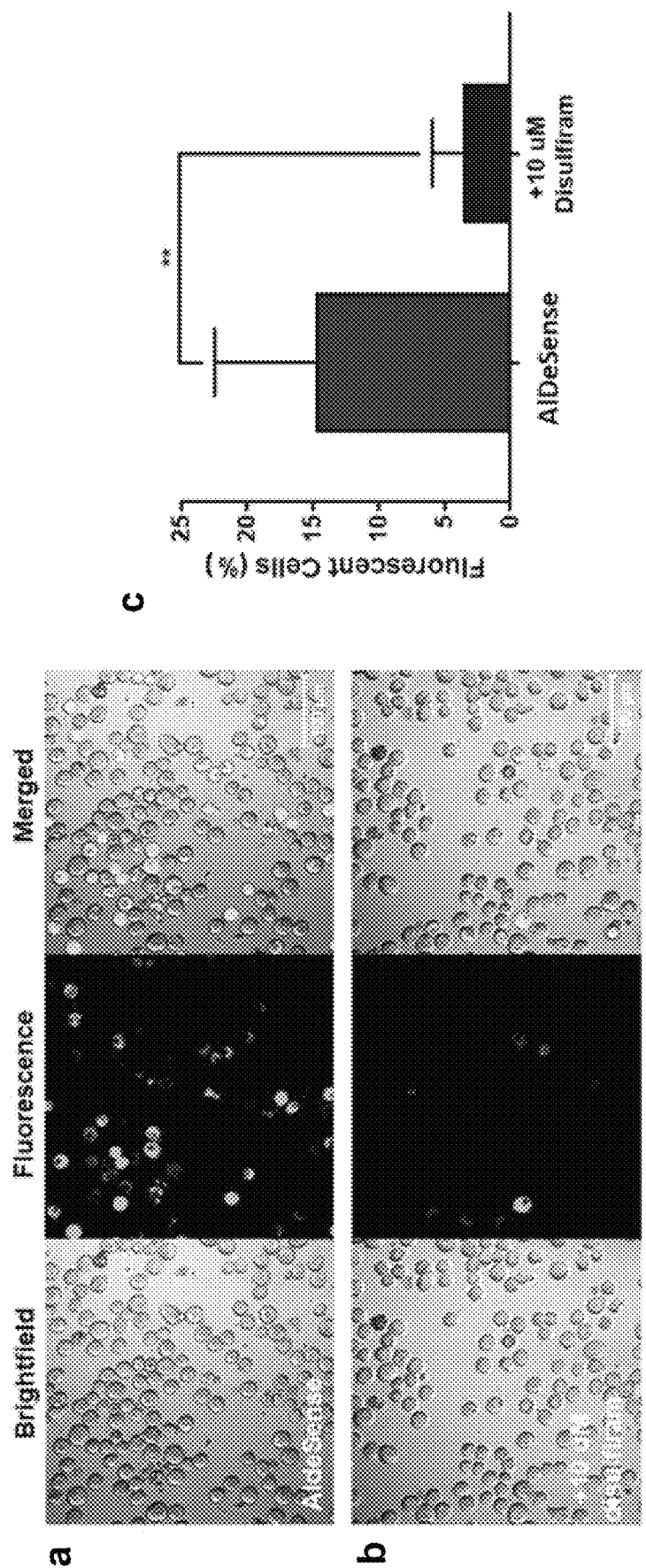
FIG. 17. Representative images of K562 cells stained with (a) AlDeSense after 60 min preincubation with vehicle or (b) AlDeSense after 60 min preincubation with 10 µM disulfiram in PBS. Scale bars are 100 µm. (c) Percentage of total cells showing fluorescence after both vehicle and disulfiram preincubation (Error bars±SD, n=9, unpaired t-test with Welch's correction).
Figure 18:
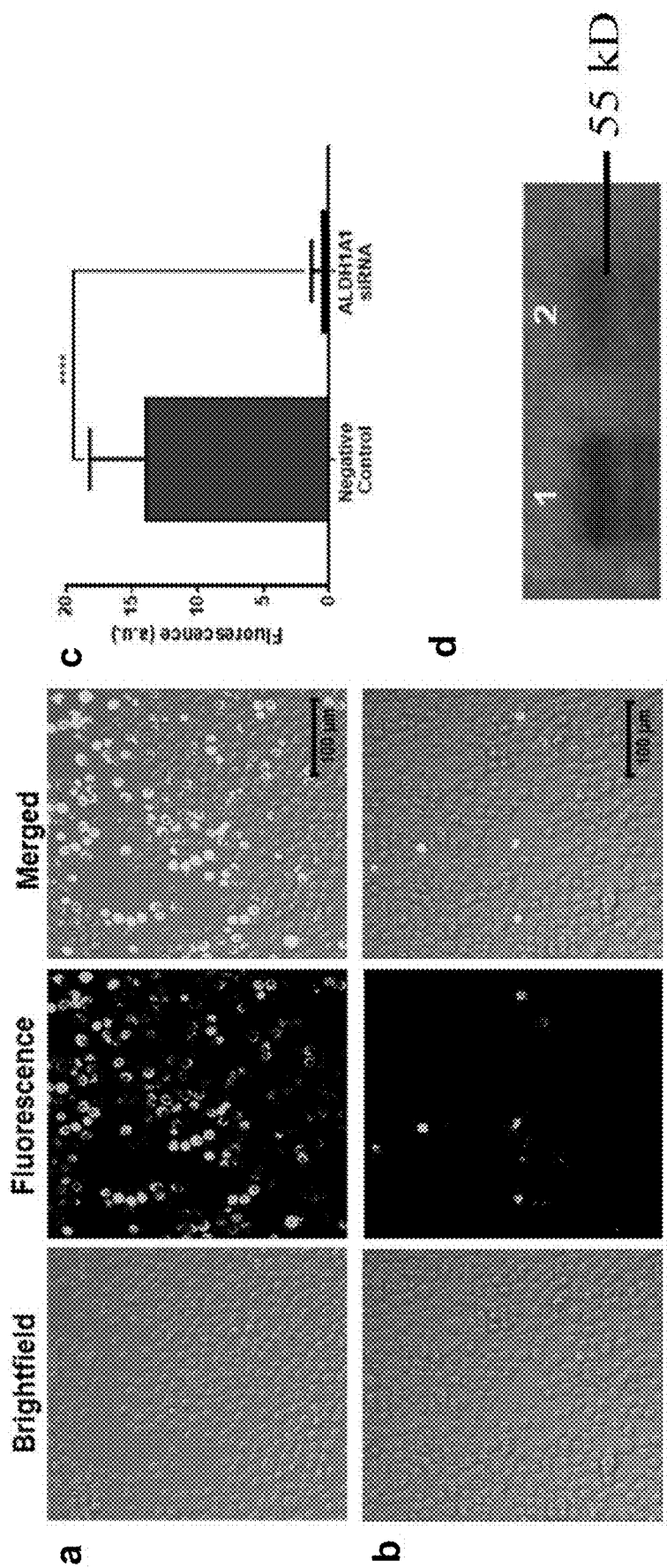
FIG. 18. Representative images of K562 cells treated with (a) scrambled negative control siRNA or (b) siRNA specific for ALDH1A1. (c) Mean fluorescence of cells treated with scrambled negative control siRNA or ALDH1A1 siRNA. (Error bars are ±SD, n=15, unpaired t-test with Welch's correction). (d) Western blot analysis of K562 cells treated with (1) scrambled siRNA or (2) siRNA specific for ALDH1A1. A band of approximately 55 kDa was detected (predicted molecular weight: 55 kDa). Band of sample treated with scrambled siRNA has 1.6-fold higher intensity than the band treated with ALDH1A1 specific siRNA.
Figure 19:
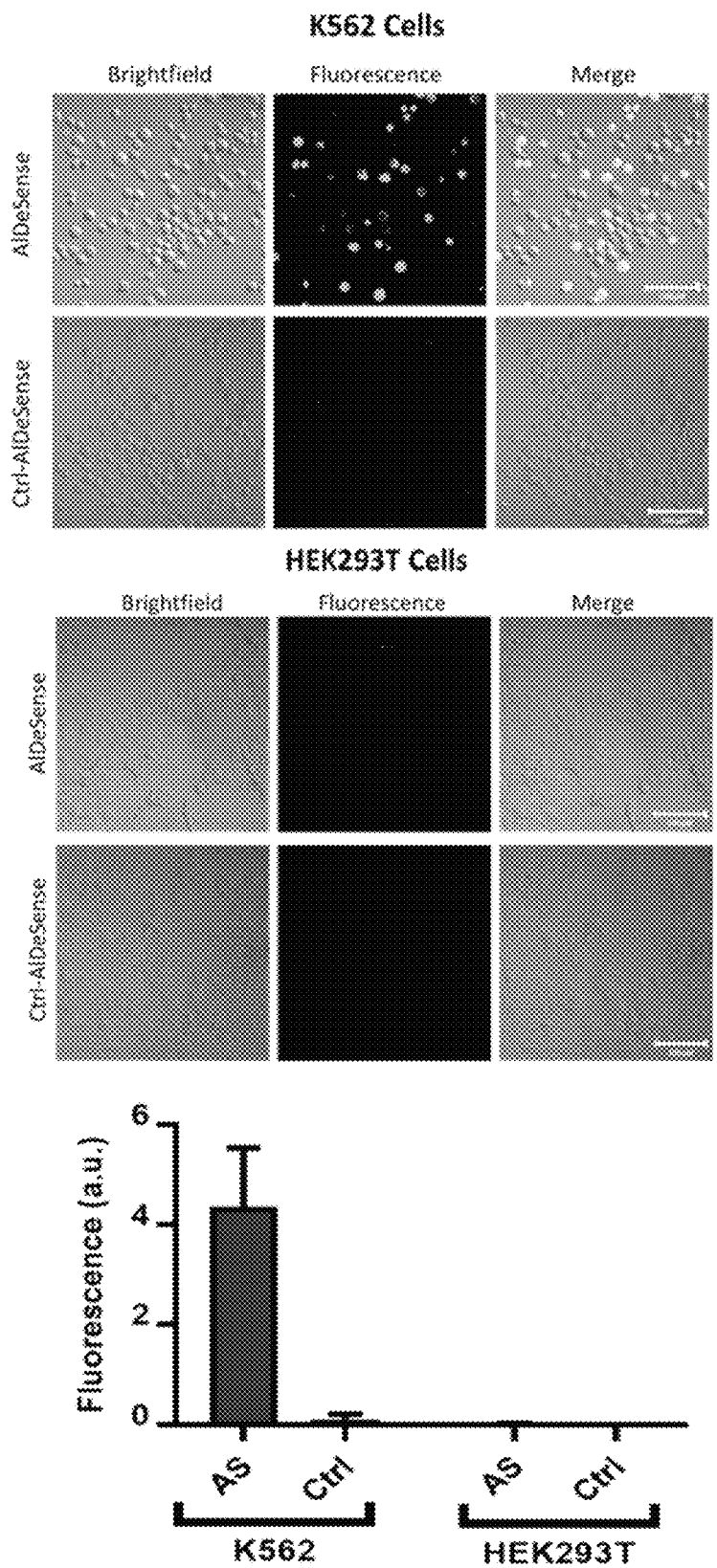
FIG. 19. Comparison of AlDeSense signal in ALDH1A1+ cells (K562) and ALDH1A1-cells (HEK293T). Representative images of (a) AlDeSense signal in K562 cells, (b) Ctrl-AldeSense signal in K562 cells, (c) AlDeSense signal in HEK293T cells, and (d) Ctrl-AlDeSense signal in HEK293T cells, as well as (e) quantification of average fluorescence signal from these images (n=5). All imaging was done after a 30 min incubation with 2 µM AlDeSense or Ctrl-AlDeSense using 1% laser power (488 nm) and 584.5 detector gain. Scale bars are 100 µM.
Figure 20:
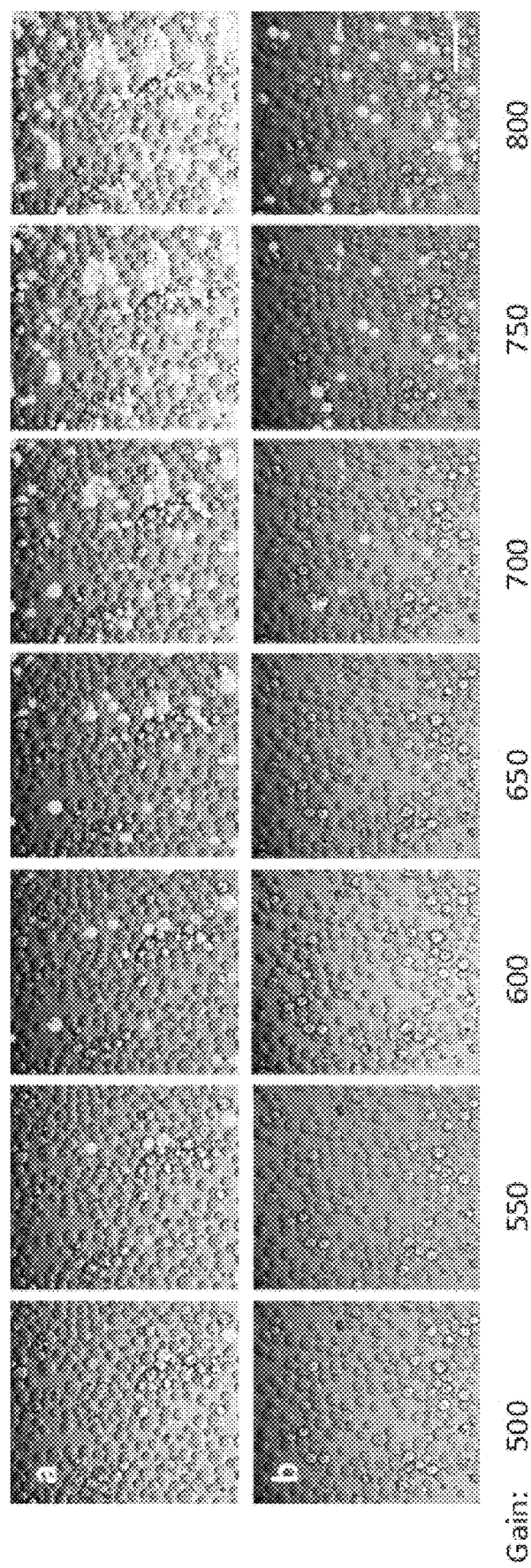
FIG. 20. Confocal imaging of K562 cells stained with (a) AlDeSense and (b) Ctrl-AlDeSense for 30 min at room temperature. Dyes were excited using a 488 nm laser at 1% power. All parameters were held constant except for the gain of the fluorescent channel. From left to right, the gains for both a and b were increased as noted below the image. The same field of view was maintained for each dye as the fluorescent gains were increased.
Figure 21:
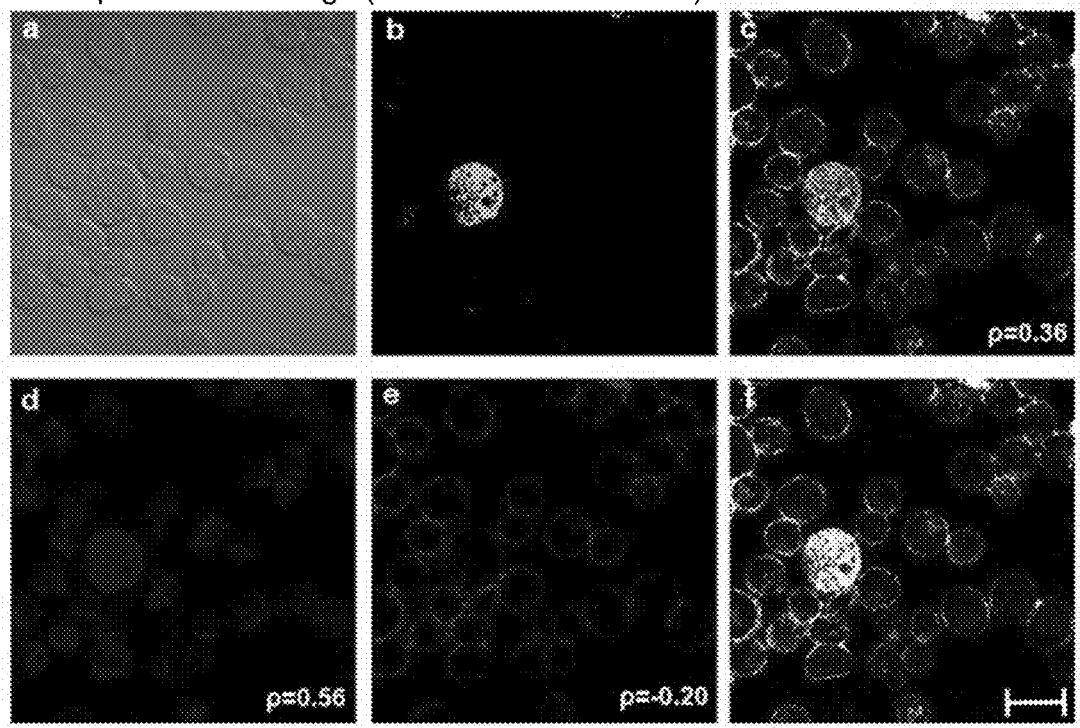
FIG. 21. Three representative images (I-III) of the colocalization of AlDeSense with cancer stem cell marker antibodies conjugated to fluorescent dyes: (a) bright field view, (b) AlDeSense, (c) CD133/1(AC133)-PE, (d) CD34-
Figure 21:
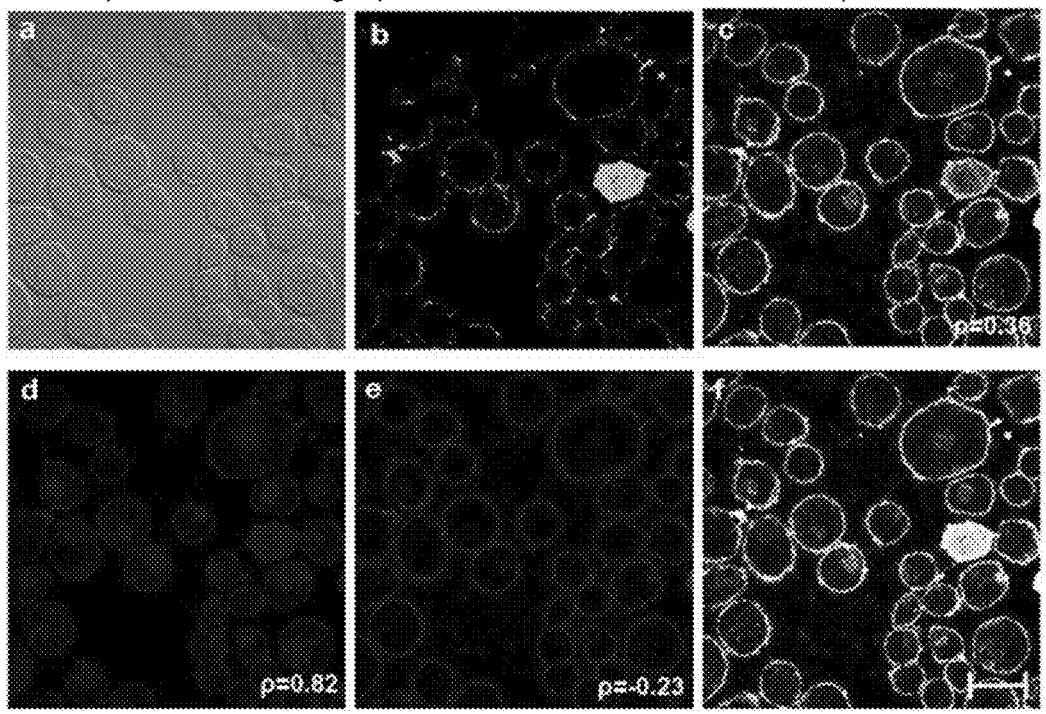
Figure 21:
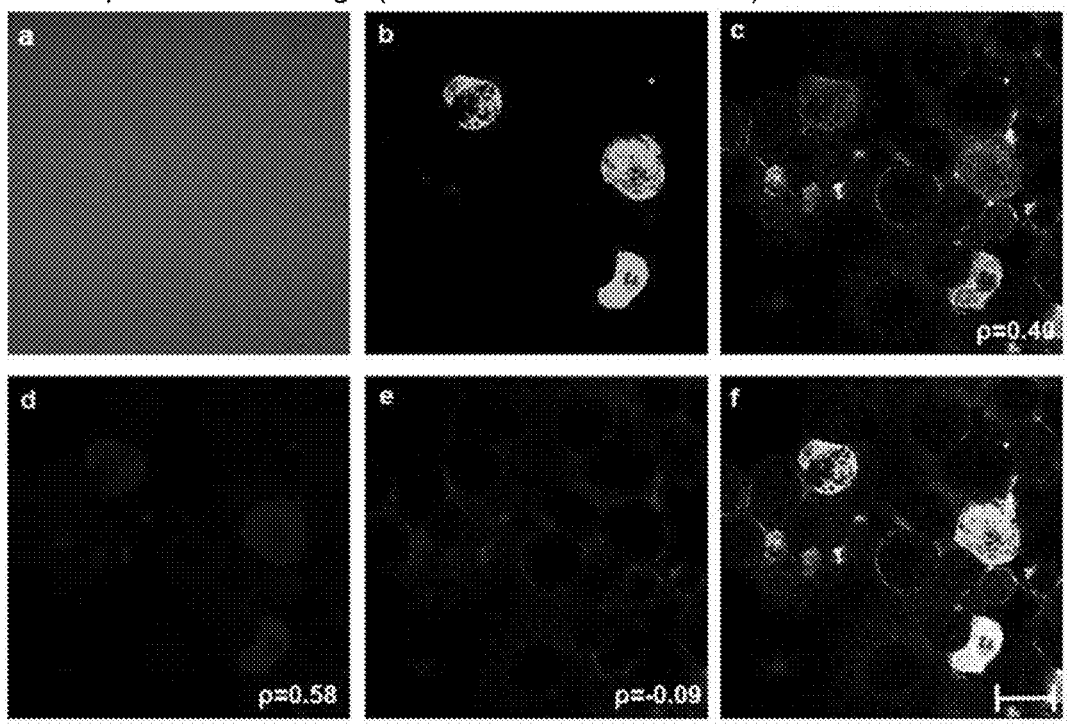

Detection of ALDH1A1 activity in K562 cells. To investigate the ALDH1A1 sensing capabilities of AlDeSense in cell culture, we utilized the K562 human chronic myeloid leukemia cell line, which is known to exhibit high overall ALDH activity. We hypothesized that AlDeSense can be used to stratify these cells based on ALDH1A1 activity and that the brightest cells would exhibit CSC markers. First, using flow cytometry analysis, we found that K562 cells stained with AlDeSense are significantly brighter compared to those treated with either AlDeSense with an inhibitor or Ctrl-AlDeSense (FIG. 2a-c, FIG. 13). We also identified a population of AlDeSense positive cells that exhibits the CD34+/CD38– profile characteristic of leukemic stem cells. The relative proportion of these cells increased when K562 cells were cultured under an environment low in oxygen (FIG. 14). Exposure to hypoxia is a common condition to enrich for CSCs. We also assessed the utility of AlDeSense for confocal fluorescence imaging, which in contrast to flow cytometry, requires less sample and allows for visual assessment of cell morphology (FIG. 2d). First, we determined the subcellular staining pattern of AlDeSense. ALDH1A1 is a cytoplasmic enzyme and therefore, AlDeSense should not be localized to organelles such as the mitochondria where other ALDH isoforms (e.g., ALDH2) are present at high abundance. Co-staining with organelle-specific trackers revealed that AlDeSense did in fact stain the cytoplasm and was not extensively localized to various organelles (FIG. 15, FIG. 16). After several minutes, a small population of highly fluorescent cells began to emerge owing to ALDH1A1-mediated activation of our probe. Treatment with an ALDH inhibitor as well as ALDH1A1-specific siRNA knockdown confirmed that ALDH1A1 is responsible for the fluorescence enhancement. (FIG. 2g, FIG. 17, FIG. 18). Further confirmation of in cellulo selectivity was obtained by comparing K562 cells with HEK293T cells, an ALDH1A1 negative cell line (FIG. 19). Cells treated with Ctrl-AlDeSense allowed us to establish baseline microscope settings which account for fluorescence due to accumulation of dye (FIG. 20). Applying these settings to the AlDeSense-stained population, any cell which shows fluorescence above baseline can only be due to the ALDH1A1-catalyzed turnover of AlDeSense (FIG. 2d-f). Of note, the brightest cells also displayed the CD34+/CD38–/CD133+ leukemic stem cell profile (FIG. 21), suggesting that AlDeSense was being activated to the greatest extent in putative CSCs.

Identification of CSCs in cell culture using AlDeSense.

Next, we sought to determine whether our probe would yield greater fluorescence in CSCs obtained using two different enrichment strategies. First, we used the well-established mammosphere assay to cultivate MDA-MB-231 CSCs by growing cells in low serum conditions on non-adherent plates. Under these conditions, non-CSCs die off, leaving individual CSCs to proliferate into spherical structures. Mammospheres as well as tumorspheres derived from other cancer types have been shown to generate cells with nearly all known CSC characteristics—such as increased in vivo tumorigenicity, invasiveness, metastasis rates, EMT transition, and resistance to chemotherapeutics. Thus they are widely used to study CSCs and develop CSC-specific therapeutics. Mammospheres stained with AlDeSense were 3-fold brighter than those stained with Ctrl-AlDeSense, showing increased levels of ALDH1A1 activity in the mammospheres. In addition, transferring the mammospheres to normal cell culture media and allowing them to differentiate led to a gradual decrease of AlDeSense signal over 36 hours, demonstrating that AlDeSense can be used to monitor CSC differentiation (FIG. 3a-e).

For the second model in our study, we chose to enrich CSCs using a protocol published by Kilian and co-workers (Nat Mater 2016, 15, 856), where they reported that B16-F0 melanoma cells cultured on a spiral-patterned hydrogel platform to mimic mechanical properties of the tumor microenvironment gave rise to cells that displayed increased CSC marker expression (e.g., CD271), as well as metastatic potency and tumorigenicity. Only a small fraction of the B16-F0 cells cultured under standard conditions were identified to exhibit elevated ALDH1A1 activity via flow cytometry and confocal imaging using AlDeSense. However, when the cells enriched in CSCs via the patterned platform (herein referred as e-CSCs) were treated with AlDeSense, they were 11.3-fold brighter than those grown under standard conditions (referred herein as non-CSCs). e-CSCs treated with AlDeSense were also 9.0-fold brighter than e-CSCs treated with Ctrl-AlDeSense, demonstrating that the signal was due to ALDH1A1 (FIG. 3f-j). Flow cytometry analysis revealed that e-CSCs displayed colocalization of AlDeSense with CD271, a commonly used melanoma stem cell marker, when compared to non-CSCs (FIG. 22).

Ex vivo imaging of ALDH1A1 activity in e-CSCs.

Figure 4:
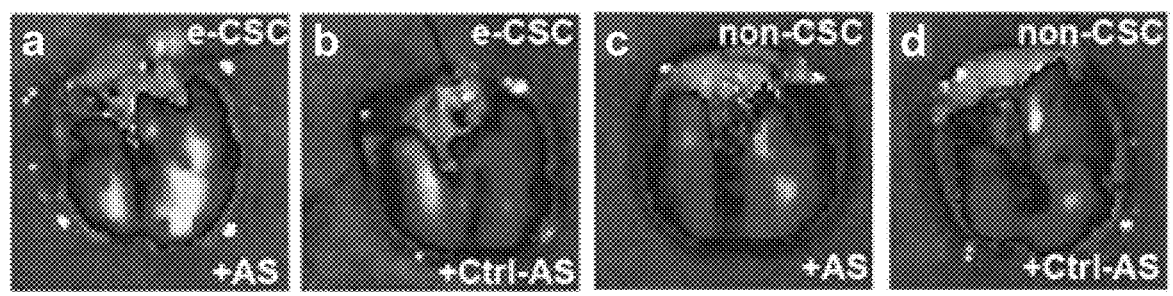
FIG. 4. Assessment of AlDeSense in murine melanoma models. Representative images of lungs collected at day 11 with (a) e-CSC metastases stained with AlDeSense, (b) e-CSC metastases stained with Ctrl-AlDeSense, (c) non-CSC metastases stained with AlDeSense, and (d) non-CSC metastases stained with Ctrl-AlDeSense, all displayed as bright field images overlaid with fluorescence signal. Staining with AlDeSense (e) led to a significant difference in signal between e-CSC metastases and non-CSC metastases but staining with Ctrl-AlDeSense (f) did not show a difference between e-CSC and non-CSC. When analyzing the e-CSC samples, AlDeSense showed a significant increase in signal in comparison to Ctrl-AlDeSense (g). This difference was not observed when analyzing non-CSC samples (h). For graphs (e)-(h) error bars are ±SD, n≥4 for each condition.
Figure 4:
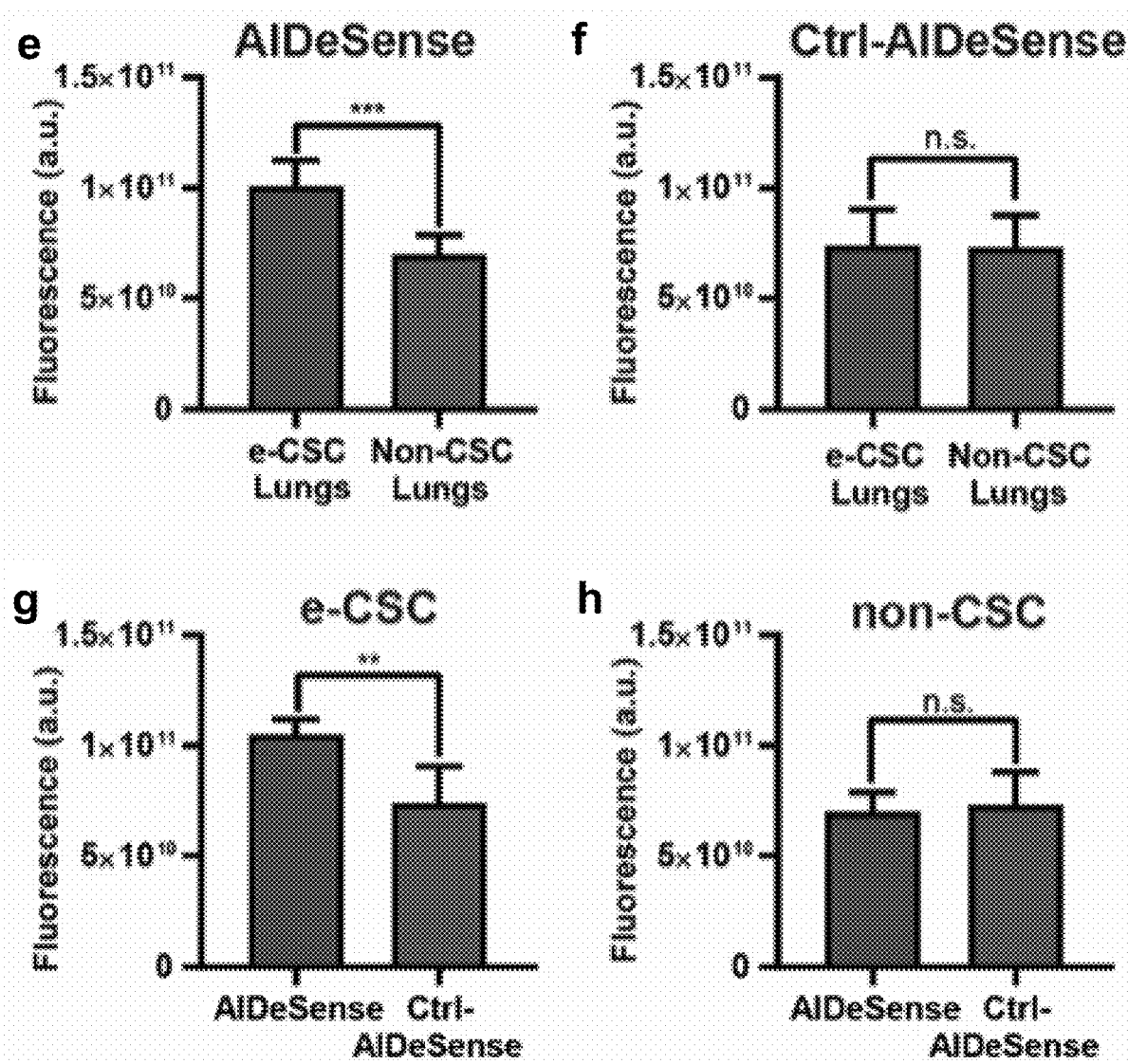

We subsequently sought to visualize ALDH1A1 activity in e-CSCs introduced into whole animal models. First, we intravenously injected either e-CSCs or non-CSCs into mice via the tail vein to generate metastatic lesions in the lung. Immunocompetent mice were used with this syngeneic cell line because the immune system is known to influence the tumor microenvironment and hence properties of CSCs in vivo. Since e-CSCs lost many of the stem cell-related properties within 5 days after they were re-plated on glass slides, it was essential to determine whether ALDH1A1 activity was maintained after CSCs were introduced into a living system. Specifically, can metastatic niches be established within this time frame before differentiation takes place? We hypothesized that if e-CSCs retained their stemness, the AlDeSense signal would be higher for e-CSC lungs compared to non-CSC lungs. At various time points during tumor progression (day 7 and 11) mice were sacrificed, their lungs were removed and perfused with solutions of either AlDeSense or Ctrl-AlDeSense (FIG. 4a-d). When stained with AlDeSense, the fluorescence of the e-CSC-treated lungs were indeed higher than the signal from non-CSC-treated lungs (FIG. 4e). However, it is possible that e-CSCs simply gave rise to larger metastatic lesions which could uptake more dye, leading to increased fluorescence intensity. To resolve this, we compared the signal of e-CSC and non-CSC lungs stained with Ctrl-AlDeSense and found that they were not statistically different, allowing us to confidently rule out this as a possibility (FIG. 4f). Moreover, e-CSC lungs also had a higher signal from AlDeSense versus Ctrl-AlDeSense (FIG. 4g). On the other hand, differences in intensity were not observed between AlDeSense and Ctrl-AlDeSense in lungs with non-CSC metastases (FIG. 4h). Results from days 7 and 11 showed consistent patterns (FIG. 23). Taken together, these results demonstrate that the e-CSCs continue to have higher ALDH1A1 activity levels after introduction into a living system, and that AlDeSense in conjunction with Ctrl-AlDeSense can be used to identify e-CSCs exhibiting this activity.

In Vivo Imaging of ALDH1A1 Activity in e-CSCs Implanted into Live Animals.

Figure 5:
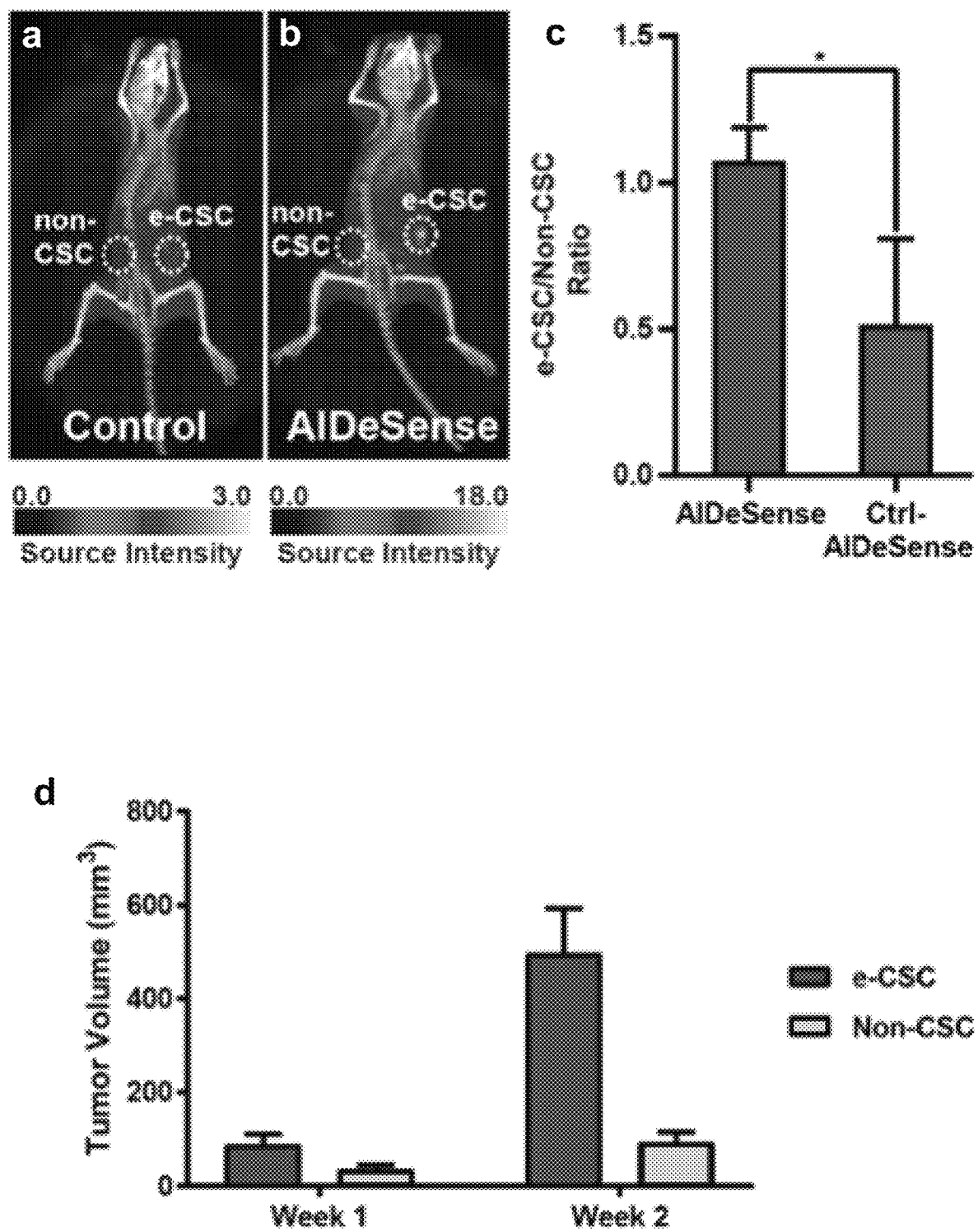
FIG. 5. Representative images of mice implanted with both non-CSC and e-CSC tumors on either flank and injected with (a) Ctrl-AlDeSense or (b) AlDeSense intratumorally. Tumor regions are highlighted with white dotted-circles and fluorescence signal was overlaid over CT images to show placement of signal. (c) Ratio of signal from e-CSC/non-CSC tumors is shown for both Ctrl-AlDeSense and AlDeSense injections. Error bars are ±SD, n=3 for each dye. (d) Mean volumes of both e-CSC and non-CSC tumors throughout the time course of the experiment. Error bars are ±SD, n=5 for each tumor type.

With this information in hand, we then evaluated the tumorigenicity of e-CSCs and the corresponding performance of AlDeSense in a live animal model. Allografts in BALB/c mice were generated via the subcutaneous injection of e-CSCs and non-CSCs into the right and left flanks, respectively. Tumors were monitored and imaged up to 2 weeks using a whole-body fluorescence imaging set-up following an intratumoral injection of AlDeSense or Ctrl-AlDeSense. Results revealed a consistently higher signal from AlDeSense in the e-CSCs versus non-CSCs tumors (FIG. 5a-c) at both 1 and 2 weeks. Ctrl-AlDeSense, on the other hand, did not show increased signal from the e-CSC tumor and had much lower signal over all. This demonstrates that AlDeSense can be used to image ALDH1A1 activity in vivo, and more importantly that e-CSCs retained high ALDH1A1 activity after implantation and induction of tumorigenesis. Moreover, consistent with higher tumorgenicity, implantation of e-CSCs into mice yielded larger, more aggressive tumors compared to non-CSCs (FIG. 5d).

DISCUSSION

We have developed AlDeSense, a powerful new turn-on fluorescent reagent optimized for the detection of CSCs and monitoring of stem cell plasticity via ALDH1A1 activity. Unactivated AlDeSense is weakly fluorescent owing to d-PeT quenching from the pendant benzaldehyde moiety; however, the fluorescence signal is enhanced by nearly 20-fold upon oxidation to the corresponding benzoic acid product by ALDH1A1. Importantly, we did not observe cross-reactivity with any of the other ALDH isoforms tested. This selectivity can be attributed to benzaldehyde being a better substrate for ALDH1A1 and a crucial ionic interaction that we postulate to be forming between the negatively charged dye scaffold and a positively charged His residue at the entrance of the ALDH1A1 active site. Attempts to elucidate the exact nature of this selectivity by co-crystallizing AlDeSense and ALDH1A1 were unsuccessful. The interaction between the active site cysteine residue (Cys-302) and AlDeSense results in a dynamic equilibrium between the aldehyde and hemithioacetal forms which creates too much disorder for crystallographic visualization of the complex. Nevertheless, the exquisite selectivity of AlDeSense for ALDH1A1 over other isoforms, as well as its excellent chemoselectivity against a panel of biologically relevant analytes ensures that any signal above the background established using Ctrl-AlDeSense is due to ALDH1A1 activity.

This property offers unique advantages over existing approaches such as those that involve antibody-dye conjugates for CSC imaging. Dyes that are appended to antibodies targeting CSCs are always in a fluorescent 'on' state, meaning background signal will be high. In contrast, AlDeSense is weakly fluorescent until it is activated by ALDH1A1 and any non-specific staining can be readily accounted for by employing the matching control reagent (Ctrl-AlDeSense). Another advantage is that our probe is compatible with many cancer cell types because elevated ALDH1A1 activity is a general property of CSCs. In contrast, CSC surface biomarkers are unique to specific cancers but are often ill-defined and heterogeneously displayed. Because AlDeSense is cell-permeable and acts intracellularly, it does not directly interfere with native cell-surface processes through formation of tight-binding antibody-antigen interactions, offering yet another advantage. Finally, AlDeSense will only activate if CSCs are viable because ALDH1A1 depends on availability of NADH. In contrast, CSCs that are no longer living can still display surface biomarkers. In comparison to BAAA, a non-selective commercial reagent designed to also target ALDH activity, AlDeSense is selective for only the ALDH1A1 isoform. BAAA on the other hand has been shown to react with a variety of isoforms, including ALDH1A2, ALDH1A3, ALDH2, and ALDH4A1 (FIG. 24). Furthermore, AlDeSense is a turn-on probe that localizes in the cytosol, while BAAA is accumulation-based and localizes to the ER and mitochondria (FIG. 25). This means that unlike BAAA, AlDeSense does not require either ALDH or efflux pump inhibitors to selectively label CSCs and will not show false positives from mitochondrially-located ALDH isoforms, such as ALDH2.

Owing to the unique imaging capabilities of AlDeSense, CSCs enriched using various approaches can be imaged via confocal microscopy to approximate the degree of stemness versus the extent of differentiation. Indeed, we have demonstrated in this study through the application of surface marker antibody staining, tumorsphere assays, and assessment of tumorigenicity, that cells exhibiting high AlDeSense signal intensity have properties of CSCs. For both chronic myelogenous leukemia and melanoma, cells exhibiting the CSC markers CD34+/CD38−/CD133+ and CD271, respectively, were amongst the brightest cells when stained with AlDeSense. In addition to co-staining with antibodies, we also generated CSC-enriched mammospheres and showed that they displayed elevated ALDH1A1 activity. We also observed a decrease in ALDH1A1 activity by allowing the mammospheres to differentiate over time, demonstrating that AlDeSense could be used as a tool to monitor CSC plasticity. Lastly, we used AlDeSense to assess CSC plasticity after introduction into living systems.

Prior to this study, it was unknown whether e-CSCs would maintain stemness properties such as high ALDH1A1 activity after introduction into a living system. Our imaging experiments demonstrate that ALDH1A1 activity persists up to several weeks in e-CSCs after they are introduced into a living animal, implicating that a niche must be established that supports this population of cells. Efforts focused on employing AlDeSense to determine parameters of the tumor microenvironment that govern the transition from a differentiated to CSC state and vice versa. This work has focused on two fronts. First, the development of red-shifted congeners to enable higher resolution imaging of CSCs in deeper tissues. Second, the generation of selective probes for other ALDH isoforms such as ALDH1A3 that are also believed to be linked to stemness. Beyond leading to a greater understanding of fundamental CSC biology, AlDeSense and other ALDH activity-based probes can be utilized as powerful prognostic indicators and assist in the development of CSC-specific chemotherapeutics.

Rational Design of a Red Fluorescent Sensor for ALDH1A1 Displaying Enhanced Cellular Uptake and Reactivity High aldehyde dehydrogenase 1A1 (ALDH1A1) activity has emerged as a reliable marker for the identification of both normal and cancer stem cells. To facilitate the detection, molecular imaging, and sorting of stem cells, a green fluorescent probe based on the xanthene dye scaffold was developed. However, green dyes are less amenable to multicolor imaging because most commercial reagents are also green. Overcoming this limitation will enable the simultaneous tracking of multiple stem cell markers. Herein, we report the development of a red congener, red-AlDeSense. Through chemical tuning we were able to achieve excellent isoform selectivity and chemostability, a good turn on response, and enhanced cellular uptake and reactivity. Importantly, red-AlDeSense represents one of only a few examples of a turn-on sensor in the red region using the d-PeT quenching mechanism. By employing red-AlDeSense and a green anti-CD44 antibody, we were able to demonstrate staining of these two stem cell markers is independent of one another in A549 lung adenocarcinoma cells.

Results and Discussion

Along with other members of the aldehyde dehydrogenase (ALDH) family (19 in total), ALDH1A1 is an important cytosolic enzyme that serves to detoxify endogenous and xenobiotic aldehydes through oxidation to their corresponding carboxylic acid products. Although the precise reasons are not well understood, ALDH1A1 is overexpressed in many normal and cancer stem cell types, where it is used as a well-established stem cell marker. Patient sample analyses using immunohistochemistry and PCR-based methods have revealed that ALDH1A1 levels are commonly elevated in breast, lung, ovarian, and prostate cancer, as well as in leukemia and lymphoma. These results often correlate with poor prognosis and patient survival.

Non-invasive detection of ALDH1A1 in live samples, as opposed to the destructive approaches mentioned above, can enable real-time monitoring and longitudinal tracking of stem cell properties. We reported above the development of AlDeSense, an activity-based sensor that permitted the first studies of stem cell plasticity (via ALDH1A1 activity) in tumorsphere and animal models (FIG. 1a). Owing to donor-photoinduced electron transfer (d-PeT) quenching from the benzaldehyde substrate, this sensor is weakly fluorescent prior to activation. ALDH1A1-catalyzed oxidation to the carboxylic acid product is accompanied by a robust fluorescence turn-on response. Despite the major advance this approach represents, we have improved two properties to broaden its general utility. First, AlDeSense is not cell permeable unless it is chemically modified with capping groups (i.e., acetoxymethyl ether) to mask the intrinsic negative charge character on the phenolic alcohol (pKa=4.81). Consequently, intracellular esterases are required for full activation (FIG. 1a). This process generates by-products, namely acetate and formaldehyde, which are released upon uncapping. Second, the absorbance and emission profile of AlDeSense overlaps with that of FITC and GFP, small-molecule and protein handles, respectively, that are commonly used to visualize biological processes via molecular imaging.

In this work, we also developed red-AlDeSense, a cell-permeable, red-shifted activity-based sensor for ALDH1A1 based on the TokyoMagenta dye platform (FIG. 1a). Chemical tuning of the substituents on the pendent aryl ring was crucial to maintain excellent isoform selectivity while achieving a good turn-on response upon enzyme-mediated oxidation. To account for non-specific staining, we designed a non-responsive control reagent (Ctrl-red-AlDeSense). This tool was used in tandem with red-AlDeSense to identify A549 lung adenocarcinoma cells exhibiting the highest ALDH1A1 activity via flow cytometry and confocal microscopy. Multicolor imaging of red-AlDeSense with a FITC-labeled anti-CD44 antibody revealed independent staining for ALDH1A1 activity and the non-small cell lung cancer stem cell marker.

We initially developed a sensor with the requisite properties by simply substituting the endocyclic oxygen with a dimethylsilicon group. Past reports indicated that this modification results in shifts of up to ~100 nm for both excitation and emission maxima. However, we found that the resultant sensor (Probe 1) was no longer selective for ALDH1A1 and that it exhibited an insufficiently small 1.7-fold turn-on response (Table 2). Its relatively large quantum yield (0.32) indicates d-PeT quenching from the benzaldehyde substrate was no longer sufficient. This hypothesis is further supported by the analysis with the Rehm-Weller equation (Equation 1).

$$\Delta G_{et} = E(D^+/D) - E(A/A^-) - \Delta E_{00} + w_p \quad (1)$$

The term $\Delta E_{00}$ describes the energy difference between the lowest vibrational energy levels of the ground and first electronic energy states. $\Delta E_{00}$ can be estimated by the intersecting wavelength of the normalized absorbance and emission profiles. Specifically, AlDeSense has $\Delta E_{00}=2.46$ eV at 503 nm, while TokyoMagenta dyes have $\Delta E_{00} \sim 2.07$ eV at 600 nm. Given the ~0.4 eV difference, we hypothesized we could achieve a greater dynamic range by reducing the electron density of the pendant aryl ring. We first explored the effects of introducing a single electron deficient substituent (fluoro, trifluoromethyl, and nitro) by replacing the methyl group at the R1 position. While none of these modifications led to the desired properties, each congener provided useful insights for further chemical tuning. For instance, we found that the fluoro substituent (Probe 2) did not provide sufficient steric bulk to prevent nucleophilic attack (e.g., by water) on the xanthene core which resulted in rapid decomposition of the fluorophore. In contrast, modification with a trifluoromethyl group (Probe 3) displayed slow enzyme kinetics, suggesting that it was too large and therefore not able to effectively bind to the ALDH1A1 active site. Lastly, the nitro moiety was too strong of a d-PeT quencher, as we could not determine by fluorescence kinetics assays whether Probe 4 was not turning over or if its carboxylate product was equally quenched.

TABLE 2

Structure and selected properties of Probes 1-8.

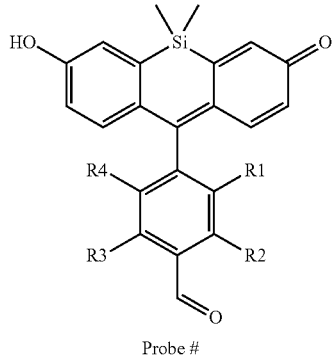

Probe #

| # | R1 | R2 | R3 | R4 | Quantum Yield | Enzymatic Turn On | Enzyme Activity 1A1 | 1A3 |
|---|-----|----|----|----|-------|------|--------|--------|
| 1 | CH₃ | H | H | H | 0.32 | 1.7 | High | Medium |
| 2 | F | H | H | H | n.d. | n.d. | n.d. | n.d. |
| 3 | CF₃ | H | H | H | 0.25 | 2.7 | Medium | Low |
| 4 | NO₂ | H | H | H | 0.00 | n.d. | n.d. | n.d. |
| 5 | CH₃ | H | F | H | 0.21 | 2.6 | High | Low |
| 6 | F | H | H | F | 0.13 | 3.9 | High | High |
| 7 | CH₃ | H | F | F | 0.21 | 3.2 | High | Low |
| 8 | CH₃ | F | H | F | 0.20 | 3.1 | High | Medium | n.d = not determined.

We then turned our attention to tuning the LUMO energy levels of Probes 1 and 2 by installing fluorines at the R3 and R4 positions, respectively. Relative to the 1.7-fold turn on that was observed for Probe 1, activation of Probe 5 with ALDH1A1 resulted in a 2.6-fold fluorescent enhancement. In contrast to the instability of Probe 2, the second fluoro group was sufficient to prevent water-mediated decomposition of Probe 6. Although this sensor displayed the largest response to ALDH1A1 in the series (3.9-fold), it exhibited cross-reactivity with ALDH1A3. Drawing from our findings, we reasoned we would be able to maintain isoform selectivity and achieve a sufficient turn-on response if we installed an additional fluoro group to Probe 5 at the position R4. The resultant sensor, Probe 7 (named red-AlDeSense), was selective for ALDH1A1 over ALDH1A3 and displayed a 3.2-fold turn-on response when treated with ALDH1A1. Finally, we prepared the constitutional isomer of red-AlDeSense (Probe 8) to probe the impact of different fluoro substitution patterns. We found the ALDH1A1-to-ALDH1A3 selectivity was eroded when the fluoro group at R3 was moved to the R2 position.

Synthesis of red-AlDeSense began with Fisher esterification of 4-bromo-2,3-difluorobenzoic acid followed by iodination with N-iodosuccinimide to afford methyl 4-bromo-2,3-difluoro-5-iodobenzoate 2 in 71.7% yield. Suzuki coupling with methylboronic acid chemoselectively substituted the iodine with a methyl group to yield compound 3 in 61.0% yield. DIBAL-H reduction of the ester and subsequent TBS protection of the resultant benzyl alcohol afforded the desired aryl bromide 5 in 83.3% yield. One pot lithium-halogen exchange with t-BuLi, coupling with the TBS-protected Si-xanthone 6, and global deprotection afforded the penultimate precursor 7 in 64.8% yield. Finally, red-AlDeSense was synthesized by oxidation of the benzyl alcohol with IBX in 45.1% yield (Scheme 2).

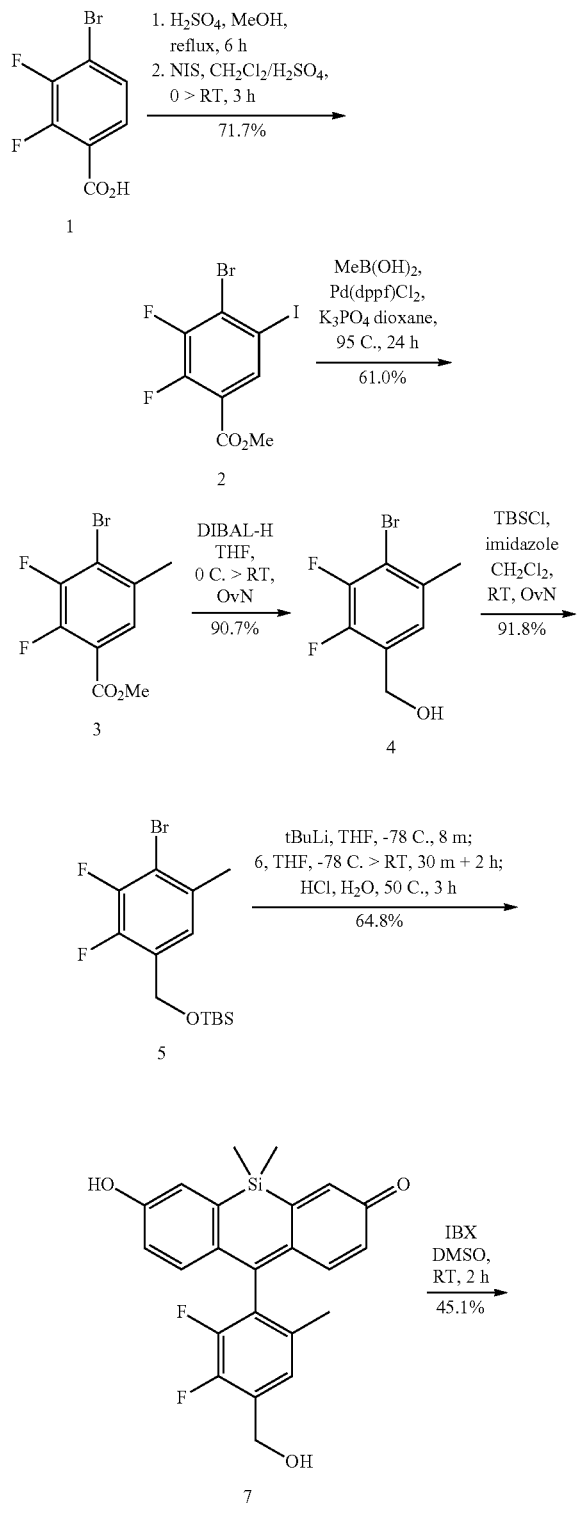

The maximum absorbance ($\lambda_{abs}$) and emission ($\lambda_{em}$) wavelengths of red-AlDeSense were centered at 594 nm and 614 nm, respectively (FIG. 26a). Of note, $\lambda_{abs}$ aligns perfectly with the HeNe-594 nm laser line, which is common in many instruments. Compared to AlDeSense ($k_{cat}/K_m$=3.46 $\mu M^{-1}min^{-1}$), our new sensor responded significantly faster under identical conditions with a measured $k_{cat}/K_m$ of 7.91 $\mu M^{-1}min^{-1}$ (FIG. 26b). In addition to determining the ALDH1A1-to-ALDH1A3 selectivity ratio, we also tested against ALDH1A2, ALDH2, ALDH3A1, ALDH4A1, and ALDH5A1. In each instance, we found no cross-reactivity (FIG. 26c). We also examined the chemostablity of red-AlDeSense across a panel of reactive oxygen, nitrogen, and sulfur species and found only ALDH1A1 elicited turnover of the sensor (FIG. 26d).

Before proceeding to live cell imaging, we synthesized a control dye (Ctrl-red-AlDeSense). The difference between the two dyes is the replacement of the aldehyde group with a methyl ketone moiety. Since ALDH1A1 relies on hydride transfer to an $NAD^+$ cofactor for substrate oxidation, this modification renders Ctrl-red-AlDeSense chemically inert to ALDH1A1. On the other hand, this small change leaves the physical properties nearly identical such that the cell permeability should be the same. Therefore, staining with Ctrl-red-AlDeSense can be used to account for background fluorescence from non-specific staining. Finally, we established that both red-AlDeSense and Ctrl-red-AlDeSense are nontoxic to K562 cells using the trypan blue assay (FIG. 27).

We then turned our attention to determining whether red-AlDeSense could be used to identify A549 lung adenocarcinoma cells with high ALDH1A1 activity via flow cytometry. Cells were first stained with the non-responsive control compound (Ctrl-red-AlDeSense) to establish gating conditions for background fluorescence (FIG. 28a). Using red-AlDeSense, we determined that 78.1±0.3% of A549 cells displayed high ALDH1A1 activity (FIG. 28b). We were able to decrease the extent of red-AlDeSense activation to 67.8±3.4% by applying 4-diethylaminobenzaldehyde (DEAB), a reversible competitive inhibitor of ALDHs (FIG. 28c). Compared to A549 cells, K562 chronic myeloid leukemia cells have lower transcriptional levels of ALDH1A1. As such, we evaluated whether this would translate into differences in ALDH1A1 activity. Indeed, only 39.0±8.3% of K562 cells had high ALDH1A1 activity which correlates with transcriptome data. Moreover, DEAB treatment was also able to decrease sensor activation (FIG. 28d). Consistent with flow cytometry analysis, 77.6% of red-AlDeSense stained A549 cells were determined to have high ALDH1A1 activity using confocal microscopy (FIG. 28e).

Lastly, we sought to highlight the multicolor imaging capabilities of the new sensor using a green FITC-labeled anti-CD44 antibody. The surface biomarker expression profiles of cancer stem cells sometimes correlate with and other times are independent of ALDH1A1. Thus, we wanted to investigate whether A549 cells with the highest ALDH1A1 activity would correlate with those with the greatest extent of CD44 staining. Using confocal imaging, we found that most cells were CD44+ as evidenced by a clear cell membrane staining pattern. However, only a subset of these cells were highly fluorescent on the red-AlDeSense channel (FIG. 28f). This suggests CD44 and ALDH1A1 are independent markers (FIG. 29).

In summary, we have developed a red fluorescent sensor that is selective for ALDH1A1. To our knowledge, this is the first example in which a rational design approach was employed to develop a red fluorescent sensor based on the d-PeT mechanism. The major advantage of red-AlDeSense is its cell permeability, which can be attributed to the pKa value of the phenolic alcohol (6.68). As such, the sensor requires only the action of ALDH1A1 for both accumulation and fluorescence turn on. Moreover, we observed 2.3-fold higher catalytic efficiency ($k_{cat}/K_m$) for the new sensor. The change to Si-xanthene and modification of the pendant aryl ring substituents resulted in a 100 nm bathochromic shift in absorbance and emission compared to our first-generation sensor (AlDeSense). Bathochromic shifting allowed for multicolor imaging using a green FITC-labeled anti-CD44 antibody. From these studies we showed independent staining for ALDH1A1 activity and CD44 levels in A549 lung adenocarcinoma cells. We believe red-AlDeSense will emerge as a useful tool for studying cells expressing high ALDH1A1 activity.

General Methods and Materials

Materials.

Thin-layer chromatography (TLC) was performed on 0.25 mm silica-coated TLC plates containing an UV254 fluorescent indicator from Machery-Nagel. Compounds were visualized using a UVP UVGL-25 Compact UV Lamp. Flash chromatography was performed with 230-400 mesh silica gel P60 from SiliCycle Inc. Triethylamine was purchased from Acros Organics. Hydrogen gas was purchased from Airgas. 2-iodobenzoic acid, 4-bromo-3,5-dimethoxybenzaldehyde, and methylboronic acid were purchased from AK Scientific. 2,4-dinitrobenzenesulfonyl chloride and anhydrous pyridine were purchased from Alfa Aesar. 4-bromo-3,5-difluorobenzoic acid was purchased from Arctom. 3-methoxybenzyl alcohol was purchased from ArkPharm. All deuterated solvents were purchased from Cambridge Isotope Laboratories. 1,4-dibromo-2-fluoro-5-methylbenzene was purchased from Santa Cruz Biochemicals. 4-bromo-2,3-difluorobenzoic acid, 4-bromo-3-(trifluoromethyl)benzoic acid, 4-bromo-3-fluorotoluene, and methyl 4-bromo-3-methylbenzoate were purchased from CombiBlocks. $CH_2Cl_2$, THF, $Et_2O$, EtOAc, hexanes, $HNO_3$, iPrOH, $NaHCO_3$, toluene, and the Pierce™ BCA Protein Assay Kit were purchased from Thermo Fisher Scientific. Cylcohexane, DMSO, $H_2SO_4$, MeOH, NaOH, and THF were purchased from Macron. $CaCO_3$ was purchased from Mallinckrodt Pharmaceuticals. 1,4-dioxane, 2,4,5-trifluorobenzoic acid, 3-bromophenol, Celite®, $CuBr_2$, dimethylcarbamyl chloride, imidazole, $K_3PO_4$, methyl iodide, N-bromosuccinimide, N-iodosuccinimide, $Na_2S_2O_3$, $NaBH_4$, Oxone®, Pd(dppf)$C_{12}$, tert-butyldimethylsilyl chloride, triethanolamine, and trifluoroacetic acid were purchased from Oakwood Chemical. 1.0 M $BH_3$-THF in THF, 1.0 M DIBAL-H in $CH_2Cl_2$, 1.0 M DIBAL-H in hexanes, 1.0 M LiHMDS in THF, 1.4 M sec-butyllithium in cyclohexane, 1.7 M tert-butyllithium in pentane, 10% w/w Pd/C, 2.5 M n-butyllithium in hexanes, 3.0 M methylmagnesium bromide in $Et_2O$, 4-bromobenzoic acid, AIBN, anhydrous MeCN, dichlorodimethylsilane, DMF, LiAlH$_4$, tert-butyl nitrite, and trypan blue were purchased from MilliporeSigma. 1,4-bis(trifluoromethyl)benzene was purchased from SynQuest Laboratories. Benzylamine was purchased from TCI America. HCl was purchased from VWR. THF used for anhydrous reactions was dried over activated 4 A molecular sieves for a minimum of 24 hours. All other chemicals were used as received.

pKa Determination.

Buffers used for pH titrations were glycine (pH=2.3-3.7), NaOAc (pH=4.0-5.6), MES (pH=5.7-6.7), HEPES (pH=6.9-8.1), and CHES (pH=8.6-9.5). All buffers were prepared to a concentration of 50 mM in $H_2O$ using aqueous NaOH and HCl to adjust pH. For each condition, 1 µM red-AlDeSense was excited at 594 nm, and an emission spectrum was collected from 600-650 nm. Each condition was performed in triplicate. Data was analyzed using Microsoft Excel.

Expression and Purification of ALDH Isoforms.

Plasmids for ALDH1A1, ALDH1A2, ALDH1A3, ALDH2, ALDH3A1, ALDH4A1, and ALDH4A1 were generously provided by Professor Daria Mochly-Rosen (Stanford). Expression and purification of each isoform was performed as previously described (ACS Cent. Sci. 2018, 4 (8), 1045).

ALDH Isoform Selectivity.

Each ALDH isoform was added to a 50 mM triethanolamine solution (pH 7.4) containing 2.0 mM NAD$^+$ and 100 µM substrate at room temperature. Benzaldehyde was the substrate for ALDH3A1. Propanal was the substrate for all other isoforms. ALDH isoform activity was determined by monitoring the rate of NADH production through the increase in absorbance at 340 nm ($\varepsilon$=6220 M$^{-1}$cm$^{-1}$). For these assays, 1 unit is defined as the amount of enzyme that catalyzes the conversion of 1 µM substrate per minute. For every combination of dye and enzyme, 2 µM dye was preincubated with 2.0 mM NAD$^+$ in 50 mM triethanolamine solution (pH 7.4). The reaction was initiated by addition of 1 unit of ALDH. Dyes were excited at 590 nm, and fluorescence was measured continuously at 610 nm.

ALDH1A1 Kinetics.

Solutions were prepared of 2.0 mM NAD+ and 0.1-2.5 µM AlDeSense or red-AlDeSense in 50 mM triethanolamine solution (pH 7.4). For every concentration, 1 unit of enzyme (as defined and determined in ALDH Isoform Selectivity) was added. Fluorescence was monitored for 30 seconds to determine $V_0$. AlDeSense was excited at 490 nm and monitored at 510 nm. Red-AlDeSense was excited at 590 nm and monitored at 610 nm. Each condition was performed in triplicate. Protein concentration was determined using the Pierce™ BCA Protein Assay Kit. Data was analyzed using Microsoft Excel.

Trypan Blue Viability Assay.

K562 cells were plated in a 96-well plate with 50,000 cells per well. Each well was filled to a final volume of 100 µL IMDM media with 0.25% DMSO. Wells were tested using red-AlDeSense or Ctrl-red-AlDeSense (1 µM and 5 µM each) or using a DMSO control. After 6-, 12-, and 24-hour incubation periods at 37° C. and 5% $CO_2$, a 10 µL sample was removed from each condition and combined with 10 µL 0.4% w/v trypan blue in PBS. Samples were incubated for 3 minutes at room temperature before being loaded on a hemocytometer where live and dead cells were counted. Conditions were tested in triplicate for each time point. Samples were analyzed on an EVOS digital inverted microscope using transmitted white light for brightfield imaging and the Cy5 filter cube for trypan blue visualization.

Cell Culture.

K562 cells were obtained from Prof. Paul Hergenrother (UIUC). K562 cells were cultured using Iscove's Modified Dulbecco's Medium (IMDM, ATCC) supplemented with 10% fetal bovine serum (FBS, Sigma) and 1% penicillin/streptomycin (pen-strep, Corning). A549 cells were purchased from the American Type Culture Collection (ATCC) and cultured in Dulbecco's Modified Eagle Medium (DMEM, ATCC) supplemented with 10% FBS, 1% pen-strep, and non-essential amino acids. All cells were grown at 37° C. in a humidified incubator with 5% CO2. For each cell line, media was changed or cells were passaged every 3 days. Passage numbers were kept below 20 for all experiments.

Flow Cytometry.

For all cell lines, 200,000 cells in a single-cell suspension were transferred into 1.5 mL Eppendorf tubes. Cells were pelleted by centrifugation at 400 g for 5 minutes at room temperature. After removing the supernatant by aspiration, cells were resuspended in 300 μL premixed PBS supplemented with verapamil, probenecid, and novobiocin. For the indicated samples, DEAB (final concentration 20 μM) was added. Samples were immediately stored on ice. Cells were stained with red-AlDeSense or Ctrl-red-AlDeSense (100 μL of 4 μM dye solution; dyes were normalized by fluorescence spectroscopy). Samples were analyzed on a BD LSR II Flow Cytometry Analyzer using a 488 nm laser and a 550 LP and 610/30 filter set. Samples were analyzed every 5 minutes for 15 minutes, with the samples being placed back on ice between data collection. Data were analyzed on FCS Express 6.04.

Confocal Imaging.

Nunc™ Lab-Tek™ 8-well Chamber Coverglass (Thermo Fisher) were coated with poly-L-lysine (Trevigen). For cells that were also stained with an antibody, 2,000,000 cells were transferred to an Eppendorf tube. The cells were resuspended in 200 μL of antibody buffer (5% BSA and 1 mg/mL $NaN_3$ in PBS) and treated with 2 μL FITC-labeled anti-CD44 antibody (10 mg/mL, Sino Biological) and left on ice for 20 minutes. In all cases, cells were added at 150,000 cells/well to the coated slides 1 hour prior to imaging. Before imaging, the media was aspirated and each chamber was refilled with 300 μL premixed imaging buffer (100 μM verapamil, 2.5 mM probenecid, and 200 μM novobiocin in PBS plus 5% BSA and 1 mg/mL $NaN_3$ for antibody-stained cells) at room temperature. Cells were treated with 100 uL red-AlDeSense or Ctrl-red-AlDeSense solution (4 μM dye in imaging buffer; dyes were normalized by fluorescence spectroscopy) and 0.8 μL Hoescht 33342 (5 mg/mL in PBS) for 10 minutes. Live cell imaging was performed on a Multiphoton Confocal Microscope Zeiss 710. Hoescht 33342 was excited with a 405 nm laser and detected with a 415-502 filter set. FITC was excited with a 488 nm laser and detected with a 502-561 filter set. Hoescht 33342 was excited with a 594 nm laser and detected with a 600-735 filter set. For each condition, three images were taken for each of four different wells using the 40× objective. The same optical settings were used for images within each set of matched experiments. Images were analyzed using ZEN 3.0 (blue edition) software. Mean fluorescence for the FITC-labeled anti-CD44 antibody was multiplied by the cell diameter to account for its 1-dimensional cell membrane staining, as opposed to 2-dimensional intracellular staining of (Ctrl-)red-AlDeSense. Cells were considered to have high ALDH activity when they had a mean red-AlDeSense fluorescence signal greater than 99% of Ctrl-red-AlDeSense-stained cells.

Pharmaceutical Formulations

The compounds described herein can be used to prepare pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiologically acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, or subcutaneous routes.

The compounds described herein may be systemically administered in combination with a pharmaceutically acceptable vehicle, such as an inert diluent or an assimilable edible carrier. For oral administration, compounds can be enclosed in hard- or soft-shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze-drying techniques, which yield a powder of the active ingredient plus any additional desired ingredient present in the solution.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Synthetic Methods and Compound Characterization ((4-Bromo-3-methylbenzyl)oxy) (tert-butyl)dimethylsilane (2)

A flame-dried round-bottom flask was charged with methyl 4-bromo-3-methylbenzoate (11.5 g, 50.0 mmol, 1.00 eq.) and anhydrous $CH_2Cl_2$ (100 mL). A flame-dried addition funnel was attached to the flask and the system was flushed with nitrogen. The reaction was cooled to 0° C. and treated with 1.0 M DIBAL-H in $CH_2Cl_2$ (110 mL, 110 mmol, 2.2 eq.) via funnel addition over 23 minutes. The reaction was allowed to warm to room temperature. After stirring at room temperature for 4 hours, the reaction was cooled to 0° C. and quenched via the slow addition of $H_2O$ (5 mL), 1 M NaOH (5 mL), and additional $H_2O$ (30 mL). The resulting emulsion was poured over filter paper and washed with $CH_2Cl_2$. The organics were combined, dried over $Na_2SO_4$, and concentrated under reduced pressure. The crude residue containing 1 was eluted through a silica plug and concentrated to afford a light-yellow oil which was used without further purification. A solution of this intermediate in anhydrous $CH_2Cl_2$ (50 mL) was treated with imidazole (6.8 g, 100 mmol, 2.0 eq.) and tert-butyldimethylsilyl chloride (8.2 g, 55 mmol, 1.1 eq.). After overnight stirring, the reaction was filtered and washed with $CH_2Cl_2$. The filtrate was collected, washed with aqueous $NH_4C_1$, and concentrated under reduced pressure. The crude material was purified via flash chromatography on a silica column (2:98 v/v EtOAc:Hexanes) to afford the title compound (14.6 g, 46.3 mmol, 92.6% yield over two-steps beginning from methyl 4-bromo-3-methylbenzoate). $^1$H NMR (500 MHz, $CDCl_3$) δ 7.47 (d, J=8.1 Hz, 1H), 7.18 (d, J=1.6 Hz, 1H), 7.01 (dd, J=8.2, 1.5 Hz, 1H), 4.66 (s, 2H), 2.39 (s, 3H), 0.94

(s, 9H), 0.10 (s, 6H). $^{13}$C NMR (125 MHz, CDCl$_3$) δ 140.82, 137.67, 132.22, 128.63, 125.20, 123.15, 64.48, 26.09, 23.09, 18.57, −5.10.

2,7-Difluoro-3, 6-bis((2-methoxyethoxy)methoxy)-9H-xanthen-9-one (3)

The titled compound was prepared according the procedure published by Peterson and co-workers (Synthesis (Mass) 2014, 46, 158).

2,7-Difluoro-6-hydroxy-9-(4-(hydroxymethyl)-2-methylphenyl)-3H-xanthen-3-one (4)

A flame-dried round-bottom flask was charged with 2 (0.348 g, 1.1 mmol, 1.1 eq.) and anhydrous THF (5 mL). The reaction was cooled to −78° C. and treated with 1.4 M sec-butyllithium in cyclohexane (0.9 mL, 1.1 mmol, 1.1 eq.). The reaction was stirred at the same temperature for 30 minutes and then treated with a solution of 3 (0.440 g, 1.0 mmol, 1.0 eq.) in anhydrous THF (5 mL). The reaction was stirred at the same temperature for 2 hours. The reaction was warmed to room temperature and treated with 1.0 M aq. HCl (6.0 mL, 6.0 mmol, 6.0 eq.). The reaction was warmed to 50° C. and stirred for 4 hours. The reaction was concentrated under vacuum to remove the THF and cyclohexane. The remaining mixture was poured over filter paper, washed with H$_2$O (100 mL) and CH$_2$Cl$_2$ (100 mL), and vacuum dried to yield the title compound as a red-orange solid (0.176 g, 0.483 mmol, 48.3% yield). $^1$H NMR (500 MHz, DMSO-d$_6$) δ 7.44 (s, 1H), 7.39 (d, J=7.7 Hz, 1H), 7.23 (d, J=7.7 Hz, 1H), 6.82 (d, J=6.0 Hz, 2H), 6.59 (d, J=11.3 Hz, 2H), 5.33 (s, OH), 4.62 (s, 2H), 2.02 (s, 3H). $^{13}$C NMR (125 MHz, DMSO-d$_6$) δ 150.29 (t, J=6.1 Hz), 144.31, 135.32, 129.86, 128.71, 128.50, 124.21, 114.00, 111.28 (d, J=21.9 Hz), 105.06 (d, J=4.3 Hz), 62.52, 19.11. HRMS-ESI (m/z): [M+H]$^+$ Calc. mass for C$_{21}$H$_{15}$O$_4$F$_2$=369.0938; Found mass=369.0930.

AlDeSense.

A round-bottom flask was charged with 4 (0.368 g, 1.0 mmol, 1.0 eq.), IBX (0.336 g, 1.2 mmol, 1.2 eq.), and DMSO (10 mL). After stirring for 3 hours at room temperature, the reaction was quenched via the addition of brine (100 mL). The resulting mixture was poured over filter paper and vacuum dried. The red solid was suspended in H$_2$O (200 mL) and heated to 80° C. After stirring for 2 hours, the reaction was cooled to room temperature and poured over filter paper and vacuum dried to yield the title compound as a rust-orange solid (0.290 g, 0.79.2 mmol, 79.2% yield). AlDeSense used in biological assays was further purified via chromatography on a silica column (10:90 v/v MeOH:CH$_2$Cl$_2$). $^1$H NMR (500 MHz, DMSO-d$_6$) δ 10.12 (s, 1H), 8.02 (s, 1H), 7.95 (d, J=7.8 Hz, 1H), 7.52 (d, J=7.6 Hz, 1H), 6.80 (d, J=6.8 Hz, 1H), 6.60 (d, J=11.4 Hz, 2H), 2.12 (s, 3H). $^{13}$C NMR (125 MHz, DMSO-d$_6$) δ 193.01, 154.48, 154.28, 152.48, 148.77 (t, J=5.7 Hz), 138.57, 136.95, 136.83, 131.32, 129.88, 127.32, 110.11 (d, J=21.7 Hz), 109.50 (d, J=8.2 Hz), 104.93 (d, J=5.4 Hz), 18.90. [M+H]$^+$ Calc. mass for C$_{21}$H$_{13}$O$_4$F$_2$=367.0782; Found mass=367.0784.

AlDeSense AM.

A flame-dried round-bottom flask was charged with AlDeSense (0.037 g, 0.10 mmol, 1.0 eq.), anhydrous DMF (2.0 mL), bromomethyl acetate (0.020 mL, 0.20 mmol, 2.0 eq.), and Hünig's base (0.035 mL, 0.20 mmol, 2.0 eq.). After stirring for 12 hours at room temperature, all volatiles were removed under vacuum at room temperature. The crude material was purified via column chromatography on a silica column (20:80 v/v EtOAc:CH$_2$Cl$_2$) to afford the title compound as an orange solid (0.0265 g, 0.060 mmol, 60.4% yield). $^1$H NMR (500 MHz, DMSO-d$_6$) δ 10.14 (s, 1H), 8.03 (s, 1H), 7.98 (d, J=7.8 Hz, 1H), 7.76 (d, J=6.9 Hz, 1H), 7.52 (d, J=7.7 Hz, 1H), 6.81 (d, J=10.9 Hz, 1H), 6.63 (d, J=11.1 Hz, 1H), 6.55 (d, J=7.0 Hz, 1H), 6.01 (s, 2H), 2.14 (s, 3H), 2.13 (s, 3H). $^{13}$C NMR (125 MHz, DMSO-d$_6$) δ 193.51, 175.18 (d, J=20.8 Hz), 169.80, 157.56 (t, d, J=5.1 Hz), 155.16 (d, J=265.5 Hz), 148.82 (d, J=245.5 Hz), 149.12, 148.91 (d, J=12.5 Hz), 147.81 (d, J=9.8 Hz), 137.33, 137.23, 137.14, 131.55, 130.02, 127.44, 117.80 (d, J=8.5 Hz), 113.98 (d, J=7.7 Hz), 113.02 (d, J=21.5 Hz), 109.73 (d, J=21.8 Hz), 105.77 (d, J=4.8 Hz), 104.62, 84.80, 20.58, 19.00. [M+H]$^+$ Calc. mass for C$_{24}$H17O6F$_2$=439.0993; Found mass=439.1008.

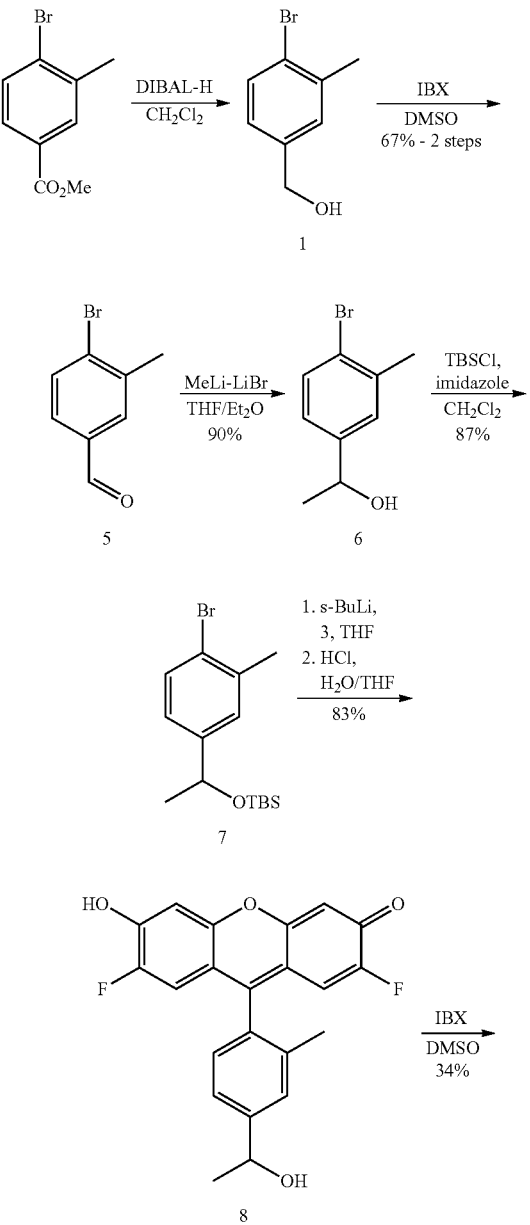

Scheme 3. Synthesis of Ctrl-AlDeSense and Ctrl-AlDeSense AM.

-continued

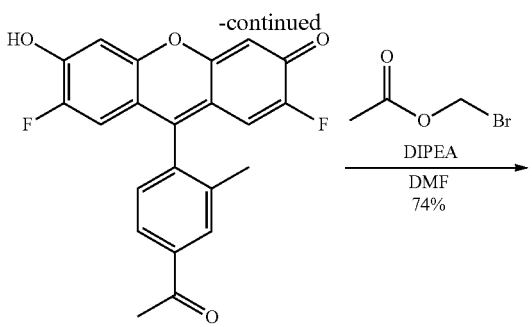

Ctrl-AlDeSense

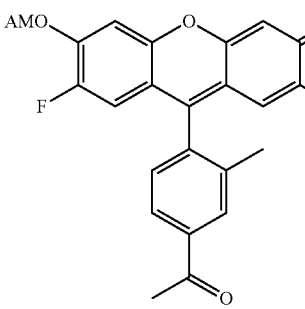

Ctrl-AlDeSense AM

4-Bromo-3-methylbenzaldehyde (5)

A flame-dried round-bottom flask was charged with methyl 4-bromo-3-methylbenzoate (2.29 g, 10 mmol, 1.0 eq.) and anhydrous $CH_2Cl_2$ (20 mL). A flame-dried addition funnel was attached to the flask and the system was flushed with nitrogen. The reaction was cooled to 0° C. and treated with 1.0 M DIBAL-H in $CH_2Cl_2$ (22 mL, 22 mmol, 2.2 eq.) via funnel addition over 10 minutes. The reaction was allowed to warm to room temperature. After stirring at room temperature for 4 hours, the reaction was cooled to 0° C. and quenched via the slow addition of $H_2O$ (5 mL), 1 M NaOH (5 mL), and additional $H_2O$ (20 mL). The resulting emulsion was poured over filter paper and washed with $CH_2Cl_2$. The organics were combined, dried over $Na_2SO_4$, and concentrated under reduced pressure to afford 1 as a crude residue which was used without further purification. A solution of this intermediate in DMSO (10 mL) was treated with IBX (3.36 g, 12 mmol, 1.2 eq.). After stirring for 3 hours at room temperature, the reaction was diluted with brine (100 mL), poured over filter paper, and washed through with $Et_2O$. The aqueous layer was extracted from with $Et_2O$ (50 mL). The organics were combined, washed with brine, dried over $Na_2SO_4$, and concentrated. The crude material was purified by column chromatography (10:90 v/v EtOAc:Hexanes) to afford the title compound as a light red oil (1.333 g, 6.70 mmol, 67.0% yield). $^1$H NMR (500 MHz, $CDCl_3$) δ 9.95 (s, 1H), 7.73 (d, J=1.4 Hz, 1H), 7.71 (d, J=8.1 Hz, 1H), 7.55 (dd, J=8.1, 2.0 Hz, 1H), 2.48 (s, 3H). $^{13}$C NMR (125 MHz, $CDCl_3$) δ 191.52, 139.29, 135.57, 133.38, 132.35, 131.59, 128.40, 23.04.

1-(4-Bromo-3-methylphenyl)ethan-1-ol (6)

A flame-dried round-bottom flask was charged with 5 (1.926 g, 9.68 mmol, 1.0 eq.) and anhydrous THF (25 mL). The reaction was cooled to 0° C. and treated with 1.5 M methyllithium lithium bromide in $Et_2O$ (7.4 mL, 11.1 mmol, 1.15 eq.) dropwise via syringe addition. The reaction was stirred at the same temperature for 15 minutes and then warmed to room temperature. After stirring 2 hours at room temperature, the reaction was quenched via addition of sat. $NH_4C_1$ (50 mL). The organics were collected, dried over $Na_2SO_4$, and concentrated to yield the title compound as a yellow oil (1.876 g, 8.72 mmol, 90.1% yield). $^1$H NMR (500 MHz, $CDCl_3$) δ 7.49 (d, J=8.2 Hz, 1H), 7.24 (d, J=1.8 Hz, 1H), 7.05 (dd, J=8.2, 1.8 Hz, 1H), 4.83 (q, J=5.9 Hz, 1H), 2.40 (s, 3H), 1.93 (s, 1H), 1.46 (d, J=6.5 Hz, 3H). $^{13}$C NMR (125 MHz, $CDCl_3$) δ 145.17, 138.05, 132.48, 128.01, 124.51, 123.71, 69.93, 25.34, 23.08.

(1-(4-Bromo-3-methylphenyl)ethoxy) (tert-butyl) dimethylsilane (7)

A round-bottom flask was charged with 6 (0.215 g, 1.0 mmol, 1.0 eq.), $CH_2Cl_2$ (5 mL), and imidazole (0.138 g, 2.0 mmol, 2.0 eq.). Once a solution had formed, the reaction was treated with tert-butyldimethylsilyl chloride (0.186 g, 1.2 mmol, 1.2 eq.). After stirring for 12 hours at room temperature, the reaction was concentrated. The crude residue was purified via flash chromatography on a silica column (5:95 v/v EtOAc:Hexanes) to afford the title compound as a colorless oil (0.287 g, 0.871 mmol, 87.1% yield). $^1$H NMR (500 MHz, $CDCl_3$) δ 7.47 (d, J=8.2 Hz, 1H), 7.20 (d, J=2.2 Hz, 1H), 7.04 (dd, J=8.2, 2.2 Hz, 1H), 4.82 (q, J=6.4 Hz, 1H), 2.41 (s, 3H), 1.39 (d, J=6.4 Hz, 3H), 0.92 (s, 9H), 0.07 (s, 3H), 0.00 (s, 3H). $^{13}$C NMR (125 MHz, $CDCl_3$) δ 146.44, 137.49, 132.16, 127.83, 124.41, 122.92, 70.40, 27.38, 26.01, 23.12, 18.40, −4.64, −4.68. [M−H]$^-$ Calc. mass for $C_{15}H_{24}OBrSi$=327.07798; Found mass=327.07648.

2,7-Difluoro-6-hydroxy-9-(4-(1-hydroxyethyl)-2-methylphenyl)-3H-xanthen-3-one (8)

A flame-dried round-bottom flask was charged with 7 (0.494 g, 1.5 mmol, 1.6 eq.) and anhydrous THF (5 mL). The reaction was cooled to −78° C. and treated with 1.4 M sec-butyllithium in cyclohexane (1.0 mL, 1.4 mmol, 1.4 eq.). The reaction was stirred at the same temperature for 30 minutes and then treated with a solution of 3 (0.441 g, 1.0 mmol, 1.0 eq.) in anhydrous THF (3 mL). The reaction was stirred at the same temperature for 2 hours. The reaction was warmed to room temperature and treated with 1.0 M HCl in $H_2O$ (12 mL, 12 mmol, 12 eq.). The reaction was warmed to 50° C. and stirred for 24 hours. The reaction was concentrated under reduced pressure. The crude residue was purified via chromatography on a silica column (10:90 v/v MeOH:$CH_2Cl_2$) to afford the title compound as a red-orange solid (0.318 g, 0.832 mmol, 83.2% yield). $^1$H NMR (500 MHz, DMSO-$d_6$) δ 7.47 (s, 1H), 7.41 (d, J=7.8 Hz, 1H), 7.21 (d, J=7.8 Hz, 1H), 6.81 (d, J=6.5 Hz, 2H), 6.58 (d, J=11.3 Hz, 2H), 5.29, (s, 1H), 4.82 (q, J=6.4 Hz, 1H), 2.02 (s, 3H), 1.42 (d, J=6.5 Hz, 3H). $^{13}$C NMR (125 MHz, DMSO-$d_6$) δ 153.48, 152.17 (d, J=252.4 Hz), 150.32 (t, J=5.8 Hz), 149.04, 135.22, 129.75, 128.66, 127.59 (d, J=7.9 Hz), 123.30, 114.00, 111.27 (d, J=21.5 Hz), 105.03 (d, J=3.8 Hz), 67.79, 25.71, 19.18. [M+H]$^+$ Calc. mass for $C_{22}H17O4F_2$=383.1095; Found mass=383.1099.

Ctrl-AlDeSense.

A round-bottom flask was charged with 8 (0.191 g, 0.50 mmol, 1.0 eq.), IBX (0.168 g, 0.6 mmol, 1.2 eq.), and DMSO (5 mL). After stirring for 12 hours at room temperature, the reaction was quenched via the addition of brine (50 mL). The resulting mixture was poured over filter paper and vacuum dried. The crude residue was purified via chromatography on a silica column (5:95 v/v MeOH:CH$_2$Cl$_2$) to afford the title compound as a rust-orange solid (0.065 g, 0.171 mmol, 34.1% yield). $^1$H NMR (500 MHz, DMSO-d$_6$) δ 8.05 (s, 1H), 7.99 (dd, J=7.9, 1.8 Hz, 1H), 7.42 (d, J=7.9 Hz, 1H), 6.67 (d, J=7.1 Hz, 2H), 6.44 (d, J=11.2 Hz, 2H), 2.67 (s, 3H), 2.11 (s, 3H). $^{13}$C NMR (125 MHz, DMSO-d$_6$) δ 197.73, 154.14 (t, J=5.9 Hz), 138.17, 136.94, 130.75, 129.93, 126.59, 113.44 (d, J=7.8 Hz), 111.46 (d, J=21.8 Hz), 105.56 (d, J=4.4 Hz), 27.37, 19.51. [M+H]$^+$ Calc. mass for C$_{22}$H1504F2=381.0938; Found mass=381.0934.

Ctrl-AlDeSense AM. A flame-dried round-bottom flask was charged with Ctrl-AlDeSense (0.032 g, 0.084 mmol, 1.0 eq.), anhydrous DMF (2.0 mL), bromomethyl acetate (0.017 mL, 0.17 mmol, 2.0 eq.), and Hünig's base (0.029 mL, 0.17 mmol, 2.0 eq.). After stirring for 12 hours at room temperature, all volatiles were removed under vacuum at room temperature. The crude material was purified via column chromatography on a silica column (20:80 v/v EtOAc:CH$_2$Cl$_2$) to afford the title compound as an orange solid (0.0281 g, 0.062 mmol, 73.8% yield). $^1$H NMR (500 MHz, CDCl$_3$) δ 7.86 (s, 1H), 7.82 (dd, J=7.9, 1.6 Hz, 1H), 7.16 (d, J=6.7 Hz, 1H), 7.12 (d, J=7.9 Hz, 1H), 6.56 (d, J=10.6 Hz, 1H), 6.44 (d, J=6.9 Hz, 1H), 6.39 (d, J=10.4 Hz, 1H), 5.73 (s, 2H), 2.54 (s, 3H), 2.02 (s, 3H), 1.99 (s, 3H). $^{13}$C NMR (125 MHz, CDCl$_3$) δ 197.26, 176.25 (d, J=20.8 Hz), 169.33, 157.45 (d, J=1.8 Hz), 156.82 (d, J=269.2 Hz), 149.85 (d, J=249.1 Hz), 149.65 (d, J=13.1 Hz), 149.35, 147.28 (dd, J=10.0, 2.9 Hz), 138.59, 137.18-136.51 (m), 136.50, 130.75, 129.52, 126.57, 118.94 (d, J=8.4 Hz), 114.66 (d, J=7.5 Hz), 113.41 (d, J=21.5 Hz), 109.47 (d, J=22.4 Hz), 107.09 (d, J=4.7 Hz), 104.67, 85.03, 26.77, 20.77, 19.67. [M+H]$^+$ Calc. mass for C$_{25}$H1906F2=453.1150; Found mass=453.1158.

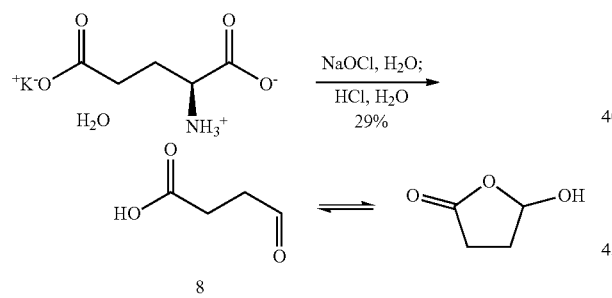

Scheme 4. Synthesis of succinic semialdehyde.

Succinic Semialdehyde (8).

A round-bottom flask was charged with L-glutamic acid potassium salt monohydrate (0.500 g, 2.46 mmol, 1.0 eq.) and H$_2$O (13.8 mL). After heating to 37° C., 6% by weight NaOCl in H$_2$O (2.75 mL, 2.46 mmol, 1.0 eq.) was added dropwise over 1 minute. After stirring at 37° C. for 1 hour, the reaction was treated with 1 M HCl in H$_2$O (2.75 mL, 2.75 mmol, 1.1 eq.). The reaction was left stirring at 37° C. until effervescence had ceased. After cooling to room temperature, NaCl was added before extracting with Et$_2$O (3×20 mL). The organics were combined, dried over Na$_2$SO$_4$, and concentrated under reduced pressure to yield the title compound (0.072 g, 0.71 mmol, 28.7% yield) as a pale-yellow oil. In CDCl$_3$, the ratio of cyclic:acylic product was approximately 1:1 by $^1$H NMR. $^1$H NMR (500 MHz, CDCl$_3$) δ 9.84 (s, 1H), 5.95 (dd, J=5.7, 1.9 Hz, 1H), 2.82 (t, J=6.5 Hz, 2H), 2.76 (ddd, J=17.8, 9.5, 9.1 Hz, 1H), 2.71 (t, J=6.6 Hz, 2H), 2.48 (ddd, J=17.5, 9.8, 3.6 Hz, 1H), 2.37 (dddd, J=13.4, 9.6, 9.0, 5.6 Hz, 1H), 2.16 (dddd, J=13.3, 9.6, 3.6, 2.0 Hz, 1H).

Example 2. Synthetic Methods and Compound Characterization of Silicon Heterocylces

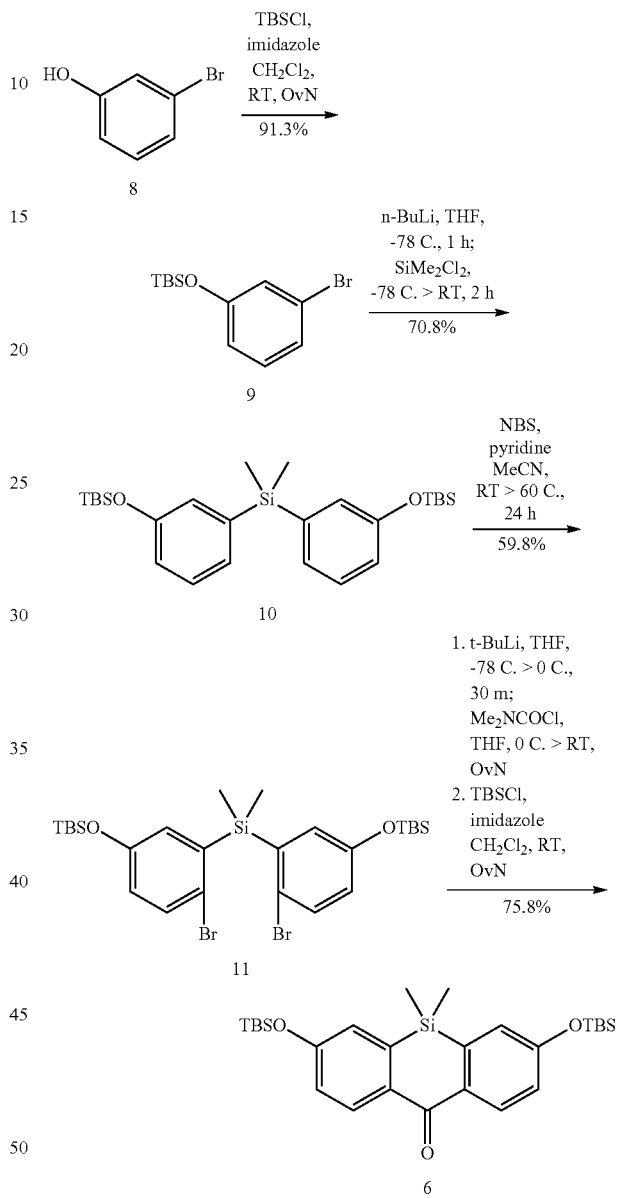

Scheme 5. Synthesis of Xanthone 6.

(3-Bromophenoxy) (tert-butyl)dimethylsilane (9)

A round-bottom flask was charged with 3-bromophenol (8.65 g, 50.0 mmol, 1.0 eq.), tert-butyldimethylsilyl chloride (7.9 g, 52 mmol, 1.05 eq.), imidazole (3.6 g, 52 mmol, 1.05 eq.), and CH$_2$Cl$_2$ (70 mL). After stirring overnight at room temperature, the reaction was washed sequentially with 1.0 M HCl in H$_2$O (50 mL) and 1.0 M NaOH in H$_2$O (50 mL). The organics were collected, dried over Na$_2$SO$_4$, and concentrated under reduced pressure to afford the title compound as a colorless oil (13.12 g, 45.7 mmol, 91.3%). $^1$H NMR (500 MHz, CDCl$_3$) δ 7.12-7.04 (m, 2H), 7.03-6.98 (m, 1H), 6.76 (ddq, J=6.5, 4.2, 2.2 Hz, 1H), 0.98 (s, 9H), 0.20 (s, 6H). $^{13}$C NMR (126 MHz, CDCl$_3$) δ 156.68, 130.55, 124.61, 123.67, 122.61, 118.96, 25.76, 18.33, −4.31.

Bis(3-((tert-butyldimethylsilyl)oxy)phenyl)dimethylsilane (10)

A flame-dried round-bottom flask was charged with 9 (13.12 g, 45.7 mmol, 2.0 eq.) and anhydrous THF (25 mL). The reaction was cooled to −78° C. and then treated dropwise with 2.5 M n-butyllithium in hexanes (18 mL, 45.7 mmol, 2.0 eq.) over 25 minutes. After stirring for an additional hour at −78° C., the reaction was treated dropwise with a solution of dimethyldichlorosilane (2.75 mL, 22.8 mmol, 1.0 eq.) in anhydrous THF (15 mL) over 5 minutes via syringe addition. After addition, the reaction was warmed to room temperature and stirred for 2 hours, then poured over sat. NaHCO$_3$ (50 mL) and diluted with H$_2$O (50 mL). The organics were collected, dried over Na$_2$SO$_4$, and concentrated. The crude material was purified via flash chromatography on a silica column (0:100 to 2:98 v/v EtOAc:hexanes gradient) to afford the title compound as a colorless oil (7.65 g, 16.2 mmol, 70.8% yield). $^1$H NMR (500 MHz, CDCl$_3$) δ 7.22 (t, J=7.6 Hz, 2H), 7.09 (dt, J=7.3, 1.1 Hz, 2H), 6.97 (dd, J=2.5, 1.1 Hz, 2H), 6.83 (ddd, J=8.1, 2.6, 1.1 Hz, 2H), 0.97 (s, 18H), 0.51 (s, 6H), 0.16 (s, 12H). $^{13}$C NMR (126 MHz, CDCl$_3$) δ 155.25, 139.87, 129.09, 127.09, 125.71, 120.92, 25.88, 18.39, −2.32, −4.23.

Bis(2-bromo-5-((tert-butyldimethylsilyl)oxy)phenyl) dimethylsilane (11)

A round-bottom flask was charged with 10 (1.42 g, 3.0 mmol, 1.0 eq.), anhydrous MeCN (20 mL), and anhydrous pyridine (2.0 mL, 24 mmol, 8.0 eq.). The reaction was treated with N-bromosuccinimide (2.35 g, 13 mmol, 4.4 eq.). The reaction was heated to 60° C. for 24 hours. After cooling to room temperature, the reaction was diluted with Et$_2$O and EtOAc, then washed sequentially with 1.0 M HCl in H$_2$O, 1.0 M NaOH in H$_2$O, and brine. The organics were collected, dried over Na$_2$SO$_4$, and concentrated. The crude material was purified via flash chromatography on a silica column (2:98 v/v EtOAc:hexanes) to afford the title compound as a white solid (1.13 g, 1.79 mmol, 59.8% yield). $^1$H NMR (500 MHz, CDCl$_3$) δ 7.35 (d, J=8.5 Hz, 2H), 6.91 (d, J=3.0 Hz, 2H), 6.71 (dd, J=8.6, 3.0 Hz, 2H), 0.95 (s, 18H), 0.72 (s, 6H), 0.14 (s, 12H). $^{13}$C NMR (126 MHz, CDCl$_3$) δ 154.59, 140.03, 133.90, 128.76, 123.17, 121.41, 25.83, 18.39, −1.07, −4.27.

3,7-Bis((tert-butyldimethylsilyl)oxy)-5,5-dimethyldibenzo[b,e]silin-10(5H)-one (6)

A flame-dried round-bottom flask was charged with 11 (3.60 g, 5.7 mmol, 1.0 eq.) and anhydrous THF (50 mL). The reaction was cooled to −78° C. and then treated dropwise with 1.7 M t-butyllithium in pentane (14 mL, 23.4 mmol, 4.1 eq.) over 10 minutes. After stirring for 30 minutes, the reaction was warmed to 0° C. and treated dropwise with 1.0 M dimethylcarbamyl chloride in THF (11.5 mL, 11.5 mmol, 2.0 eq.) over 40 minutes. The reaction was slowly warmed to room temperature with the melting ice bath. After stirring overnight, the THF was removed in vacuo. The crude residue was suspended in CH$_2$Cl$_2$ and treated with imidazole (0.82 g, 12 mmol, 2.1 eq.) and tert-butyldimethylsilyl chloride (1.9 g, 13 mmol, 2.2 eq.). After stirring overnight, the reaction was washed with H$_2$O and concentrated. The crude material was purified via flash chromatography on a silica column (0:100 to 2:98 v/v EtOAc:hexanes gradient) to afford the title compound. This was further dissolved in EtOH and triturated with H$_2$O to afford a white solid (2.16 g, 1.33 mmol, 75.8% yield). $^1$H NMR (500 MHz, CDCl$_3$) δ 8.37 (d, J=8.7 Hz, 2H), 7.04 (d, J=2.5 Hz, 2H), 6.99 (dd, J=8.7, 2.5 Hz, 2H), 1.01 (s, 18H), 0.46 (s, 6H), 0.26 (s, 12H). $^{13}$C NMR (126 MHz, CDCl$_3$) δ 186.11, 158.87, 141.31, 134.71, 132.42, 123.85, 121.92, 25.82, 18.47, −1.39, −4.13.

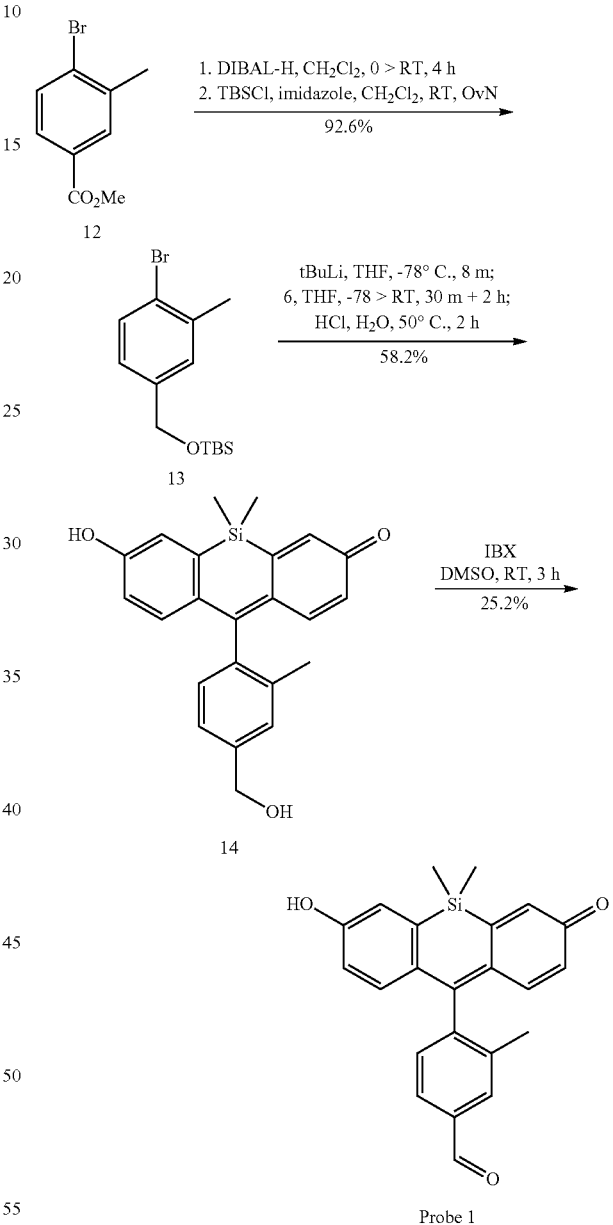

Scheme 6. Synthesis of Probe 1.

((4-Bromo-3-methylbenzyl)oxy) (tert-butyl)dimethylsilane (13)

A flame-dried round-bottom flask was charged with methyl 4-bromo-3-methylbenzoate (22.9 g, 50 mmol, 1.0 eq.) and anhydrous CH$_2$Cl$_2$ (100 mL). The reaction was cooled to 0° C. before treating dropwise with 1.0 M DIBAL-H in CH$_2$Cl$_2$ (110 mL, 110 mmol, 2.2 eq.) over 23 minutes. After stirring for 30 minutes, the reaction was warmed to room temperature. After 4 hours, the reaction was cooled back to 0° C. before quenching with the sequential addition of H$_2$O, 1.0 M NaOH in H$_2$O, and more H$_2$O. The mixture was filtered. The organics were collected, washed with brine, and concentrated. The crude material was treated with imidazole (6.8 g, 100 mmol, 2.0 eq.) and CH$_2$Cl$_2$ (50 mL). Once a solution had formed, tert-butyldimethylsilyl chloride (8.2 g, 50 mmol, 1.1 eq.) was added. After stirring overnight at room temperature, the reaction was filtered. The filtrate was washed with aqueous NH$_4$C$_1$ and concentrated under reduced pressure. The crude material was purified via flash chromatography on a silica column (2:98 v/v EtOAc: hexanes) to afford the title compound as a colorless oil (14.6 g, 46.3 mmol, 92.6% yield). $^1$H NMR (500 MHz, CDCl$_3$) δ 7.47 (d, J=8.1 Hz, 1H), 7.18 (d, J=1.4 Hz, 1H), 7.01 (dd, J=8.2, 2.1 Hz, 1H), 4.66 (s, 2H), 2.39 (s, 3H), 0.94 (s, 9H), 0.10 (s, 6H). $^{13}$C NMR (126 MHz, CDCl$_3$) δ 140.83, 137.67, 132.23, 128.64, 125.21, 123.16, 64.49, 26.09, 23.08, 18.57, −5.10.

7-Hydroxy-10-(4-(hydroxymethyl)-2-methylphenyl)-5,5-dimethyldibenzo[b, e]silin-3(5H)-one (14)

A flame-dried round-bottom flask was charged with 13 (0.325 g, 1.0 mmol, 10 eq.) and anhydrous THF (5 mL). The reaction was cooled to −78° C. and then treated dropwise with 1.7 M t-butyllithium in pentane (0.59 mL, 1.0 mmol, 10 eq.) over 1 minute. After stirring for an additional 8 minutes at −78° C., the reaction was treated dropwise with a solution of 6 (0.051 g, 0.10 mmol, 1.0 eq.) in anhydrous THF (2 mL) over 2 minutes. 30 minutes after addition, the reaction was warmed to room temperature and stirred for 2 hours. The reaction was treated with 1.0 M HCl in H$_2$O (3 mL, 3.0 mmol, 30 eq.) and heated to 50° C. After stirring for 2 hours, the reaction was cooled to room temperature. The reaction was diluted with Et$_2$O and THF and washed with brine. The organics were collected, dried over Na$_2$SO$_4$, and concentrated. The crude material was purified via flash chromatography on a silica column (5:95 v/v MeOH:CH$_2$Cl$_2$). The crude material was washed with Et$_2$O to afford the title compound as a red solid (0.0218 g, 0.0582 mmol, 58.2% yield). $^1$H NMR (500 MHz, DMSO-d$_6$) δ 7.33 (d, J=1.5 Hz, 1H), 7.29 (dd, J=7.8, 1.6 Hz, 1H), 7.07 (d, J=7.7 Hz, 1H), 7.00 (s, 2H), 6.76 (d, J=9.5 Hz, 2H), 6.43 (d, J=7.8 Hz, 2H), 5.29 (s, 1H), 4.57 (s, 2H), 1.98 (s, 3H), 0.46 (s, 3H), 0.44 (s, 3H). $^{13}$C NMR (126 MHz, DMSO-d$_6$) δ 156.30, 143.67, 142.55, 138.07, 137.45, 134.98, 129.14, 128.84, 128.09, 123.98, 122.02, 62.66, 19.08, −1.28, −1.61. HRMS (ESI$^+$): m/z calculated for [M+H]$^+$=375.1411; found=375.1411.

4-(7-Hydroxy-5,5-dimethyl-3-oxo-3,5-dihydrodibenzo[b, e]silin-10-yl)-3-methylbenzaldehyde (Probe 1)

A round-bottom flask was charged with 14 (0.0187 g, 0.050 mmol, 1.0 eq.), 2-iodoxybenzoic acid (0.0169 g, 0.060 mmol, 1.2 eq.), and DMSO (1 mL). After stirring 3 hours at room temperature, the reaction was quenched with brine and filtered. The filtrate was extracted from with 33:67 v/v iPrOH:CH$_2$Cl$_2$. The organics were combined with the precipitate and purified via flash chromatography on a silica column (0:100 to 5:95 v/v iPrOH:CH$_2$Cl$_2$ gradient). The resultant solid purified via flash chromatography on a silica column (Et$_2$O) to afford the title compound as a red solid (0.0047 g, 0.0126 mmol, 25.2% yield). $^1$H NMR (500 MHz, CDCl$_3$) δ 10.09 (s, 1H), 7.86 (s, 1H), 7.85 (dd, J=7.6, 1.5 Hz, 1H), 7.31 (d, J=7.7 Hz, 1H), 7.06 (d, J=2.4 Hz, 2H), 6.81 (d, J=9.5 Hz, 2H), 6.52 (dd, J=9.4, 2.4 Hz, 2H), 2.15 (s, 3H), 0.48 (s, 3H), 0.47 (s, 3H). $^{13}$C NMR (126 MHz, CDCl$_3$) δ 191.92, 146.01, 145.13, 138.97, 137.63, 136.51, 131.37, 130.31, 130.15, 129.51, 127.46, 122.56, 19.60, −1.12, −1.34. HRMS (ESI$^+$): m/z calculated for [M+H]$^+$=373.1254; found=373.1259.

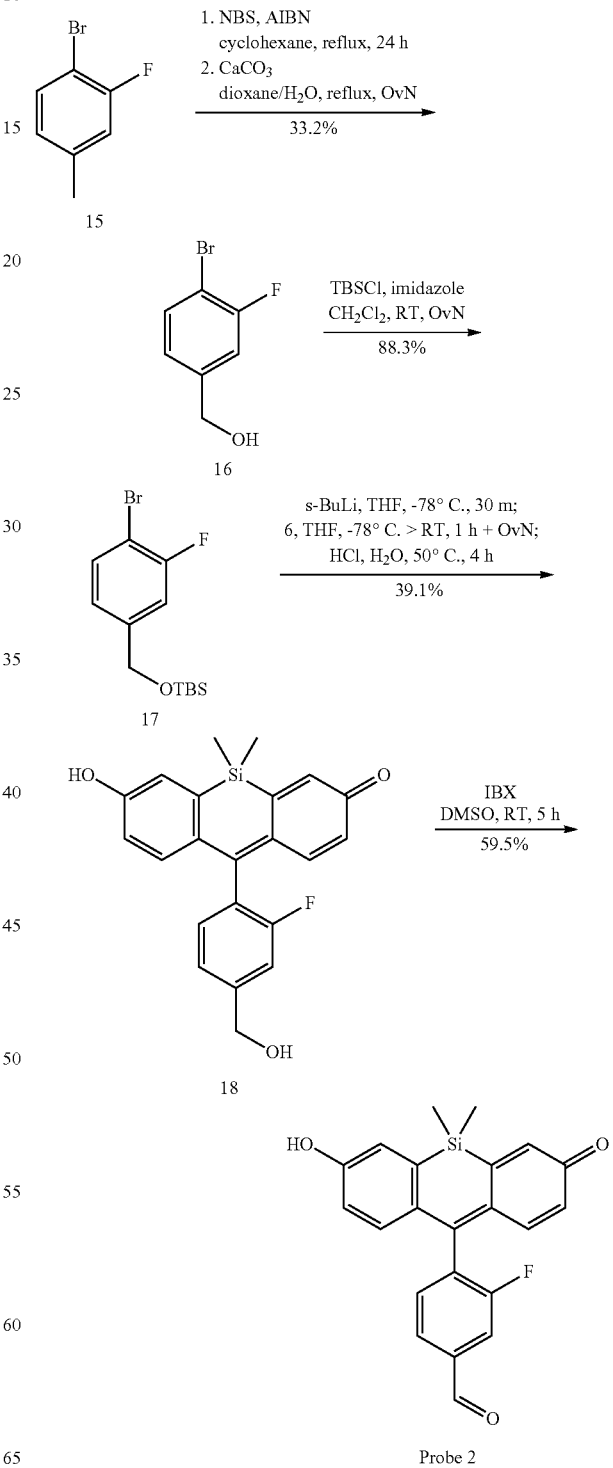

Scheme 7. Synthesis of Probe 2.

(4-Bromo-3-fluorophenyl)methanol (16)

A flame-dried round-bottom flask was charged with 4-bromo-3-fluorotoluene (0.67 mL, 5.3 mmol, 1.0 eq.), N-bromosuccinimide (1.04 g, 5.8 mmol, 1.1 eq.), AIBN (0.086 g, 0.53 mmol, 0.1 eq.), and cyclohexane (20 mL). The reaction was heated to reflux. After stirring for 24 hours, the reaction was cooled to RT and concentrated in vacuo. The crude material treated with dioxane (10 mL), $H_2O$ (10 mL), and $CaCO_3$ (1.59 g, 16 mmol, 3.0 eq.). The reaction was heated to reflux. After stirring overnight, the reaction was cooled to room temperature and concentrated in vacuo. The crude material was purified via flash chromatography on a silica column (5:95 to 30:70 v/v EtOAc:hexanes gradient) to afford the title compound as a colorless oil (0.360 g, 1.76 mmol, 33.2% yield). $^1$H NMR (500 MHz, $CDCl_3$) δ 7.46 (t, J=7.5 Hz, 1H), 7.08 (d, J=9.1 Hz, 1H), 6.94 (d, J=7.7 Hz, 1H), 4.57 (s, 2H). $^{13}$C NMR (126 MHz, $CDCl_3$) δ 159.12 (d, J=247.4 Hz), 142.75 (d, J=6.8 Hz), 133.47, 123.34 (d, J=3.4 Hz), 114.71 (d, J=22.6 Hz), 107.62 (d, J=20.9 Hz), 63.74. $^{19}$F NMR (471 MHz, $CDCl_3$) δ −107.22 (dd, J=9.2, 7.4 Hz).

((4-Bromo-3-fluorobenzyl)oxy) (tert-butyl)dimethylsilane (17)

A round-bottom flask was charged with 16 (0.360 g, 1.76 mmol, 1.0 eq.), imidazole (0.135 g, 1.9 mmol, 1.1 eq.), and $CH_2Cl_2$ (20 mL). Once a solution had formed, tert-butyldimethylsilyl chloride (0.35 g, 2.3 mmol, 1.3 eq.) was added. After stirring overnight at room temperature, the reaction was poured through filter paper. The filtrate was purified via flash chromatography on a silica column (0:100 to 5:95 v/v EtOAc:hexanes gradient) to afford the title compound as a colorless oil (0.490 g, 1.55 mmol, 88.3% yield). $^1$H NMR (500 MHz, $CDCl_3$) δ 7.48 (dd, J=8.2, 7.0 Hz, 1H), 7.12 (d, J=9.6 Hz, 1H), 6.96 (d, J=8.2 Hz, 1H), 4.68 (s, 2H), 0.94 (s, 9H), 0.10 (s, 6H). $^{13}$C NMR (126 MHz, $CDCl_3$) δ 159.25 (d, J=247.1 Hz), 143.72 (d, J=6.3 Hz), 133.27, 122.61 (d, J=3.6 Hz), 114.17 (d, J=22.7 Hz), 106.95 (d, J=21.1 Hz), 63.93 (d, J=1.7 Hz), 26.04, 18.52, −5.16 $^{19}$F NMR (471 MHz, $CDCl_3$) δ −107.75 (dd, J=9.5, 7.0 Hz).

10-(2-Fluoro-4-(hydroxymethyl)phenyl)-7-hydroxy-5,5-dimethyldibenzo[b, e]silin-3(5H)-one (18)

A flame-dried round-bottom flask was charged with 17 (0.095 g, 0.60 mmol, 6.0 eq.) and anhydrous THF (10 mL). The reaction was cooled to −78° C. and then treated dropwise with 1.4 M s-butyllithium in cyclohexane (0.46 mL, 0.60 mmol, 6.0 eq.) over 1 minute. After stirring for an additional 30 minutes at −78° C., the reaction was treated dropwise with a solution of 6 (0.052 g, 0.10 mmol, 1.0 eq.) in anhydrous THF (3 mL) over 3 minutes. 1 hour after addition, the reaction was transferred to an ice bath. The reaction was stirred overnight in the melting ice bath before being treated with 1.0 M HCl in $H_2O$ (4.0 mL, 4.0 mmol, 40 eq.) and heated to 50° C. After stirring for 4 hours, the reaction was cooled to room temperature and quenched with $H_2O$. The THF was removed in vacuo. The resulting mixture was extracted from with 33:67 v/v iPrOH:$CH_2Cl_2$. The organics were collected, dried over $Na_2SO_4$, and concentrated. The crude material was purified via flash chromatography on a silica column (0:100 to 5:95 v/v MeOH:$CH_2Cl_2$ gradient). The resulting solid was washed with $CH_2Cl_2$ to afford the title compound as a red solid (0.0148 g, 0.0391 mmol, 39.1% yield). $^1$H NMR (500 MHz, DMSO-$d_6$) δ 10.54 (s, 1H), 7.32 (d, J=9.0 Hz, 2H), 7.28 (t, J=7.5 Hz, 1H), 7.03 (s, 2H), 6.85 (d, J=8.4 Hz, 2H), 6.49 (s, 2H), 5.45 (s, 1H), 4.63 (s, 2H), 0.46 (s, 3H), 0.45 (s, 3H).1 $^{13}$C NMR (126 MHz, DMSO-$d_6$) δ 158.76 (d, J=243.1 Hz), 149.83, 146.30 (d, J=6.8 Hz), 131.99-129.79 (m), 124.70 (d, J=17.3 Hz), 122.26 (d, J=2.5 Hz), 113.20 (d, J=21.8 Hz), 62.01, −1.29, −1.55. $^{19}$F NMR (471 MHz, DMSO-$d_6$) δ −115.72 (dd, J=9.4, 7.7 Hz). HRMS (ESI$^+$): m/z calculated for [M+H]$^+$=379.1160; found=379.1162.

3-Fluoro-4-(7-hydroxy-5,5-dimethyl-3-oxo-3,5-dihydrodibenzo[b, e]silin-10-yl)benzaldehyde (Probe 2)

A round-bottom flask was charged with 18 (0.0078 g, 0.021 mmol, 1.0 eq.), 2-iodoxybenzoic acid (0.0068 g, 0.025 mmol, 1.2 eq.), and DMSO (0.5 mL). After stirring 5 hours at room temperature, the reaction was quenched with brine. The mixture was chilled and filtered. The filtrate was extracted from with 33:67 iPrOH:$CH_2Cl_2$.+organics were combined with the precipitate and concentrated. The crude material was purified via flash chromatography on a silica column (0:100 to 2:98 v/v iPrOH:$CH_2Cl_2$ gradient) to afford the title compound as a red solid (0.0046 g, 0.012 mmol, 59.5% yield). $^1$H NMR (400 MHz, DMSO-$d_6$) δ 10.62 (s, 1H), 10.12 (s, 1H), 7.95 (dd, J=7.7, 1.3 Hz, 1H), 7.93 (d, J=8.9 Hz, 1H), 7.63 (t, J=7.3 Hz, 1H), 7.27-7.19 (m, 1H), 6.93-6.79 (m, 2H), 6.79-6.68 (m, 2H), 6.25-6.07 (m, 1H), 0.47 (s, 3H), 0.46 (s, 3H). $^{19}$F NMR (376 MHz, DMSO-$d_6$) δ −114.38 (t, J=8.2 Hz). HRMS (ESI$^+$): m/z calculated for [M+H]$^+$=377.1004; found=377.1025.

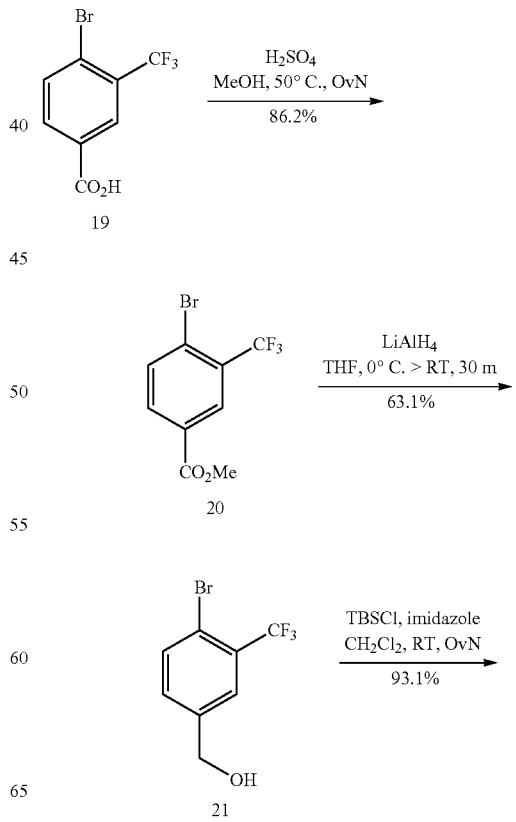

Scheme 8. Synthesis of Probe 3.

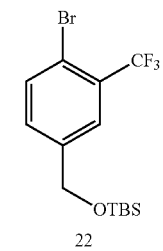

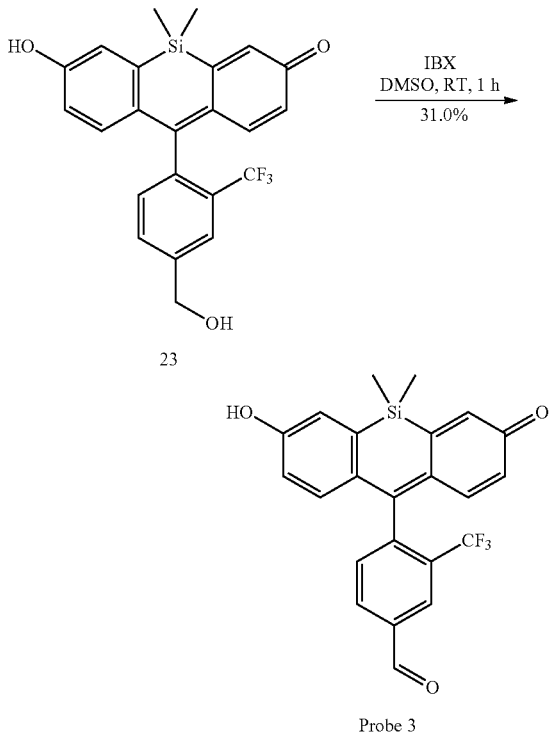

Probe 3

Methyl 4-bromo-3-(trifluoromethyl)benzoate (20)

A round-bottom flask was charged with 4-bromo-3-(trifluoromethyl)benzoic acid (1.35 g, 5.0 mmol, 1.0 eq.), MeOH (10 mL), and conc. $H_2SO_4$ (0.5 mL). The reaction was heated to 50° C. After stirring overnight, the reaction was neutralized with saturated $NaHCO_3$. The resulting mixture was poured through filter paper. The precipitate was further washed with $H_2O$ and dried to afford the title compound as an off-white solid (1.22 g, 4.3 mmol, 86.2% yield). $^1$H NMR (500 MHz, $CDCl_3$) δ 8.34 (d, J=2.1 Hz, 1H), 8.03 (dd, J=8.3, 2.1 Hz, 1H), 7.80 (d, J=8.3 Hz, 1H), 3.95 (s, 3H). $^{13}$C NMR (126 MHz, $CDCl_3$) δ 165.32, 135.47, 133.75, 130.78 (q, J=32.1 Hz), 129.72, 129.06 (q, J=5.4 Hz), 125.58 (q, J=2.0 Hz), 122.64 (q, J=273.7 Hz), 52.83. $^{19}$F NMR (471 MHz, $CDCl_3$) δ −62.94.

(4-Bromo-3-(trifluoromethyl)phenyl)methanol (21)

A flame-dried round-bottom flask was charged with 20 (0.283 g, 1.0 mmol, 1.0 eq.) and anhydrous THF (10 mL). The reaction was cooled to 0° C. before treating with $LiAlH_4$ (0.038 g, 1.0 mmol, 1.0 eq.) portionwise over 1 minute. After effervescence ceased, the reaction was warmed to room temperature. After 30 minutes, the reaction was cooled to 0° C. and quenched via the sequential addition of $H_2O$ (2 mL), 1.0 M NaOH in $H_2O$ (2 mL), and more $H_2O$ (2 mL). The mixture was diluted with $CH_2Cl_2$ and filtered. The organics were collected, dried over $Na_2SO_4$, and concentrated. The crude residue was recrystallized in hexanes to afford the title compound as a white crystalline solid (0.161 g, 0.631 mmol, 63.1% yield). $^1$H NMR (500 MHz, $CDCl_3$) δ 7.69 (s, 1H), 7.68 (d, J=7.5 Hz, 1H), 7.38 (d, J=7.4 Hz, 1H), 4.71 (s, 2H), 1.96 (s, 1H). $^{13}$C NMR (126 MHz, $CDCl_3$) δ 140.55, 135.16, 131.22, 130.37 (q, J=31.2 Hz), 126.22 (q, J=5.4 Hz), 123.01 (q, J=273.4 Hz), 118.88 (q, J=2.0 Hz), 64.02. $^{19}$F NMR (471 MHz, $CDCl_3$) δ −62.66.

((4-Bromo-3-(trifluoromethyl)benzyl)oxy)(tert-butyl)dimethylsilane (22)

A round-bottom flask was charged with 21 (0.161 g, 0.63 mmol, 1.0 eq.), imidazole (0.055 g, 0.77 mmol, 1.2 eq.), and $CH_2Cl_2$ (10 mL). Once a solution had formed, tert-butyldimethylsilyl chloride (0.134 g, 0.89 mmol, 1.4 eq.) was added. After stirring overnight at room temperature, the reaction was washed with $H_2O$. The organics were collected and concentrated under reduced pressure. The crude material was purified via flash chromatography on a silica column (2:98 v/v EtOAc:hexanes) to afford the title compound as a colorless oil (0.217 g, 0.588 mmol, 93.1% yield). $^1$H NMR (500 MHz, $CDCl_3$) δ 7.66 (d, J=7.8 Hz, 1H), 7.66 (s, 1H), 7.34 (d, J=8.3 Hz, 1H), 4.72 (s, 2H), 0.95 (s, 9H), 0.11 (s, 6H). $^{13}$C NMR (126 MHz, $CDCl_3$) δ 141.44, 134.86, 130.42, 130.05 (q, J=31.0 Hz), 125.44 (q, J=5.5 Hz), 123.13 (q, J=273.3 Hz), 118.04 (q, J=1.9 Hz), 63.87, 26.00, 18.50, −5.18. $^{19}$F NMR (471 MHz, $CDCl_3$) δ −62.64.

7-Hydroxy-10-(4-(hydroxymethyl)-2-(trifluoromethyl)phenyl)-5,5-dimethyldibenzo[b,e]silin-3(5H)-one (23)

A flame-dried round-bottom flask was charged with 22 (0.367 g, 1.0 mmol, 10 eq.) and anhydrous THF (5 mL). The reaction was cooled to −78° C. and then treated dropwise with 1.7 M t-butyllithium in pentane (0.6 mL, 1.0 mmol, 10 eq.) over 1 minute. After stirring for an additional 8 minutes at −78° C., the reaction was treated dropwise with a solution of 6 (0.050 g, 0.10 mmol, 1.0 eq.) in anhydrous THF (2 mL) over 30 seconds. After 30 more minutes at −78° C., the reaction was warmed to room temperature and stirred for 2 hours. The reaction was treated with 1.0 M HCl in $H_2O$ (3 mL, 3 mmol, 30 eq.) and heated to 50° C. After stirring overnight, the reaction was cooled to room temperature and quenched with brine and diluted with 33:67 v/v iPrOH:$CH_2Cl_2$. The organics were collected, dried over $Na_2SO_4$, and concentrated. The crude material was purified via flash chromatography on a silica column (10:90 v/v MeOH:$CH_2Cl_2$). The crude residue was suspended in $Et_2O$ and filtered. The precipitate was dried under vacuum to afford the title compound as a red solid (0.0314 g, 0.0733 mmol, 73.3% yield). $^1$H NMR (500 MHz, DMSO-$d_6$) δ 10.50 (s, 1H), 7.87 (d, J=1.6 Hz, 1H), 7.74 (dd, J=8.2, 1.4 Hz, 1H), 7.39 (d, J=7.8 Hz, 1H), 7.19 (s, 1H), 6.83 (s, 1H), 6.69 (d, J=11.9 Hz, 2H), 6.56 (d, J=8.8 Hz, 1H), 6.13 (d, J=8.8 Hz, 1H), 5.53 (t, J=5.7 Hz, 1H), 4.70 (d, J=5.6 Hz, 2H), 0.50 (s, 3H), 0.39 (s, 3H). $^{13}$C NMR (126 MHz, DMSO-$d_6$) δ 182.83, 159.24, 152.50, 146.66, 143.93, 140.94, 139.98, 136.36, 135.81, 135.54, 131.87, 131.40, 130.15, 127.61, 127.25 (q, J=29.5 Hz), 126.80, 124.01 (q, J=4.6 Hz), 123.99 (q, J=274.6 Hz), 121.81, 116.90, 61.92, −0.84, −2.47. $^{19}$F NMR (471 MHz, DMSO-$d_6$) δ −57.90. HRMS (ESI$^+$): m/z calculated for [M+H]$^+$=429.1128; found=429.1129.

4-(7-Hydroxy-5,5-dimethyl-3-oxo-3,5-dihydrodibenzo[b, e]silin-10-yl)-3-(trifluoromethyl)benzaldehyde (Probe 3)

A round-bottom flask was charged with 23 (0.0269 g, 0.063 mmol, 1.0 eq.), 2-iodoxybenzoic acid (0.021 g, 0.075 mmol, 1.2 eq.), and DMSO (3 mL). After stirring 1 hour at room temperature, the reaction was quenched with brine. The resulting mixture was poured through over filter paper. The precipitate was purified via flash chromatography on a silica column (2:98 to 10:90 v/v MeOH:CH$_2$Cl$_2$ gradient) to afford the title compound as a red solid (0.0083 g, 0.019 mmol, 31.0% yield). $^1$H NMR (500 MHz, DMSO-$d_6$) δ 10.55 (s, 1H), 10.21 (s, 1H), 8.46 (d, J=1.4 Hz, 1H), 8.32 (dd, J=7.8, 1.5 Hz, 1H), 7.72 (d, J=7.8 Hz, 1H), 7.21 (s, 1H), 6.86 (s, 1H), 6.71 (d, J=8.0 Hz, 1H), 6.67 (d, J=9.5 Hz, 1H), 6.52 (d, J=8.8 Hz, 1H), 6.13 (d, J=10.2 Hz, 1H), 0.51 (s, 3H), 0.40 (s, 3H). $^{19}$F NMR (471 MHz, DMSO-$d_6$) δ −58.37. HRMS (ESI$^+$): m/z calculated for [M+H]$^+$=427.0972; found=427.0977.

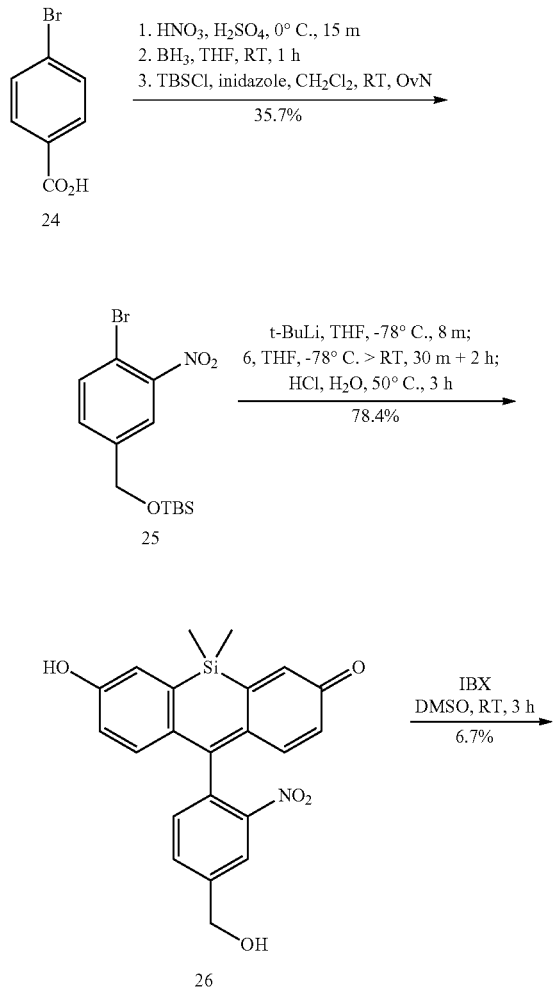

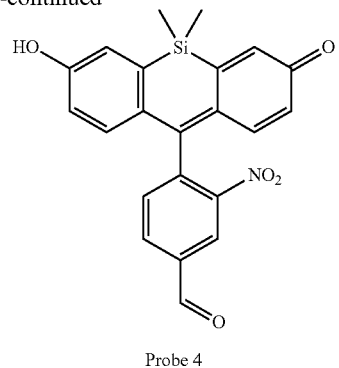

Probe 4

((4-Bromo-3-nitrobenzyl)oxy)(tert-butyl)dimethylsilane (25)

A round-bottom flask was charged with 4-bromobenzoic acid (1.04 g, 5.62 mmol, 1.0 eq.) and H$_2$SO$_4$ (20 mL). The reaction was cooled to 0° C. and the treated dropwise with a solution of HNO$_3$ (0.25 mL, 5.9 mmol, 1.05 eq.) in H$_2$SO$_4$ (3 mL) over 4 minutes. After stirring for 15 minutes at 0° C., the reaction poured over ice. Product was extracted with EtOAc, dried over Na$_2$SO$_4$, and concentrated. The white solid was dissolved in anhydrous THF. While stirring at room temperature, the reaction was treated dropwise with 1.0 M BH$_3$·THF in THF (17 mL, 17 mmol, 3.3 eq.) over 30 seconds. After stirring for 1 hour, the reaction was quenched by slow addition of 1.0 M NaOH in H$_2$O. The mixture was diluted with Et$_2$O. The organics were collected, dried over Na$_2$SO$_4$, and concentrated. The crude residue was treated with imidazole (0.36 g, 5.4 mmol, 1.0 eq.), and CH$_2$Cl$_2$ (10 mL). Once a solution had formed, tert-butyldimethylsilyl chloride (0.82 g, 5.4 mmol, 1.0 eq.) was added. After stirring overnight at room temperature, the reaction was filtered. The crude filtrate was purified via flash chromatography on a silica column (2:98 to 5:95 v/v EtOAc:hexanes gradient) to afford the title compound as a yellow oil (0.695 g, 2.01 mmol, 35.7% yield). $^1$H NMR (500 MHz, CDCl$_3$) δ 7.81 (dd, J=2.0, 0.9 Hz, 1H), 7.68 (d, J=8.2 Hz, 1H), 7.37 (ddd, J=8.2, 2.0, 0.9 Hz, 1H), 4.74 (s, 2H), 0.94 (s, 9H), 0.12 (s, 6H). $^{13}$C NMR (126 MHz, CDCl$_3$) δ 149.91, 143.04, 134.88, 130.51, 123.02, 112.39, 63.44, 26.00, 18.49, −5.19.

7-Hydroxy-10-(4-(hydroxymethyl)-2-nitrophenyl)-5,5-dimethyldibenzo[b, e]silin-3(5H)-one (26)

A flame-dried round-bottom flask was charged with 25 (0.345 g, 1.0 mmol, 10 eq.) and anhydrous THF (5 mL). The reaction was cooled to −78° C. and then treated dropwise with 1.7 M t-butyllithium in pentane (0.60 mL, 1.0 mmol, 10 eq.) over 1 minute. After stirring for an additional 8 minutes at −78° C., the reaction was treated dropwise with a solution of 6 (0.050 g, 0.10 mmol, 1.0 eq.) in anhydrous THF (2 mL) over 30 seconds. 30 minutes after addition, the reaction was warmed to room temperature and stirred for 2 hours. The reaction was treated with 1.0 M HCl in H$_2$O (3 mL, 3.0 mmol, 30 eq.) and heated to 50° C. After stirring for 3 hours, the reaction was cooled to room temperature. The reaction was diluted with CH$_2$Cl$_2$ and THF and washed with brine. The organics were collected, dried over Na$_2$SO$_4$, and concentrated. The crude material was purified via flash chromatography on a silica column 5:95 to 10:90 v/v iPrOH:

CH$_2$Cl$_2$ gradient). The crude material was washed with CH$_2$Cl$_2$ to afford the title compound as a red solid (0.0318 g, 0.0784 mmol, 78.4% yield). $^1$H NMR (500 MHz, DMSO-d$_6$) δ 10.51 (s, 1H), 8.28 (s, 1H), 7.85 (d, J=8.5 Hz, 1H), 7.48 (d, J=7.8 Hz, 1H), 7.02 (s, 2H), 6.69 (d, J=9.3 Hz, 2H), 6.43 (s, 2H), 5.65 (s, 1H), 4.74 (s, 2H), 0.50 (s, 3H), 0.44 (s, 3H). $^{13}$C NMR (126 MHz, DMSO-d$_6$) δ 152.56, 147.71, 145.49, 132.72, 131.93, 131.80, 122.20, 61.58, −1.05, −2.19.

4-(7-Hydroxy-5,5-dimethyl-3-oxo-3,5-dihydrodibenzo[b, e]silin-10-yl)-3-nitrobenzaldehyde (Probe 4)

A round-bottom flask was charged with 26 (0.0164 g, 0.040 mmol, 1.0 eq.), 2-iodoxybenzoic acid (0.0138 g, 0.049 mmol, 1.2 eq.), and DMSO (1 mL). After stirring 3 hours at room temperature, the reaction was concentrated under reduced pressure. The crude material was purified via flash chromatography on a silica column (5:95 v/v iPrOH:CH$_2$Cl$_2$). The resultant solid was washed with CH$_2$Cl$_2$ to afford the title compound as a red solid (0.0011 g, 0.0027 mmol, 6.7% yield). $^1$H NMR (500 MHz, DMSO-d$_6$) δ 10.60 (s, 1H), 8.72 (s, 1H), 8.37 (d, J=7.9 Hz, 1H), 7.63 (d, J=7.9 Hz, 1H), 7.23 (s, 1H), 6.71 (s, 4H), 6.14 (s, 1H), 0.49 (s, 3H), 0.44 (s, 3H). HRMS (ESI$^+$): m/z calculated for [M+H]$^+$=404.0949; found=404.0963.

Scheme 10. Synthesis of Probe 5.

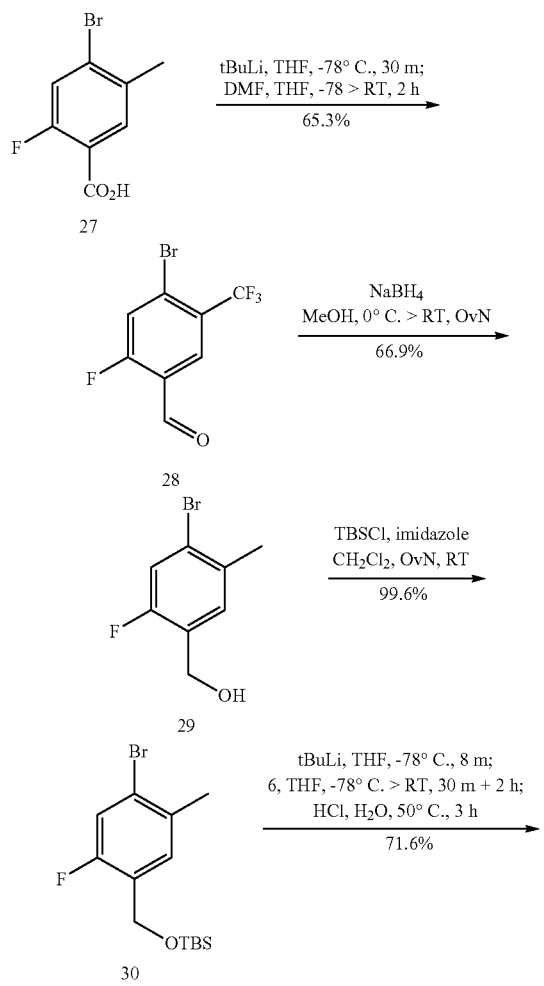

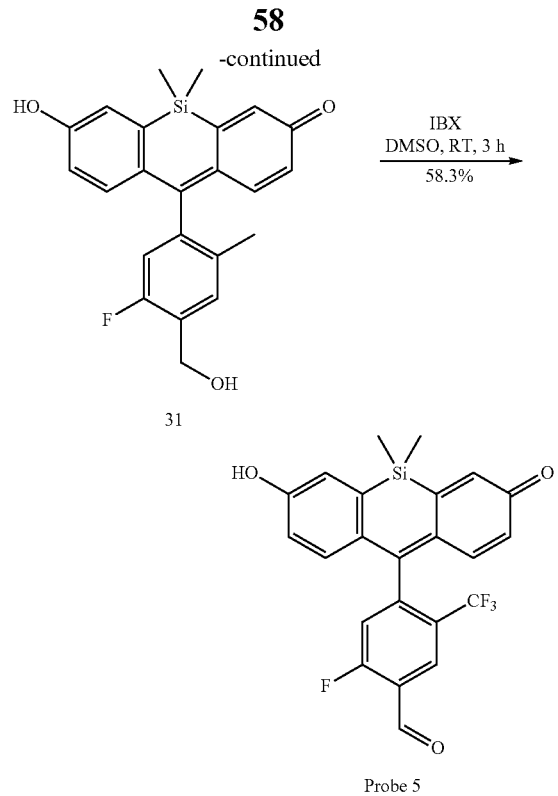

4-Bromo-2-fluoro-5-methylbenzaldehyde (28)

A flame-dried round-bottom flask was charged with 1,4-dibromo-2-fluoro-5-methylbenzene (3.2 g, 12 mmol, 1.0 eq.) and anhydrous THF (30 mL). The reaction was cooled to −78° C. and then treated dropwise with 2.5 M n-butyllithium in hexanes (5.03 mL, 12.6 mmol, 1.05 eq.) over 10 minutes. After stirring an additional 30 minutes at room −78° C., the reaction was treated dropwise with a solution of DMF (1.67 mL, 21.6 mmol, 1.8 eq.) in anhydrous THF (3 mL) over 5 minutes. The reaction was warmed to room temperature. After 2 hours, the reaction was quenched with brine and diluted with EtOAc. The organics were collected, dried over Na$_2$SO$_4$, and concentrated under reduced pressure. The crude material was purified via flash chromatography on a silica column (10:90 v/v CH$_2$Cl$_2$:hexanes) to afford the title compound as a white solid (1.70 g, 7.83 mmol, 65.3% yield). $^1$H NMR (500 MHz, CDCl$_3$) δ 10.29 (s, 1H), 7.71 (d, J=7.3 Hz, 1H), 7.42 (d, J=9.6 Hz, 1H), 2.41 (s, 3H). $^{13}$C NMR (126 MHz, CDCl$_3$) δ 186.58 (d, J=5.8 Hz), 162.27 (d, J=260.3 Hz), 135.12 (d, J=3.9 Hz), 132.53 (d, J=9.7 Hz), 129.56 (d, J=2.4 Hz), 123.09 (d, J=8.2 Hz), 120.78 (d, J=23.2 Hz), 22.20. $^{19}$F NMR (471 MHz, CDCl$_3$) δ −125.06 (t, J=8.5 Hz).

(4-Bromo-2-fluoro-5-methylphenyl)methanol (29)

A round-bottom flask was charged with 38 (0.508 g, 2.34 mmol, 1.0 eq.) were treated with MeOH (10 mL). After cooling to 0° C., the solution was treated with NaBH$_4$ (0.090 g, 2.34 mmol, 1.0 eq.) The reaction was warmed to room temperature. After stirring overnight, the reaction was quenched with sequential addition of H$_2$O (5 mL), 1.0 M NaOH in H$_2$O (5 mL), and more H$_2$O (5 mL). MeOH was removed under reduced pressure. Product was extracted with CH$_2$Cl$_2$. The organics were collected, dried over Na$_2$SO$_4$, and concentrated to afford the title compound as a colorless oil (0.343 g, 1.57 mmol, 66.9% yield). $^1$H NMR (500 MHz, CDCl$_3$) δ 7.29 (d, J=7.8 Hz, 1H), 7.26 (d, J=9.3 Hz, 1H), 4.69 (s, 2H), 2.36 (s, 3H). $^{13}$C NMR (126 MHz, CDCl$_3$) δ 158.42 (d, J=248.1 Hz), 133.98 (d, J=3.7 Hz), 130.81 (d, J=4.8 Hz), 126.92 (d, J=14.7 Hz), 123.71 (d, J=9.6 Hz), 119.40 (d, J=24.5 Hz), 59.08 (d, J=3.8 Hz), 22.18. $^{19}$F NMR (471 MHz, CDCl$_3$) δ −122.30 (t, J=8.7 Hz).

((4-Bromo-2-fluoro-5-methylbenzyl)oxy) (tert-butyl) dimethylsilane (30)

A round-bottom flask was charged with 39 (0.219 g, 1.0 mmol, 1.0 eq.), imidazole (0.136 g, 2.0 mmol, 2.0 eq.), and CH$_2$Cl$_2$ (10 mL). Once a solution had formed, tert-butyldimethylsilyl chloride (0.301 g, 2.0 mmol, 2.0 eq.) was added. After stirring overnight at room temperature, the reaction was washed with 1.0 M HCl in H$_2$O. The organics were collected, dried over Na$_2$SO$_4$, and concentrated under reduced pressure to afford the title compound as a colorless oil (0.332 g, 0.996 mmol, 99.6% yield). $^1$H NMR (500 MHz, CDCl$_3$) δ 7.32 (d, J=7.8 Hz, 1H), 7.20 (d, J=9.3 Hz, 1H), 4.70 (s, 2H), 2.36 (s, 3H), 0.94 (s, 9H), 0.11 (s, 6H). $^{13}$C NMR (126 MHz, CDCl$_3$) δ 157.66 (d, J=247.3 Hz), 133.59 (d, J=3.4 Hz), 129.98 (d, J=5.2 Hz), 127.66 (d, J=14.4 Hz), 122.65 (d, J=9.2 Hz), 118.88 (d, J=24.4 Hz), 58.76 (d, J=4.3 Hz), 26.06, 22.31, 18.57, −5.21. $^{19}$F NMR (471 MHz, CDCl$_3$) δ −122.56 (t, J=8.6 Hz).

10-(5-Fluoro-4-(hydroxymethyl)-2-methylphenyl)-7-hydroxy-5,5-dimethyldibenzo[b,e]silin-3(5H)-one (31)

A flame-dried round-bottom flask was charged with 40 (0.334 g, 1.0 mmol, 10 eq.) and anhydrous THF (5 mL). The reaction was cooled to −78° C. and then treated dropwise with 1.7 M t-butyllithium in pentane (0.59 mL, 1.0 mmol, 10 eq.) over 1 minute. After stirring for an additional 8 minutes at −78° C., the reaction was treated dropwise with a solution of 6 (0.051 g, 0.10 mmol, 1.0 eq.) in anhydrous THF (2 mL) over 1 minute. After addition, the reaction was warmed to room temperature and stirred for 2 hours. The reaction was treated with 1.0 M HCl in H$_2$O (3 mL, 3 mmol, 30 eq.) and heated to 50° C. After stirring for 3 hours, the reaction was cooled to room temperature and quenched with brine. The organics were collected, dried over Na$_2$SO$_4$, and concentrated. The crude material was purified via flash chromatography on a silica column (2:98 v/v MeOH:CH$_2$Cl$_2$). The crude residue was dissolved in CH$_2$Cl$_2$, triturated with hexanes, and collected by filtration to afford the title compound as a red solid (0.0281 g, 0.0716 mmol, 71.6% yield). $^1$H NMR (500 MHz, DMSO-d$_6$) δ 10.52 (s, 1H), 7.47 (d, J=7.4 Hz, 1H), 7.18 (s, 1H), 7.03 (d, J=10.1 Hz, 1H), 6.77 (s, 4H), 6.19 (s, 1H), 5.35 (t, J=5.7 Hz, 1H), 4.62 (d, J=5.3 Hz, 2H), 1.96 (s, 3H), 0.47 (s, 3H), 0.44 (s, 3H). $^{13}$C NMR (126 MHz, DMSO-d$_6$) δ 157.66 (d, J=244.5 Hz), 139.18 (d, J=7.6 Hz), 131.14 (d, J=3.3 Hz), 130.59 (d, J=4.8 Hz), 128.81 (d, J=15.0 Hz), 115.60 (d, J=22.2 Hz), 56.62 (d, J=3.6 Hz), 18.25, −1.33, −1.65. $^{19}$F NMR (471 MHz, DMSO-d$_6$) δ −124.04 (t, J=8.8 Hz). HRMS (ESI$^+$): m/z calculated for [M+H]$^+$=393.1317; found=393.1321.

2-Fluoro-4-(7-hydroxy-5,5-dimethyl-3-oxo-3,5-dihydrodibenzo[b, e]silin-10-yl)-5-methylbenzaldehyde (Probe 5)

A round-bottom flask was charged with 41 (0.0069 g, 0.018 mmol, 1.0 eq.), 2-iodoxybenzoic acid (0.0060 g, 0.021 mmol, 1.2 eq.), and DMSO (1 mL). After stirring 3 hours at room temperature, the reaction was concentrated. The crude material was purified via flash chromatography on a silica column (5:95 v/v iPrOH:CH$_2$Cl$_2$) to afford the title compound as a red solid (0.0040 g, 0.0102 mmol, 58.3% yield). $^1$H NMR (500 MHz, DMSO-d$_6$) δ 10.57 (s, 1H), 10.29 (s, 1H), 7.87 (d, J=6.8 Hz, 1H), 7.38 (d, J=10.5 Hz, 1H), 7.22 (d, J=2.7 Hz, 1H), 6.85 (s, 1H), 6.80 (d, J=10.4 Hz, 1H), 6.75 (d, J=7.8 Hz, 1H), 6.67 (d, J=8.6 Hz, 1H), 6.17 (d, J=10.1 Hz, 1H), 2.03 (s, 3H), 0.48 (s, 3H), 0.45 (s, 3H). $^{13}$C NMR (126 MHz, DMSO-d$_6$) δ 187.58, 182.82, 161.48 (d, J=257.5 Hz), 159.62 (d, J=1.8 Hz), 152.52, 147.70 (d, J=8.8 Hz), 146.58, 140.54, 140.16, 136.66, 134.78, 132.71 (d, J=3.2 Hz), 130.57, 130.01, 127.51, 126.48, 123.29 (d, J=8.0 Hz), 122.30, 117.66 (d, J=20.7 Hz), 117.29, 18.00, −1.36, −1.64. $^{19}$F NMR (471 MHz, DMSO-d$_6$) δ −124.88 (dd, J=10.5, 7.1 Hz). HRMS (ESI$^+$): m/z calculated for [M+H]$^+$=391.1160; found=391.1163.

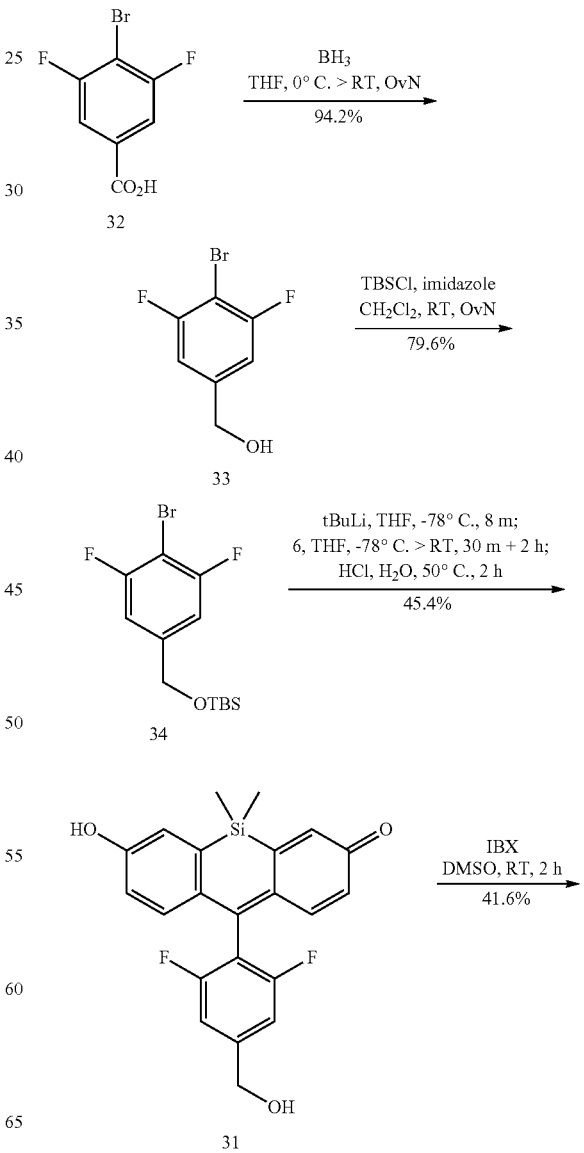

Scheme 11. Synthesis of Probe 6.

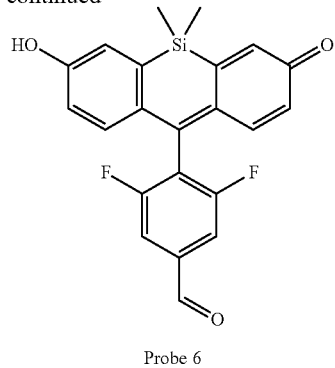

Probe 6

(4-Bromo-3,5-difluorophenyl)methanol (33)

A round-bottom flask was charged with 4-bromo-3,5-difluorobenzoic acid (0.234 g, 1.0 mmol, 1.0 eq.) and anhydrous THF (10 mL). The solution was cooled to 0° C. and then treated dropwise with 1.0 M $BH_3$-THF in THF (3.0 mL, 3.0 mmol, 3.0 eq.) over 3 minutes. The reaction was removed from the cold bath. After stirring at room temperature overnight, the reaction was cooled to 0° C. and quenched with $H_2O$. The THF was removed under reduced pressure. Product was extracted with EtOAc. The organics were collected, washed with brine, dried over $Na_2SO_4$, and concentrated. The crude material was purified via flash chromatography on a silica column (25:75 to 50:50 v/v EtOAc:hexanes gradient) to afford the title compound as a white solid (0.210 g, 0.942 mmol, 94.2% yield). $^1$H NMR (500 MHz, $CDCl_3$) δ 6.97 (d, J=7.0 Hz, 2H), 4.67 (s, 2H), 1.91 (s, 1H). $^{13}$C NMR (126 MHz, $CDCl_3$) δ 160.13 (dd, J=249.2, 4.5 Hz), 143.27 (t, J=8.1 Hz), 111.98-108.81 (m), 96.48 (t, J=24.5 Hz), 63.78 (t, J=2.0 Hz). $^{19}$F NMR (471 MHz, $CDCl_3$) δ -105.06 (d, J=7.1 Hz).

((4-Bromo-3,5-difluorobenzyl)oxy) (tert-butyl)dimethylsilane (34)

A round-bottom flask was charged with 34 (0.492 g, 2.21 mmol, 1.0 eq.) imidazole (0.165 g, 2.4 mmol, 1.1 eq.) and $CH_2Cl_2$ (10 mL). Once a solution had formed, tert-butyldimethylsilyl chloride (0.365 g, 2.4 mmol, 1.1 eq.) was added. After stirring overnight at room temperature, the reaction was filtered. The filtrate was washed with 1.0 M HCl in $H_2O$, dried over $Na_2SO_4$, and concentrated under reduced pressure to afford the title compound as a colorless oil (0.592 g, 1.76 mmol, 79.6% yield). $^1$H NMR (500 MHz, $CDCl_3$) δ 6.93 (d, J=7.8 Hz, 2H), 4.67 (s, 2H), 0.94 (s, 9H), 0.11 (s, 6H). $^{13}$C NMR (126 MHz, $CDCl_3$) δ 160.01 (dd, J=248.4, 4.5 Hz), 144.23 (t, J=8.1 Hz), 109.40-108.88 (m), 95.65 (t, J=24.7 Hz), 63.70 (t, J=2.1 Hz), 26.00, 18.50, -5.22. $^{19}$F NMR (471 MHz, $CDCl_3$) δ -105.65 (d, J=7.1 Hz).

10-(2,6-Difluoro-4-(hydroxymethyl)phenyl)-7-hydroxy-5,5-dime thyldibenzo[b, e]silin-3(5H)-one (35)

A flame-dried round-bottom flask was charged with 35 (0.340 g, 1.0 mmol, 10 eq.) and anhydrous THF (5 mL). The reaction was cooled to -78° C. and then treated dropwise with 1.7 M t-butyllithium in pentane (0.60 mL, 1.0 mmol, 1.0 eq.) over 5 minutes. After stirring for an additional 8 minutes at -78° C., the reaction was treated dropwise with a solution of 6 (0.050 g, 0.10 mmol, 1.0 eq.) in anhydrous THF (3 mL) over 4 minutes. After addition, the reaction was warmed to room temperature and stirred for 2 hours. The reaction was treated with 3.0 M HCl (1.0 mL, 3.0 mmol, 30 eq.) and heated to 50° C. After stirring for 2 hours, the reaction was cooled to room temperature and quenched with brine. The organics were collected, dried over $Na_2SO_4$, and concentrated. The crude material was purified via flash chromatography on a silica column (5:95 v/v MeOH:$CH_2Cl_2$ gradient) to afford the title compound as a red solid (0.018 g, 0.0454 mmol, 45.4% yield). $^1$H NMR (500 MHz, Methanol-$d_4$) δ 7.19 (d, J=8.1 Hz, 2H), 7.05 (s, 2H), 7.03 (d, J=5.2 Hz, 2H), 6.50 (d, J=9.4 Hz, 2H), 4.74 (s, 2H), 0.50 (s, 6H). $^{13}$C NMR (126 MHz, Methanol-$d_4$) δ 161.04 (dd, J=246.8, 7.4 Hz), 148.71 (d, J=8.6 Hz), 147.83, 131.39, 115.64 (t, J=22.1 Hz), 111.97-106.78 (m), 63.77, -1.50. $^{19}$F NMR (471 MHz, Methanol-$d_4$) δ -114.31 (d, J=8.1 Hz). HRMS (ESI$^+$): m/z calculated for [M+H]$^+$=397.1066; found=397.1070.

3,5-Difluoro-4-(7-hydroxy-5,5-dimethyl-3-oxo-3,5-dihydrodibenzo[b, e]silin-10-yl)benzaldehyde (Probe 6)

A round-bottom flask was charged with 36 (0.0157 g, 0.040 mmol, 1.0 eq.), 2-iodoxybenzoic acid (0.014 g, 0.048 mmol, 1.2 eq.), and DMSO (1 mL). After stirring 2 hours at room temperature, the reaction was concentrated. The crude material was purified via flash chromatography on a silica column (5:95 v/v iPrOH:$CH_2Cl_2$) to afford the title compound as a red solid (0.0065 g, 0.0165 mmol, 41.6% yield). $^1$H NMR (500 MHz, $CDCl_3$) δ 10.05 (t, J=1.6 Hz, 1H), 7.61 (d, J=6.0 Hz, 2H), 7.03 (d, J=2.5 Hz, 2H), 6.89 (dt, J=9.4, 1.0 Hz, 2H), 6.55 (dd, J=9.5, 2.4 Hz, 2H), 0.46 (s, 6H). $^{13}$C NMR (126 MHz, $CDCl_3$) δ 188.90, 160.41 (dd, J=252.7, 6.3 Hz), 144.37, 142.98, 138.84 (t, J=7.3 Hz), 137.48, 130.61, 129.90, 123.05, 122.75 (t, J=22.1 Hz), 112.98-112.28 (m), -1.30. $^{19}$F NMR (471 MHz, $CDCl_3$) δ -107.90 (d, J=6.1 Hz). HRMS (ESI$^+$): m/z calculated for [M+H]$^+$=395.0910; found=395.0916.

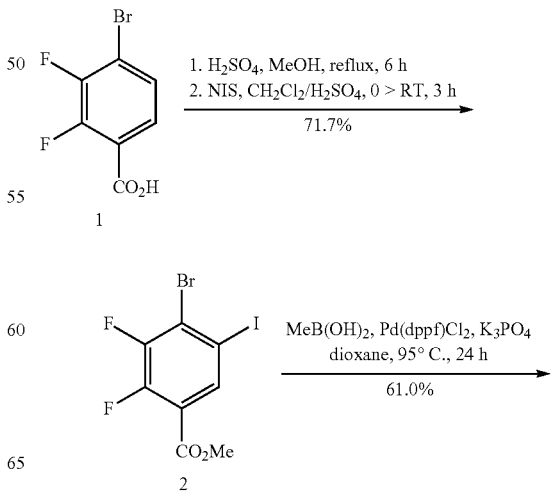

Scheme 12. Synthesis of red-AlDeSense.

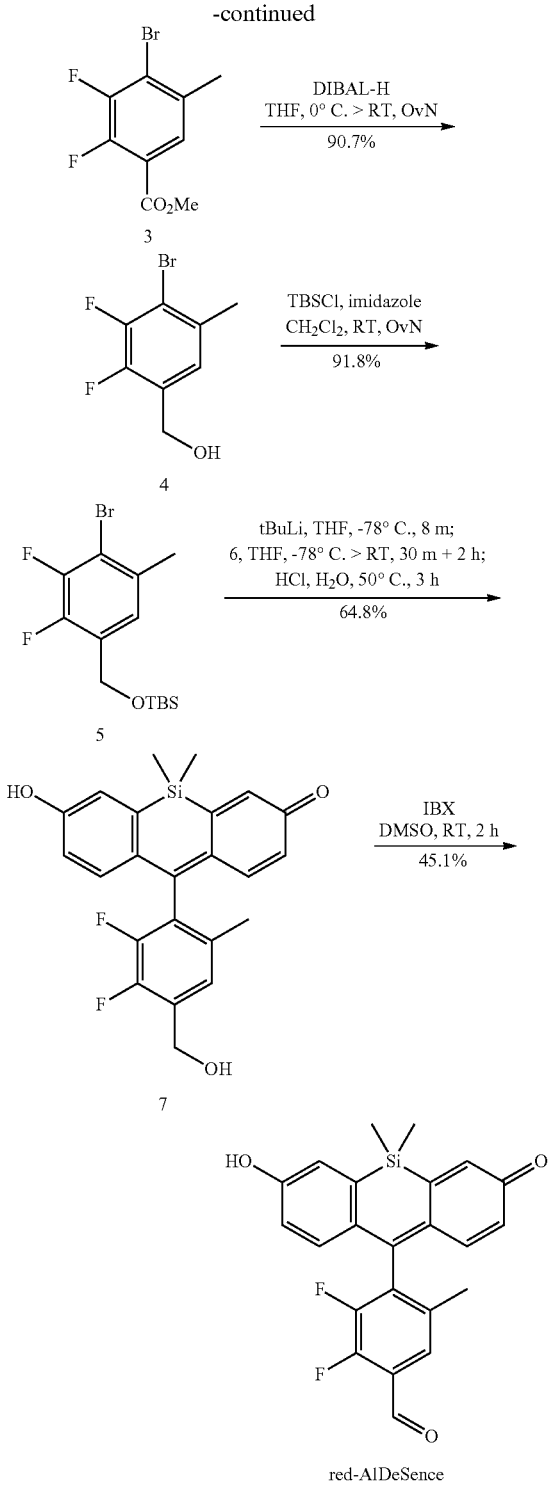

Methyl 4-bromo-2,3-difluoro-5-iodobenzoate (2)

A round-bottom flask was charged with 4-bromo-2,3-difluorobenzoic acid (1.00 g, 4.22 mmol, 1.0 eq.) and MeOH (5 mL). The reaction was cooled to 0° C. and then treated dropwise with conc. H2SO$_4$ (1 mL) over 30 seconds. The reaction was heated to reflux. After 6 hours, the reaction was poured into H$_2$O and diluted with EtOAc. The organics were collected, washed with 1.0 M NaOH in H$_2$O, dried over Na$_2$SO$_4$, and concentrated under reduced pressure. The material was dissolved in CH$_2$Cl$_2$ (4 mL) and cooled to 0° C. The reaction was treated dropwise with conc. H2SO$_4$ (4 mL) over 2 minutes. While still cold, the reaction was treated portionwise with N-iodosuccinimide (1.41 g, 6.3 mmol, 1.5 eq.) over 2 minutes. The reaction was warmed to room temperature. After stirring for 3 hours, the reaction was quenched via addition of ice. The organics were collected, washed with saturated NaHCO$_3$, washed with aqueous Na$_2$S$_2$O$_3$, dried over Na$_2$SO$_4$, and concentrated. The crude material was purified via flash chromatography on a silica column (10:90 v/v CH$_2$Cl$_2$:hexanes) to afford the title compound as a white solid (1.14 g, 3.02 mmol, 71.7% yield). $^1$H NMR (500 MHz, CDCl$_3$) δ 8.21 (dd, J=6.4, 1.3 Hz, 1H), 3.94 (s, 3H). $^{13}$C NMR (126 MHz, CDCl$_3$) δ 162.38 (t, J=3.4 Hz), 150.25 (dd, J=267.8, 15.4 Hz), 148.70 (dd, J=253.4, 15.2 Hz), 136.20 (d, J=4.0 Hz), 124.04 (d, J=18.7 Hz), 120.69 (d, J=8.0 Hz), 94.51 (dd, J=5.1, 2.5 Hz), 53.12. $^{19}$F NMR (471 MHz, CDCl$_3$) δ −116.92 (d, J=21.2 Hz), −130.87 (dd, J=21.1, 6.6 Hz).

Methyl 4-bromo-2,3-difluoro-5-methylbenzoate (3)

A pressure flask was charged with 2 (0.900 g, 2.39 mmol, 1.0 eq.), methylboronic acid (0.286 g, 4.78 mmol, 2.0 eq.), K3PO$_4$ (1.01 g, 4.78 mmol, 2.0 eq.), and anhydrous 1,4-dixoane (10 mL). The mixture was degassed for 15 minutes via concurrent sparging with N$_2$ and sonication before being treated with Pd(dppf)C$_{12}$ (0.053 g, 0.072 mmol, 0.03 eq.). The reaction was sealed and heated to 95° C. After stirring for 24 hours, the reaction was cooled, poured into H$_2$O. Product was extracted with Et$_2$O. The organics were combined, washed with H$_2$O, dried over Na$_2$SO$_4$, and concentrated. The crude material was purified via flash chromatography on a silica column (10:90 v/v CH$_2$Cl$_2$:hexanes) to afford the title compound as a white solid (0.386 g, 1.46 mmol, 61.0% yield). $^1$H NMR (500 MHz, CDCl$_3$) δ 7.59 (dd, J=6.7, 2.1 Hz, 1H), 3.93 (s, 3H), 2.40 (s, 3H). $^{13}$C NMR (126 MHz, CDCl$_3$) δ 163.80 (t, J=3.6 Hz), 148.63 (dd, J=247.9, 14.8 Hz), 148.51 (dd, J=263.8, 15.4 Hz), 134.65 (d, J=4.5 Hz), 126.62 (d, J=3.4 Hz), 118.52 (d, J=7.3 Hz), 117.99 (d, J=17.4 Hz), 52.77, 22.12 (d, J=2.3 Hz). $^{19}$F NMR (471 MHz, CDCl$_3$) δ −125.94 (dd, J=21.7, 2.5 Hz), −135.08 (dd, J=21.4, 6.7 Hz).

(4-Bromo-2,3-difluoro-5-methylphenyl)methanol (4)

A flame-dried round-bottom flask was charged with 3 (0.386 g, 1.46 mmol, 1.0 eq.) and anhydrous THF (10 mL). The reaction was cooled to 0° C. before treating dropwise with 1.0 M DIBAL-H in hexanes (3.2 g, 3.2 mmol, 2.2 eq.) over 3 minutes. The reaction was slowly warmed to room temperature with the melting ice bath. After stirring overnight, the reaction was concentrated and resuspended in 1.0 M NaOH in H$_2$O. Product was extracted with Et$_2$O, dried over Na$_2$SO$_4$, and concentrated to afford the title compound as a white solid (0.313 g, 1.32 mmol, 90.7% yield). $^1$H NMR (500 MHz, CDCl$_3$) δ 7.12 (dd, J=6.8, 2.0 Hz, 1H), 4.73 (d, J=4.9 Hz, 2H), 2.39 (s, 3H), 1.84 (t, J=6.1 Hz, 1H). $^{13}$C NMR (126 MHz, CDCl$_3$) δ 147.74 (dd, J=247.0, 14.3 Hz), 146.70 (dd, J=249.0, 14.4 Hz), 134.76 (d, J=4.2 Hz), 128.30 (d, J=11.6 Hz), 124.23 (t, J=3.4 Hz), 111.74 (d, J=17.2 Hz), 58.78 (dd, J=3.7, 2.7 Hz), 22.26 (d, J=2.4 Hz). $^{19}$F NMR (471 MHz, CDCl$_3$) δ −128.37 (dd, J=21.7, 2.5 Hz), −144.51 (dd, J=21.9, 6.7 Hz).

((4-Bromo-2,3-difluoro-5-methylbenzyl)oxy) (tert-butyl)dimethylsilane (5)

A round-bottom flask was charged with 4 (0.313 g, 1.32 mmol, 1.0 eq.), imidazole (0.111 g, 1.6 mmol, 1.2 eq.), and $CH_2Cl_2$ (10 mL). Once a solution had formed, tert-butyldimethylsilyl chloride (0.235 g, 1.6 mmol, 1.2 eq.) was added. After stirring overnight at room temperature, the reaction was washed with 1.0 M HCl in $H_2O$. The organics were collected, dried over $Na_2SO_4$, and concentrated under reduced pressure to afford the title compound as a colorless oil (0.426 g, 1.21 mmol, 91.8% yield). $^1$H NMR (500 MHz, $CDCl_3$) δ 7.14 (dd, J=7.1, 2.0 Hz, 1H), 4.74 (s, 2H), 2.39 (s, 3H), 0.95 (s, 9H), 0.13 (s, 6H). $^{13}$C NMR (126 MHz, $CDCl_3$) δ 147.48 (dd, J=246.3, 14.2 Hz), 146.02 (dd, J=248.2, 14.4 Hz), 134.29 (d, J=4.1 Hz), 129.08 (d, J=11.4 Hz), 123.51 (t, J=3.5 Hz), 110.73 (d, J=17.1 Hz), 58.64 (dd, J=4.0, 2.9 Hz), 26.01, 22.35 (d, J=2.3 Hz), 18.53, −5.26. $^{19}$F NMR (471 MHz, $CDCl_3$) δ −129.36 (dd, J=22.0, 2.2 Hz), −144.86 (dd, J=21.8, 6.9 Hz).

10-(3,6-Difluoro-4-(hydroxymethyl)-2-methylphenyl)-7-hydroxy-5,5-dimethyldibenzo[b,e]silin-3(5H)-one (7)

A flame-dried round-bottom flask was charged with 5 (0.352 g, 1.0 mmol, 10 eq.) and anhydrous THF (5 mL). The reaction was cooled to −78° C. and then treated dropwise with 1.7 M t-butyllithium in pentane (0.59 mL, 1.0 mmol, 10 eq.) over 1 minute. After stirring for an additional 8 minutes at −78° C., the reaction was treated dropwise with a solution of 6 (0.052 g, 0.10 mmol, 1.0 eq.) in anhydrous THF (2 mL) over 30 seconds. After addition, the reaction was warmed to room temperature and stirred for 2 hours. The reaction was treated with 1.0 M HCl in $H_2O$ (3 mL, 3 mmol, 30 eq.) and heated to 50° C. After stirring for 3 hours, the reaction was cooled to room temperature and quenched with brine. The organics were collected, dried over $Na_2SO_4$, and concentrated. The crude material was purified via flash chromatography on a silica column (5:95 to 10:95 v/v $MeOH:CH_2Cl_2$ gradient). The crude material was further purified via flash chromatography on a silica column ($Et_2O$) to afford the title compound as a red solid (0.0266 g, 0.0648 mmol, 64.8% yield). $^1$H NMR (500 MHz, Methanol-$d_4$) δ 7.33 (d, J=6.1 Hz, 1H), 7.06 (d, J=2.5 Hz, 2H), 6.97 (d, J=9.4 Hz, 2H), 6.51 (d, J=8.7 Hz, 2H), 4.79 (s, 2H), 2.05 (s, 3H), 0.54 (s, 3H), 0.51 (s, 3H). $^{19}$F NMR (471 MHz, Methanol-$d_4$) δ −142.01 (d, J=21.7 Hz), −149.82 (dd, J=21.7, 6.4 Hz). HRMS (ESI$^+$): m/z calculated for [M+H]$^+$=411.1223; found=411.1226.

2,5-Difluoro-4-(7-hydroxy-5,5-dimethyl-3-oxo-3,5-dihydrodibenzo[b, e]silin-10-yl)-3-methylbenzaldehyde (red-AlDeSense aka Probe 7)

A round-bottom flask was charged with 7 (0.0259 g, 0.063 mmol, 1.0 eq.), 2-iodoxybenzoic acid (0.0214 g, 0.076 mmol, 1.2 eq.), and DMSO (1 mL). After stirring 2 hours at room temperature, the reaction was concentrated. The crude material was purified via flash chromatography on a silica column (5:95 v/v $iPrOH:CH_2Cl_2$) to afford the title compound as a red solid (0.0116 g, 0.0284 mmol, 45.1% yield). $^1$H NMR (500 MHz, $CDCl_3$) δ 10.41 (s, 1H), 7.63 (d, J=5.4 Hz, 1H), 7.05 (d, J=2.5 Hz, 2H), 6.83 (d, J=9.4 Hz, 2H), 6.56 (dd, J=9.5, 2.4 Hz, 2H), 2.09 (s, 3H), 0.47 (s, 3H), 0.45 (s, 3H). $^{13}$C NMR (126 MHz, $CDCl_3$) δ 185.76, 171.89, 150.99 (dd, J=261.5, 14.4 Hz), 148.04, 147.71 (dd, J=249.6, 12.5 Hz), 144.72, 137.45, 135.42 (d, J=14.1 Hz), 134.27 (d, J=3.9 Hz), 129.92, 129.68, 125.21 (d, J=5.3 Hz), 124.02 (d, J=3.6 Hz), 123.14, 18.98 (d, J=1.8 Hz), −1.24, −1.44. $^{19}$F NMR (471 MHz, $CDCl_3$) δ −136.14 (d, J=22.2 Hz), −149.06 (dd, J=22.4, 5.9 Hz). HRMS (ESI$^+$): m/z calculated for [M+H]$^+$=409.1066; found=409.1071.

Scheme 13. Synthesis of Probe 8.

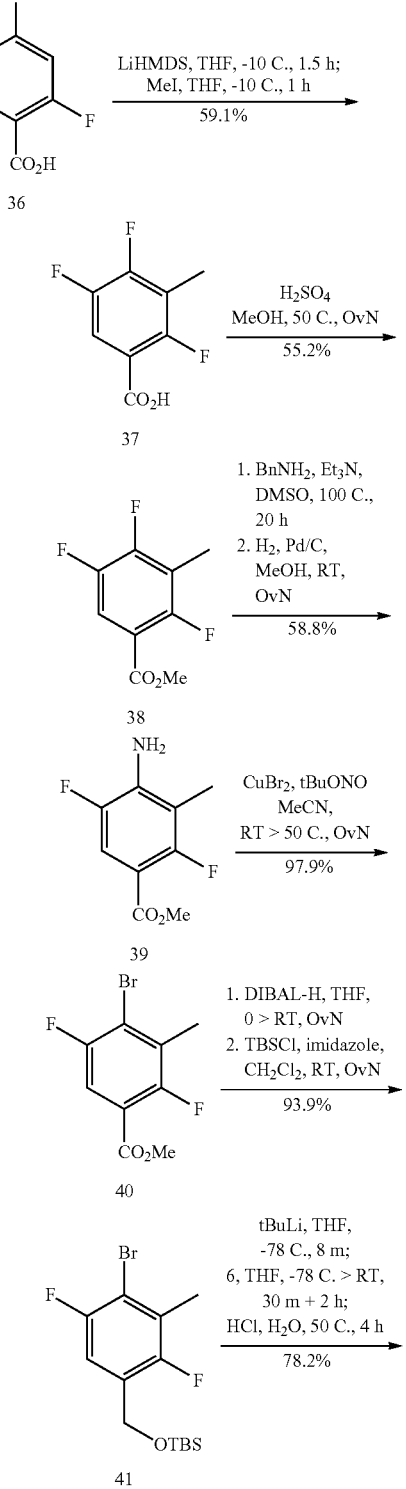

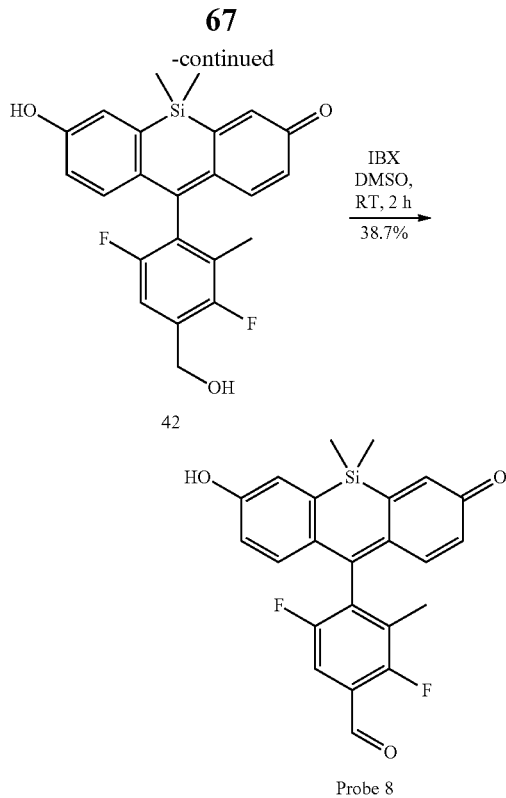

2,4,5-Trifluoro-3-methylbenzoic acid (37)

A round-bottom flask was charged with anhydrous THF (6 mL) and 1.0 M LiHMDS in THF (6.5 mL, 6.5 mmol, 2.3 eq.). The solution was cooled to −10° C. and then treated dropwise with a solution of 2,4,5-trifluorobenzoic acid (0.503 g, 2.8 mmol, 1.0 eq.) in anhydrous THF (3 mL) over 4 minutes. After stirring for 1.5 hours, the reaction was treated dropwise with methyl iodide (0.193 mL, 3.1 mmol, 1.1 eq.). After stirring for 1 hour, the reaction was quenched with cold 3 M HCl (2 mL) followed by cold 6 M HCl (2.5 mL) and warmed to room temperature. The THF was removed under reduced pressure. Product was extracted with EtOAc. The organics were collected, dried over $Na_2SO_4$, and concentrated. The crude residue was recrystallized in $H_2O$ to afford the title compound as a white solid (0.321 g, 1.69 mmol, 59.1% yield). $^1$H NMR (500 MHz, $CDCl_3$) δ 7.70 (td, J=9.5, 6.6 Hz, 1H), 2.29 (t, J=2.3 Hz, 3H). $^{13}$C NMR (126 MHz, $CDCl_3$) δ 167.64, 157.44 (ddd, J=259.7, 7.2, 2.4 Hz), 152.89 (ddd, J=256.8, 14.1, 8.6 Hz), 146.54 (ddd, J=246.4, 13.6, 3.5 Hz), 117.38 (dd, J=23.4, 17.5 Hz), 117.00 (dt, J=20.5, 1.9 Hz), 113.05 (ddd, J=11.7, 5.5, 4.0 Hz), 7.77 (dt, J=3.8, 1.9 Hz). $^{19}$F NMR (471 MHz, $CDCl_3$) δ −112.01−−112.19 (m), −126.87−−127.01 (m), −141.35 (ddd, J=21.8, 16.3, 10.3 Hz).

Methyl 2,4,5-trifluoro-3-methylbenzoate (38)

A round-bottom flask was charged with 43 (3.58 g, 18.8 mmol, 1.0 eq.), MeOH (40 mL), and conc. H2SO4 (2 mL). The reaction was heated to 50° C. After stirring overnight, the reaction was neutralized with saturated $NaHCO_3$ and diluted with EtOAc. The organics were collected, dried over $Na_2SO_4$, and concentrated. The crude material was purified via flash chromatography on a silica column (5:95 v/v EtOAc:hexanes) to afford the title compound as a colorless oil (2.12 g, 10.4 mmol, 55.2% yield). $^1$H NMR (400 MHz, $CDCl_3$) δ 7.61 (td, J=9.3, 6.6 Hz, 1H), 3.92 (s, 3H), 2.26 (t, J=2.2 Hz, 3H). $^{19}$F NMR (376 MHz, $CDCl_3$) δ −114.06−−114.71 (m), −129.48 (dt, J=19.4, 9.3 Hz), −142.34 (ddd, J=22.0, 16.0, 10.1 Hz).

Methyl 4-amino-2,5-difluoro-3-methylbenzoate (39)

A pressure flask was charged with 44 (0.97 g, 5.0 mmol, 1.0 eq.), benzylamine (0.65 mL, 6.0 mmol, 1.2 eq.), triethylamine (1.03 mL, 7.4 mmol, 1.5 eq.), and DMSO (2 mL). The reaction was heated to 100° C. for 20 hours. After cooling to room temperature, the reaction was poured into brine and diluted with EtOAc. The organics were washed with more brine, dried over $Na_2SO_4$, and concentrated under reduced pressure. To the crude residue was added 10% w/w Pd/C (0.069 g) and MeOH (20 mL). The mixture was stirred vigorously under hydrogen (1 atm) overnight at room temperature. The reaction filtered through Celite®. The crude material was purified via flash chromatography on a silica column (10:90 v/v EtOAc:hexanes) to afford the title compound as a white solid (0.579 g, 2.88 mmol, 58.8% yield). $^1$H NMR (500 MHz, $CDCl_3$) δ 7.41 (dd, J=11.4, 6.4 Hz, 1H), 4.17 (s, 2H), 3.84 (s, 3H), 2.06 (d, J=2.4 Hz, 3H). $^{13}$C NMR (126 MHz, $CDCl_3$) δ 164.63 (dd, J=4.4, 2.4 Hz), 157.46 (dd, J=252.7, 1.2 Hz), 146.09 (dd, J=234.7, 2.1 Hz), 139.30 (dd, J=14.1, 8.3 Hz), 114.57 (dd, J=22.3, 3.1 Hz), 110.90 (dd, J=22.4, 3.4 Hz), 106.06 (dd, J=13.2, 7.0 Hz), 51.97, 8.67 (dd, J=6.8, 2.4 Hz). $^{19}$F NMR (471 MHz, $CDCl_3$) δ −116.80 (ddd, J=15.5, 6.1, 2.1 Hz), −140.73 (dd, J=16.0, 11.4 Hz).

Methyl 4-bromo-2,5-difluoro-3-methylbenzoate (40)

A flame-dried round-bottom flask was charged with 45 (0.310 g, 1.54 mmol, 1.0 eq.), $CuBr_2$ (1.72 g, 7.7 mmol, 5.0 eq.), and anhydrous MeCN (10 mL). The reaction was treated with tert-butyl nitrite (0.28 mL, 2.3 mmol, 1.5 eq.) and heated to 50° C. After stirring overnight, the reaction was cooled and diluted with saturated $NaHCO_3$. Product was extracted with EtOAc. The organics were combined, dried over $Na_2SO_4$, and concentrated to afford the title compound as a yellow solid (0.40 g, 1.51 mmol, 97.9% yield). $^1$H NMR (500 MHz, $CDCl_3$) δ 7.54 (dd, J=8.3, 6.0 Hz, 1H), 3.93 (s, 3H), 2.41 (d, J=2.9 Hz, 3H). $^{13}$C NMR (126 MHz, $CDCl_3$) δ 163.62 (dd, J=4.3, 2.3 Hz), 156.27 (dd, J=123.6, 3.1 Hz), 154.28 (dd, J=109.3, 3.1 Hz), 129.33 (d, J=21.2 Hz), 118.01 (dd, J=22.2, 5.2 Hz), 117.90 (dd, J=13.6, 7.1 Hz), 115.17 (dd, J=26.8, 1.9 Hz), 52.70, 15.08 (dd, J=4.9, 2.2 Hz). $^{19}$F NMR (471 MHz, $CDCl_3$) δ −109.15 (dd, J=16.9, 8.2 Hz), −113.13 (ddq, J=16.6, 5.9, 2.7 Hz).

((4-Bromo-2,5-difluoro-3-methylbenzyl)oxy) (tert-butyl)dimethylsilane (41)

A flame-dried round-bottom flask was charged with 46 (0.525 g, 2.0 mmol, 1.0 eq.) and anhydrous THF (10 mL). The reaction was cooled to 0° C. before treating dropwise with 1.0 M DIBAL-H in $CH_2Cl_2$ (5.0 mL, 5.0 mmol, 2.5 eq.) over 2 minutes. The reaction was slowly warmed to room temperature with the melting ice bath. After stirring overnight minutes, the reaction was quenched via the sequential addition of $H_2O$ (5 mL), 1.0 M NaOH in $H_2O$ (5 mL), and more $H_2O$ (5 mL). The reaction was diluted with $Et_2O$. The organics were collected, dried over $Na_2SO_4$, and concentrated. The crude residue was treated imidazole (0.21 g, 3.0 mmol, 1.5 eq.) and $CH_2Cl_2$ (20 mL). Once a solution had formed, tert-butyldimethylsilyl chloride (0.47 g, 3.0 mmol, 1.5 eq.) was added. After stirring overnight at room temperature, the reaction was purified via flash chromatography on a silica column (2:98 v/v EtOAc:hexanes) to afford the title compound as a colorless oil (0.660 g, 1.88 mmol, 93.9% yield). $^1$H NMR (500 MHz, CDCl$_3$) δ 7.13 (dd, J=8.7, 6.2 Hz, 1H), 4.72 (s, 2H), 2.34 (d, J=2.6 Hz, 3H), 0.95 (s, 9H), 0.12 (s, 6H). $^{13}$C NMR (126 MHz, CDCl$_3$) δ 155.71 (dd, J=241.8, 2.9 Hz), 153.43 (dd, J=242.4, 2.7 Hz), 129.15 (dd, J=18.2, 7.2 Hz), 126.55 (d, J=20.5 Hz), 112.00 (dd, J=26.3, 5.6 Hz), 110.20 (dd, J=22.8, 5.5 Hz), 58.68 (d, J=5.3 Hz), 26.03, 18.53, 14.81 (dd, J=4.1, 2.2 Hz), −5.26. $^{19}$F NMR (471 MHz, CDCl$_3$) δ −110.43 (dd, J=16.3, 8.8 Hz), −124.14 (ddd, J=15.9, 6.1, 2.7 Hz).

10-(3,6-Difluoro-4-(hydroxymethyl)-2-methylphenyl)-7-hydroxy-5,5-dimethyldibenzo[b,e]silin-3 (5H)-one (42)

A flame-dried round-bottom flask was charged with 47 (0.349 g, 1.0 mmol, 10 eq.) and anhydrous THF (5 mL). The reaction was cooled to −78° C. and then treated dropwise with 1.7 M t-butyllithium in pentane (0.59 mL, 1.0 mmol, 10 eq.) over 1 minute. After stirring for an additional 8 minutes at −78° C., the reaction was treated dropwise with a solution of 6 (0.050 g, 0.10 mmol, 1.0 eq.) in anhydrous THF (2 mL) over 1 minute. After addition, the reaction was warmed to room temperature and stirred for 2 hours. The reaction was treated with 1.0 M HCl in H$_2$O (3 mL, 3 mmol, 30 eq.) and heated to 50° C. After stirring for 4 hours, the reaction was cooled to room temperature and quenched with brine. The organics were collected, dried over Na$_2$SO$_4$, and concentrated. The crude material was purified via flash chromatography on a silica column (5:95 to 10:90 v/v iPrOH:CH$_2$Cl$_2$ gradient). The crude residue was suspended in CH$_2$Cl$_2$ and collected by filtration to afford the title compound as a red solid (0.0321 g, 0.0782 mmol, 78.2% yield). $^1$H NMR (500 MHz, DMSO-d$_6$) δ 10.58 (s, 1H), 7.29 (dd, J=9.2, 5.6 Hz, 1H), 7.04 (s, 2H), 6.81 (d, J=9.4 Hz, 2H), 6.49 (s, 2H), 5.51 (s, 1H), 4.65 (s, 2H), 1.91 (d, J=2.2 Hz, 3H), 0.47 (s, 3H), 0.45 (s, 3H). $^{13}$C NMR (126 MHz, DMSO-d$_6$) δ 154.67 (d, J=237.9 Hz), 153.80 (d, J=241.6 Hz), 147.20, 131.25 (dd, J=18.4, 7.7 Hz), 128.97, 125.98 (dd, J=20.0, 4.4 Hz), 124.40 (dd, J=19.5, 3.1 Hz), 112.38 (dd, J=25.6, 5.4 Hz), 56.59 (d, J=4.1 Hz), 11.54 (d, J=2.2 Hz), −1.26, −1.84. $^{19}$F NMR (471 MHz, DMSO-d$_6$) δ −119.71 (dd, J=18.1, 9.3 Hz), −126.85 (dd, J=18.1, 5.3 Hz). HRMS (ESI$^+$): m/z calculated for [M+H]$^+$=411.1223; found=411.1216.

2,5-Difluoro-4-(7-hydroxy-5,5-dimethyl-3-oxo-3,5-dihydrodibenzo[b, e]silin-0-yl)-3-methylbenzaldehyde (Probe 8)

A round-bottom flask was charged with 48 (0.0174 g, 0.042 mmol, 1.0 eq.), 2-iodoxybenzoic acid (0.016 g, 0.051 mmol, 1.2 eq.), and DMSO (1 mL). After stirring 4 hours at room temperature, the reaction was concentrated. The crude material was purified via flash chromatography on a silica column (5:95 v/v iPrOH:CH$_2$Cl$_2$) to afford the title compound as a red solid (0.0067 g, 0.0164 mmol, 38.7% yield). $^1$H NMR (500 MHz, DMSO-d$_6$) δ 10.62 (s, 1H), 10.29 (d, J=2.4 Hz, 1H), 7.66 (dd, J=8.2, 5.1 Hz, 1H), 7.24 (s, 1H), 6.88 (s, 2H), 6.77 (s, 2H), 6.20 (s, 1H), 2.00 (d, J=2.0 Hz, 3H), 0.48 (s, 3H), 0.46 (s, 3H). $^{19}$F NMR (471 MHz, DMSO-d$_6$) δ −118.07 (dd, J=18.3, 8.5 Hz), −127.14 (dd, J=18.5, 4.8 Hz). HRMS (ESI$^+$): m/z calculated for [M+H]$^+$=409.1066; found=409.1077.

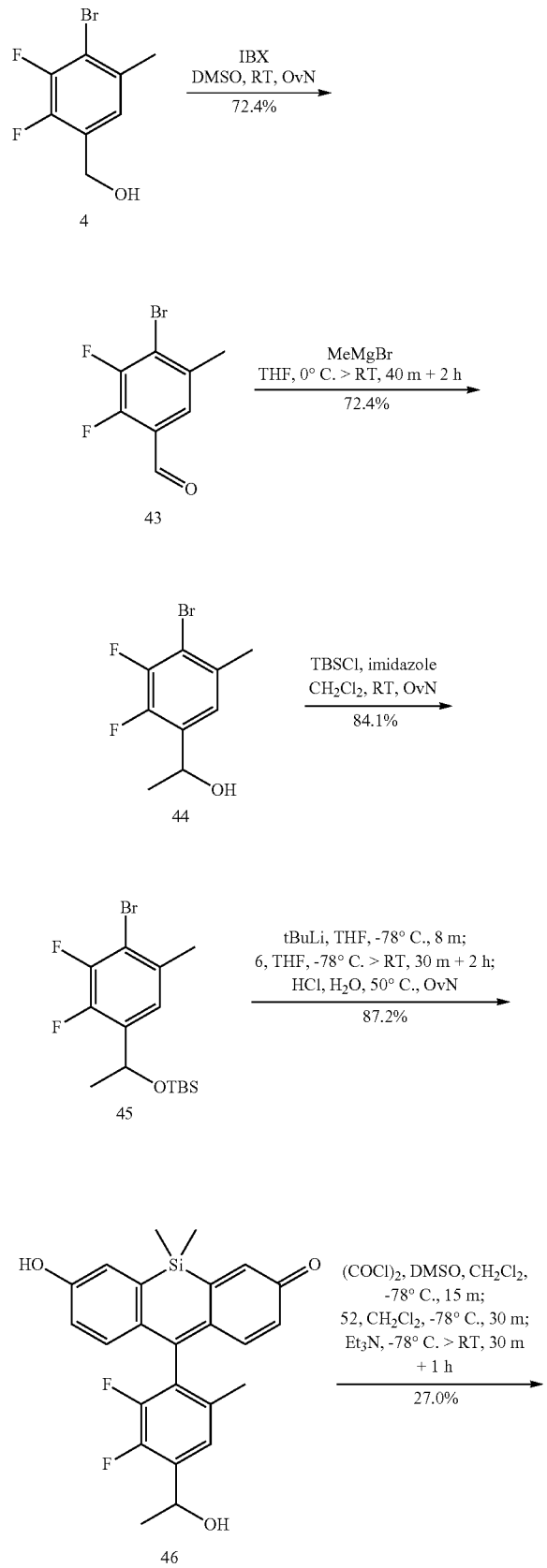

Scheme 14. Synthesis of Crrtl-red-AlDeSense.

-continued

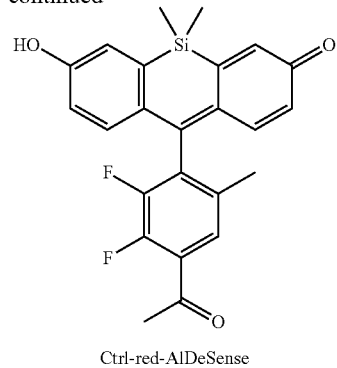

Ctrl-red-AlDeSense

4-Bromo-2,3-difluoro-5-methylbenzaldehyde (43)

A round-bottom flask was charged with 4 (0.460 g, 1.94 mmol, 1.0 eq.), 2-iodoxybenzoic acid (0.81 g, 2.9 mmol, 1.5 eq.), and DMSO (10 mL). After stirring overnight at room temperature, the reaction was poured into brine and diluted with $Et_2O$. The organics were collected, washed with $H_2O$, dried over $Na_2SO_4$, and concentrated under reduced pressure to afford the title compound as a light yellow solid (0.330 g, 1.40 mmol, 72.4% yield). $^1$H NMR (500 MHz, $CDCl_3$) δ 10.27 (s, 1H), 7.52 (d, J=6.3 Hz, 1H), 2.43 (s, 3H). $^{13}$C NMR (126 MHz, $CDCl_3$) δ 185.50 (dd, J=6.0, 3.1 Hz), 150.71 (dd, J=261.8, 14.7 Hz), 148.15 (dd, J=249.7, 13.5 Hz), 135.79 (d, J=4.3 Hz), 123.82 (d, J=5.8 Hz), 123.17 (d, J=3.7 Hz), 120.31 (d, J=17.1 Hz), 22.27 (d, J=2.3 Hz). $^{19}$F NMR (471 MHz, $CDCl_3$) δ −126.06 (d, J=21.8 Hz), −147.66 (dd, J=21.6, 6.2 Hz).

1-(4-Bromo-2,3-difluoro-5-methylphenyl)ethan-1-ol (44)

A flame-dried round-bottom flask was charged with 49 (0.388 g, 1.65 mmol, 1.0 eq.) and anhydrous THF (5 mL). The reaction was cooled to 0° C. and then treated dropwise with 3.0 M methylmagnesium bromide in $Et_2O$ (0.66 mL, 1.98 mmol, 1.2 eq.) over 1 minute. After stirring for an additional 40 minutes at 0° C., the reaction was warmed to room temperature and stirred for 2 hours. The reaction was quenched with brine and diluted with $Et_2O$ and $CH_2Cl_2$. The organics were collected, dried over $Na_2SO_4$, and concentrated. The crude material was dissolved in $CH_2Cl_2$ and treated with imidazole (0.011 g, 0.165 mmol, 0.1 eq.) and tert-butyldimethylsilyl chloride (0.024 g, 0.165 mmol, 0.1 eq.). After stirring for 10 minutes, the reaction was quenched with MeOH and concentrated. The crude residue purified via flash chromatography on a silica column (10:90 v/v EtOAc: hexanes) to afford the title compound as a colorless oil (0.300 g, 1.19 mmol, 72.4% yield). $^1$H NMR (500 MHz, $CDCl_3$) δ 7.17 (dd, J=6.8, 2.0 Hz, 1H), 5.16 (q, J=6.5 Hz, 1H), 2.39 (s, 3H), 1.95 (s, 1H), 1.50 (d, J=6.4 Hz, 3H). $^{13}$C NMR (126 MHz, $CDCl_3$) δ 147.66 (dd, J=246.7, 14.6 Hz), 145.91 (dd, J=248.2, 14.4 Hz), 134.74 (d, J=4.2 Hz), 133.27 (d, J=10.4 Hz), 121.75 (t, J=3.4 Hz), 111.07 (d, J=17.2 Hz), 64.25 (d, J=2.4 Hz), 24.28, 22.35 (d, J=2.3 Hz). $^{19}$F NMR (471 MHz, $CDCl_3$) δ −128.62 (dd, J=21.9, 2.2 Hz), −144.99 (dd, J=22.3, 6.8 Hz).

(1-(4-Bromo-2,3-difluoro-5-methylphenyl)ethoxy) (tert-butyl)dimethylsilane (45)

A round-bottom flask was charged with 50 (0.300 g, 1.19 mmol, 1.0 eq.), imidazole (0.163 g, 2.4 mmol, 2.0 eq.), and $CH_2Cl_2$ (10 mL). Once a solution had formed, tert-butyldimethylsilyl chloride (0.358 g, 2.4 mmol, 2.0 eq.) was added. After stirring overnight at room temperature, the reaction was concentrated under reduced pressure. The crude material was purified via flash chromatography on a silica column (hexanes) to afford the title compound as a colorless oil (0.367 g, 1.00 mmol, 84.1% yield). $^1$H NMR (500 MHz, $CDCl_3$) δ 7.19 (ddd, J=6.7, 2.1, 0.9 Hz, 1H), 5.11 (q, J=6.3 Hz, 1H), 2.38 (s, 3H), 1.39 (d, J=6.3 Hz, 3H), 0.90 (s, 9H), 0.07 (s, 3H), −0.01 (s, 3H). $^{13}$C NMR (126 MHz, $CDCl_3$) δ 147.40 (dd, J=246.2, 14.8 Hz), 145.23 (dd, J=247.1, 14.3 Hz), 134.52 (d, J=11.0 Hz), 134.34 (d, J=4.1 Hz), 122.13 (t, J=3.4 Hz), 110.33 (d, J=17.3 Hz), 64.36 (t, J=2.5 Hz), 25.93, 22.42 (d, J=2.3 Hz), 18.35, −4.81, −4.87. $^{19}$F NMR (471 MHz, $CDCl_3$) δ −129.38 (d, J=22.2 Hz), −145.34 (dd, J=22.4, 6.9 Hz).

10-(3,6-Difluoro-4-(1-hydroxyethyl)-2-methylphenyl)-7-hydroxy-5,5-dimethyldibenzo[b,e]silin-3 (5H)-one (46)

A flame-dried round-bottom flask was charged with 51 (0.357 g, 1.0 mmol, 5 eq.) and anhydrous THF (10 mL). The reaction was cooled to −78° C. and then treated dropwise with 1.7 M t-butyllithium in pentane (0.59 mL, 1.0 mmol, 5 eq.) over 1 minutes. After stirring for an additional 8 minutes at −78° C., the reaction was treated dropwise with a solution of 6 (0.100 g, 0.20 mmol, 1.0 eq.) in anhydrous THF (5 mL) over 3 minutes. After stirring for 30 minutes, the reaction was warmed to room temperature and stirred for 2 hours. The reaction was treated with 1.0 M HCl in $H_2O$ (6 mL, 6 mmol, 60 eq.) and heated to 50° C. After stirring overnight, the reaction was cooled to room temperature, quenched with brine, and diluted with $Et_2O$. The organics were collected, dried over $Na_2SO_4$, and concentrated. The crude material was purified via flash chromatography on a silica column (5:95 v/v MeOH:$CH_2Cl_2$). The crude material was further purified via flash chromatography on a silica column (0:100 to 10:90 v/v MeOH:$Et_2O$ gradient) to afford the title compound as a red solid (0.074 g, 0.174 mmol, 87.2% yield). $^1$H NMR (500 MHz, Methanol-$d_4$) δ 7.44-7.30 (m, 1H), 7.04 (d, J=2.5 Hz, 2H), 6.95 (dd, J=9.5, 0.9 Hz, 1H), 6.93 (dd, J=9.4, 0.9 Hz, 1H), 6.51 (dd, J=9.4, 2.4 Hz, 1H), 6.48 (dd, J=9.4, 2.4 Hz, 1H), 5.21 (q, J=6.5 Hz, 1H), 2.04 (s, 3H), 1.55 (d, J=6.5 Hz, 3H), 0.52 (s, 3H), 0.49 (s, 3H). $^{13}$C NMR (126 MHz, Methanol-$d_4$) δ 152.40, 146.43, 139.50, 136.99 (d, J=10.6 Hz), 134.10, 130.63, 130.27, 128.30 (d, J=14.2 Hz), 126.12, 123.77, 123.39, 64.42, 24.45, 18.93 (d, J=2.0 Hz), −1.39, −1.67. $^{19}$F NMR (471 MHz, Methanol-$d_4$) δ −142.00 (d, J=21.8 Hz), −150.09 (dd, J=21.7, 6.3 Hz). HRMS (ESI$^+$): m/z calculated for [M+H]$^+$=425.1379; found=425.1376.

10-(4-Acetyl-3,6-difluoro-2-methylphenyl)-7-hydroxy-5,5-dimethyldibenzo[b, e]silin-3(5H)-one (Ctrl-red-AlDeSense)

A flame-dried round-bottom flask was charged with anhydrous $CH_2Cl_2$ (1 mL) and oxalyl chloride (0.10 mL, 1.2 mmol, 20 eq.). The reaction was cooled to −78° C. and then treated dropwise with a solution of DMSO (0.17 mL, 2.4 mmol, 40 eq.) in anhydrous $CH_2Cl_2$ (1 mL) over 2 minutes. After stirring for an additional 15 minutes at −78° C., the reaction was treated dropwise with a solution of 121 (0.026 g, 0.061 mmol, 1.0 eq.) in anhydrous $CH_2Cl_2$ (2.5 mL) over 5 minutes. After stirring for 30 minutes, the reaction was treated dropwise with $Et_3N$ (0.34 mL, 2.4 mmol, 40 eq.) over 1 minute. After stirring for 30 minutes, the reaction was warmed to room temperature and stirred for 1 hour. The reaction poured into a dilute HCl solution and diluted with $CH_2Cl_2$. The organics were collected, dried over $Na_2SO_4$, and concentrated. The crude material was purified via flash chromatography on a silica column (5:95 v/v iPrOH: $CH_2Cl_2$). The crude material was further purified via flash chromatography on a silica column (0:100 to 100:0 v/v $Et_2O:CH_2Cl_2$ gradient) to afford the title compound as a red solid (0.0070 g, 0.0166 mmol, 27.0% yield). $^1$H NMR (500 MHz, $CDCl_3$) δ 7.63 (d, J=6.0 Hz, 1H), 7.03 (d, J=2.5 Hz, 2H), 6.83 (d, J=9.5 Hz, 2H), 6.53 (dd, J=9.5, 2.5 Hz, 2H), 2.73 (d, J=4.5 Hz, 3H), 2.07 (s, 3H), 0.48 (s, 3H), 0.46 (s, 3H). $^{13}$C NMR (126 MHz, $CDCl_3$) δ 194.56, 151.65, 147.13, 144.22, 137.17, 135.91, 133.69 (dd, J=8.9, 5.4 Hz), 130.07, 128.39, 126.80 (d, J=9.9 Hz), 125.66, 123.12, 31.65 (d, J=6.8 Hz), 18.98, −1.22, −1.40. $^{19}$F NMR (471 MHz, $CDCl_3$) δ −136.39 (d, J=23.0 Hz), −137.81 (dq, J=21.6, 5.2 Hz). HRMS (ESI$^+$): m/z calculated for $[M+H]^+$=423.1223; found=423.1229.

Example 3. Experimental Details

ALDH Isoform Activity Assays.

The activity of each isoform of ALDH was confirmed by monitoring the production of NADH at 340 nm when incubated with the most commonly used substrate for that enzyme (propionaldehyde for ALDH1A1, ALDH1A2, ALDH1A3, ALDH2 and ALDH4A1; benzaldehyde for ALDH3A1, and succinic semialdehyde for ALDH5A1). Each isoform was diluted with 50 mM triethanolamine (TEA, pH 7.4) to a final concentration of 1 μM and placed in a 1 mL quartz cuvette. Directly before measurement, NAD$^+$ was added to final concentration of 2.5 mM and the preferred substrate was added to a final concentration of 1 mM. Absorbance spectra were taken from 300 to 500 nm every half minute for 15 minutes. Units of activity for each enzyme were calculated from the slope of absorbance increase at 340 nm over time, (1 unit=1 μmol substrate turned over/μmol enzyme/min).

AlDeSense Isoform Selectivity Assay.

Activation of AlDeSense was assessed using 20 units of each ALDH isoform. Activity was determined by activity measurements using each isoform's preferred substrate (1 unit=1 μmol substrate turned over/mol enzyme/min). Further details are in the supplementary information. All enzymatic reactions were performed in 50 mM triethanolamine buffer (pH 7.4, Thermo Fisher) with 2.5 mM NAD+(Alfa Aesar) and 5% v/v DMSO (Thermo Fisher) in a 1 mL quartz cuvette at room temperature.

AlDeSense activation was determined using fluorescence. Immediately before measurement, AlDeSense (1 μM) was added to a quartz cuvette. After vigorous mixing, the reaction was monitored at room temperature for 15 min. Fluorescence spectra were acquired according to following parameters: λex=498 nm, and emission range=505-580 nm. All scans were normalized to the signal from AlDeSense in 50 mM TEA and 2.5 mM NAD+(without enzyme). Endpoint measurements at 15 min were performed in triplicate and reported as the averages±standard deviation.

Inhibition of ALDH1A1.

ALDH1A1 (100 nM) in 50 mM TEA (pH 7.4) was incubated with 2.5 mM NAD+. Immediately before measurement, 4-diethylaminobenzaldehyde (DEAB) in 95% ethanol was added for a final concentration of 100 nM. The reaction was initiated with the addition of AlDeSense (1 μM). The solution was mixed with vigorous pipetting and fluorescence spectra were acquired. Fluorescence spectra were acquired according to following parameters: λex=498 nm, and emission range=505-580 nm. Scans were taken periodically for up to 30 min. The reaction proceeded at room temperature throughout the experiment. All scans were normalized to the peak of AlDeSense in 50 mM TEA and 2.5 mM NAD+ without the addition of enzyme.

siRNA Knockdown of ALDH1A1

K562 cells were grown to ~70% confluency in a poly-L-lysine (Trevigen) coated Nunc™ Lab-Tek™ 8-well Chamber Slide™ system (Thermo Scientific) 1 day before treatment with siRNA. Both the negative control scrambled siRNA (Sigma-Aldrich, MISSION® siRNA Universal Negative Control #1) as well as the ALDH1A1 siRNA (Sigma-Aldrich, SASI_Hs01_00244056) was applied at 50 μM concentrations following the Lipofectamine 3000 (Thermo Fisher) protocol for a 24-well plate. 0.75 μL of the Lipofectamine 3000 reagent was used per sample. After treatment, cells incubated with the siRNA in Opti-MEM (Gibco) at 37° C., 5% $CO_2$ for 8 hours. At this point, the Opti-MEM was removed and replaced with full growth media (IMDM supplemented with 10% FBS). Cells were incubated further at 37° C., 5% CO2 for 48 hours before imaging on the Zeiss LSM 700 confocal. To stain the cells with each imaging reagent, 1 μL of 2 mM AlDeSense AM in DMSO was used per 1 mL of serum-free media (DMEM/F12 supplemented with 15 μM HEPES). Growth media was removed from the cells and replaced with the premixed dye solution. Cell staining continued for 30 minutes at room temperature (25° C.), after which the cells were immediately imaged. The optical configuration was optimized for the scrambled siRNA samples and the same optical settings were used for all images.

Mammosphere Culture and Imaging.

Mammosphere formation from MDA-MB-231 breast cancer cells was performed as described previously with some modifications. Cells were resuspended and diluted to a density of 2000 cells/mL in DMEM/F12 (Sigma-Aldrich) supplemented with 2% B27 supplement (Thermo Fisher), 40 ng/mL rhFGF-2 (Miltenyi Biotec), and 20 ng/mL rhEGF (Gibco®). They were plated in ultra-low attachment 6-well plates (Corning) and incubated at 37° C. and 5% CO2 for 5 days or until most mammospheres were between 60-100 nm. At this point, the mammospheres were transferred to a 4-well chamber slide coated with Poly-L-lysine as described previously. The mammospheres were then either immediately imaged with AlDeSense or Ctrl-AlDeSense, or the media was exchanged with full DMEM media supplement with 10% FBS and non-essential amino acids to allow differentiation over 36 hours.

At various time points, the mammospheres were stained with 2 μM AlDeSense or Ctrl-AlDeSense as described above. Staining continued for 1 h at room temperature before imaging with a wide field fluorescence microscope (Zeiss Axiovert 200M). A GFP filter set was used to excite the fluorophores. Exposure times were set equally for all images taken within a data set and configured to give low signal in Ctrl-AlDeSense stained tumorspheres. Only mammospheres greater than 50 μm in diameter were considered in the analysis.

B16F0 Melanoma Confocal Imaging. B16F0 murine melanoma cells were cultured for 5 days on polyacrylamide hydrogels with or without spiral patterns as described previously (Drug Discov Today 2014, 19, 1953). The coverslips on which the hydrogels and cells were mounted were transferred to a glass-bottomed dish for confocal imaging, leaving the cells intact. Solutions of either 2 μM AlDeSense AM or 2 μM Ctrl-AlDeSense AM in PBS were added to the two types of cells. The cells were incubated at room temperature for 1 h and then immediately imaged. Confocal imaging was performed on a Zeiss LSM700 Confocal Microscope, utilizing the 488 nm laser line to excite AlDeSense AM and the 20×/0.8 objective. Three different coverslips of cells were imaged for each set of conditions and at least 6 μmages were taken for each coverslip. Using ImageJ, ROIs were drawn around areas covered with cells and mean fluorescence values were measured for each image.

Ex Vivo Lung Metastases Imaging.

Six to eight-week-old female $C_{57}BL/6J$ mice were purchased from Jackson Laboratory. Experimental metastases were established by injecting $2 \times 10^5$ melanoma cells via lateral tail vein injection. Mice were euthanized at either 7- or 11-days post injection. Immediately after euthanization, their lungs were excised and perfused with about 1 mL of either 15 μM AlDeSense AM or 15 μM Ctrl-AlDeSense AM in PBS. Outer portions of the lungs were rinsed in 15 mL of PBS to remove blood or excess dyes. After 2 hours incubation at room temperature (25° C.), the lungs were imaged on the IVIS spectrum imaging system (Perkin Elmer). Data was processed using Living Image software (Version 4.1).

In Vivo Melanoma Tumor Fluorescence Imaging.

All in vivo imaging experiments were performed with the approval of the Institutional Animal Care and Use Committee of the University of Illinois at Urbana-Champaign. Six to eight-week-old female BALB/c mice were purchased from the Jackson Laboratory for the tumor imaging experiment. Primary localized tumors were established by subcutaneously injecting B16F0 cells ($5 \times 10^5$ cells in 100 μL of Hanks' balanced salt solution per injection). For each animal, cells that were grown on patterned gels were injected on the right lateral flank and cells grown on non-patterned gels were injected on the left lateral flank. At 1 and 2 weeks, mice were intravenously injected with either 15 μM AlDeSense or Ctrl-AlDeSense. After 24 h, the mice were imaged using an IVIS spectrum imaging system for epifluorescence in conjunction with a CT scan. Data was processed using Living Image software (Version 4.1).

Photostability Assay.

2 μM AlDeSense, Ctrl-AlDeSense, and AldeFluor were placed in triplicate in a 96-well plate. The plate was placed in an IVIS Spectrum imaging system and irradiated repeatedly using the FITC excitation filter for 30 minutes. Fluorescence of each sample was measured at various time points and normalized to the level of fluorescence emitted by each sample at time 0.

Expression and Purification of ALDH1A1 and Related Isoforms.

Expression constructs for recombinant human ALDH1A1, ALDH1A2, ALDH1A3, ALDH2, ALDH3A1, ALDH4A1, and ALDH5A1 were generously provided by Prof. Daria Mochly-Rosen (Stanford, Chemical and Systems Biology). E. coli BL21(DE3) cells were transformed with each of the above constructs. Colonies were selected from an agar plate containing 100 μg/mL ampicillin and grown overnight (37° C., 220 rpm) with 100 μg/mL ampicillin. The overnight culture (10 mL) was inoculated into 1000 mL LB supplemented with 100 μg/mL ampicillin. At O.D.~0.5, IPTG was added to a final concentration of 1 mM and incubated overnight (30° C., 200 rpm, 18 h or 25° C., 200 rpm, 24 h). The cells were then harvested by centrifugation (4° C., 4,000 rpm, 90 min) and cell pellets stored at −80° C. until purification.

The bacterial pellets were resuspended in BugBuster® Master Mix (EMD Millipore, 15 mL for every 500 mL of cell culture collected) combined with protease inhibitor cocktail (1 tablet for every liter of cells collected, Pierce™ Protease Inhibitor Tablets, EDTA-free). They were then lysed according to manufacturer instructions (30 min incubation, room temp, rocking). The extract was centrifuged (4° C., 4,000 rpm, 90 min) and the supernatant was filtered (0.22 m syringe filter, EMD Millipore) and applied to a Ni-NTA column. The column was washed by the following binding buffer: 20 mM sodium phosphate pH 7.4, 0.5 M NaCl, 20 mM imidazole. Washing continued for 10 column volumes or until absorbance measurements at 280 nm were sufficiently low to ensure the removal of non-specific binders. Target proteins were then eluted by wash buffer (20 mM sodium phosphate pH 7.4, 0.5 M NaCl, 500 mM imidazole). Purity of eluted protein was determined to be ≥95% by SDS-PAGE and concentration of protein was determined by bicinchoninic acid (BCA) assay. Protein was stored with 50% glycerol at −80° C.

BAAA Isoform Selectivity Assay.

BAAA activation was determined using UV/Vis spectroscopy. A 2 mM stock solution of BAAA was prepared in DMSO and activated with 2M HCL as described in the ALDEFLUOR™ Kit protocol (STEMCELL Technologies Inc.). Immediately before measurement, BAAA was added to the reaction mixture described above to a final concentration of 18 μM. The solution was mixed vigorously, and the reaction proceeded at room temperature. UV/Vis absorbance spectra were taken from 300 to 500 nm every 30 seconds for 15 minutes. The rate of NADH produced per minute was calculated according to the absorbance at 340 nm ($\varepsilon = 6{,}220\ M^{1}\ cm^{-1}$). All measurements were performed in triplicate and reported as the average±standard deviation. 20 units of enzyme and 18 μM of BAAA were necessary to detect a significant increase in absorbance at 340 nm for the ALDH1A1 isoform.

Cell Culture.

K562 cells were obtained from Prof. Paul Hergenrother (UIUC, Chemistry). K562 cells were cultured as a suspension in Iscove's Modified Dulbecco's Medium (IMDM, ATCC) supplemented with 10% fetal bovine serum (FBS, Sigma Aldrich) and 1% penicillin/streptomycin (Corning). MDA-MB-231 cells were purchased from the American Type Culture Collection (ATCC) and cultured in Dulbecco's Modified Eagle Medium (DMEM, ATCC) supplemented with 10% FBS, 1% pen-strep, and non-essential amino acids. B16F0 cells were obtained from the ATCC and cultured in Dulbecco's Modified Eagle Medium (DMEM, ATCC) supplemented with 10% fetal bovine serum (FBS, Sigma Aldrich) and 1% penicillin/streptomycin (Corning). All cells were grown at 37° C. in a humidified incubator with 5% CO2 unless otherwise noted. For every cell line, media was changed, or cells were passaged every three days.

Trypan Blue Cytotoxicity Assay.

K562 cells were plated in a 96-well plate at a density of 500,000 cells/mL in full IMDM media supplemented with either 1 μM or 5 M AlDeSense AM. Equivalent samples were supplemented with 1 μM or 5 M DMSO as a vehicle control. At 6, 12, and 24 hours, a 10 μL sample was removed from each of the samples and mixed 1:1 with a 0.4% wt/volume trypan blue solution in PBS. Samples were incubated for 1 minute at room temperature before being loaded onto a hemocytometer where live and dead cells were counted. Each sample was made in triplicate for each time point.

Analysis of AlDeSense AM De-Esterification.

To analyze the de-esterification of AlDeSense AM in cells, ~20 million K562 cells (grown in suspension using full IMDM media as described previously) were collected by centrifugation and resuspended in a 10 μM solution of AlDeSense AM in PBS. The cells were incubated at room temperature with rocking for 15 min, then collected by centrifugation and washed with PBS. The cells were then resuspended by gentle pipetting into 5 mL of ice cold digitonin lysis buffer: 150 mM NaCl, 50 mM HEPES pH 7.4, and 25 ug/mL digitonin (Sigma Aldrich). The cells were incubated on ice for 10 minutes and then centrifuged at 2000 RCF to pellet cell debris. The supernatant was collected as crude cytosolic lysate. Cell lysate was measured by mass spectrometry using a Thermo Scientific Orbitrap mass spectrometer (San Jose, Calif., USA). Lysate samples were diluted 1:1000 in 50:25:25 methanol:acetonitrile:water with 0.1% formic acid and subsequently analyzed by chemical ionization in the positive mode.

Standard Flow Cytometry Experiment with K562 Cells.

K562 cells were resuspended in PBS to a final concentration of 100,000 cells/mL. The suspension was divided into 0.5 mL aliquots and the cells were collected by centrifugation at 1000 rpm for 5 min at 4° C. Each sample was then resuspended in premixed AlDeSense AM or Ctrl-AlDeSense AM solutions (1.5 μM, PBS). For each dye, triplicate samples were prepared. Cells were incubated with dye for 30 minutes at room temperature with rocking to prevent cell clumping and ensure even dye distribution. At the end of the incubation period, cells were again collected by centrifugation at 1000 rpm for 5 min at 4° C. The dye solution was removed by aspiration, and each sample of cells were resuspended in 0.5 mL of PBS. The samples were immediately placed on ice until analysis. The samples were analyzed by a BD LSR II Flow Cytometry Analyzer using a 488 nm laser and a FITC filter. Data analyzed on FCS Express 6.04.

Flow Cytometry Analysis of K562 Cells Grown Under Hypoxia.

Using a hypoxic incubator, K562 cells were grown in full IMDM media at 1% $O_2$, 5% $CO_2$, and 94% $N_2$ for 48 hours. As a control, cells from the same passage were also grown in a standard cell culture incubator only supplied with 5% $CO_2$. At the end of the 48-hour period, the cells were collected by centrifugation and resuspended in either 1 μM AlDeSense AM or 1 μM Ctrl-AlDeSense AM (both in PBS) at a density of 1 million cells/mL. Cells were incubated in dye for 30 min at room temperature with rocking. At the end of the incubation period, the cells were spun down and resuspended as 100 uL samples in PBS. CD34-VioBlue® and CD38– APC (Miltenyi Biotec) were added at 1:11 of the stock concentration and incubated for 10 minutes on ice, protected from light. At the end of this period, the cells were washed, resuspended in PBS, and kept on ice until analysis by flow cytometry. The samples were analyzed by a BD LSR II Flow Cytometry Analyzer using a 488 nm laser with a 530/30 bandpass filter for AlDeSense, a 403 nm laser with a 450/50 band pass filter for CD34-VioBlue®, and a 640 nm laser with a 660/20 bandpass filter for CD38– APC. Data analyzed on FCS Express 6.04.

Confocal Imaging of K562 Cells.

The day before imaging, Nunc™ Lab-Tek™ Chamber Slide™ systems (Thermo Fisher) were coated with poly-L-lysine (Trevigen) according to manufacturer's instructions. Cells were added to the chamber slides at a concentration of 400,000 cells/mL, yielding 90% confluent cells after 24 h. To stain the cells with each imaging reagent (AlDeSense AM or Ctrl-AlDeSense AM), 1 μL of 2 mM dye in DMSO was used per 1 mL of serum-free media (DMEM/F12 supplemented with 15 μM HEPES). Growth media was removed from the cells and replaced with the premixed dye solution. Cells were incubated with dye for 30 minutes at room temperature (25° C.), after which time the cells were immediately imaged. Live cell imaging was performed on a Zeiss LSM700 Confocal Microscope, utilizing the 488 nm laser and light filter settings for FITC dye. For each condition, three different wells of cells were imaged by taking at least three images each using the 20x/0.8 objective. The optical configuration was optimized by minimizing signal in samples stained with Ctrl-AlDeSense AM or in inhibited samples by adjusting gain. The same optical settings were used for images within each set of matched experiments. Images were analyzed using ImageJ software (Version 1.5 in).

To inhibit ALDH1A1 before imaging, cells were pre-incubated with 10 μM disulfiram in PBS for 60 min at 37° C. in an incubator with 5% $CO_2$. Vehicle controls with PBS supplemented with DMSO were subjected to preincubation conditions alongside the inhibited samples. At the end of the preincubation period, cells were stained with AlDeSense AM as described above.

Subcellular Localization of AlDeSense and BAAA.

To determine the subcellular localization of AlDeSense, K562 cells were plated and stained as described above with either 2 μM AlDeSense AM or 2 μM BAAA. BAAA was activated with 2M HCL as described in the ALDEFLUOR™ Kit protocol (STEMCELL Technologies Inc.). After 30 minutes of staining, about 5 μL of 100x solutions of rhodamine 101 methyl ester (for mitochondrial staining), LysoTracker Red, or ER Tracker Red were added and allowed to stain for about 5 minutes before immediately imaging on a Zeiss LSM700 Confocal Microscope, utilizing the 488 nm laser for AlDeSense or BAAA signal and the 555 nm laser for each of the trackers. Pearson's R coefficients were calculated for 13 μmages using the Coloc 2 function of Fiji, a distribution of Image J optimized for biological image analysis.

Western Blot of siRNA Knockdown.

K562 cell lysate's concentration was measured with an Epoch Microplate Spectrophotometer (Bioteck). Lysate was diluted to desired concentration and mixed with 2x Laemmli Sample Buffer (Bio-Rad) and heated at 95° C. for 5 minutes. Samples were run on a 12% gel (12% Mini-PROTEAN TGX precast gel, Bio-Rad) and transferred to PVDF membrane (Mini format 0.2 um PVDF Trans-Blot Turbo™ Transfer pack, Bio-Rad) using a Trans-Blot Turbo™ Transfer System (Bio-Rad). The membrane was blocked in 5% bovine serum albumin (5% BSA) in TBS for one hour at room temperature. Then, the membrane was incubated in primary antibody (1:1000 in 5% BSA) (ALDH1A1 (B-5), sc-374149, lot #E1316, Santa Cruz Biotechnology) overnight at 4° C. The membrane was then washed three times for 5 minutes with TBS, then it was incubated in secondary antibody (1:500 in TBS) (m-IgGκBP-CFL 680, sc-516180, lot #A0917, Santa Cruz Biotechnology) for 90 minutes. The membrane was washed twice with TBS for 5 minutes. The membrane was visualized with ChemiDoc™ XRS+ System (Bio-Rad).

Antibody Colocalization.

CD34-VioBlue®, CD38– APC, and CD133/1 (AC133)-PE were purchased from Miltenyi Biotec (Auburn, Calif., USA). K562 cells were grown on Poly-L-Lysine coated coverslips within 24-well dishes overnight at 37° C., 5% CO2. The following day, the cells were treated with the antibodies at 1:25 concentration for 1 hour at room temperature. Following this, AlDeSense AM was added at a final concentration of 1 µM and the cells were further incubated for 30 minutes at room temperature. Once this was complete, the coverslips were removed and mounted onto glass slides for confocal imaging.

Live cell imaging was performed on a Zeiss LSM700 Confocal Microscope, utilizing the 488 nm laser to excite AlDeSense AM, the 405 nm laser to excite CD34-VioBlue®, the 639 nm laser to excite CD38- APC, and the 555 nm laser to excite CD133/1(AC133)-PE. Images were taken using the 63×/1.4 Oil objective. Pearson's R coefficients were calculated for 13 µmages using the using the Coloc 2 function of Fiji.

Flow Cytometry Analysis of e-CSC Versus non-CSC Populations of B16F0 Melanoma Cells.

B16F0 melanoma cells were grown on patterned or non-patterned hydrogels as described previously (*Nat Mater* 2016, 15, 856). Cells were trypsinized and resuspended at about 2 million cells/mL in PBS and kept on ice. Samples of cells were then spun down and resuspended in either 1 µM AlDeSense AM or 1 µM Ctrl-AlDeSense AM, maintaining the same cell density. The samples were then incubated with the dyes at room temperature for 30 minutes with rocking. Samples of unstained patterned and nonpatterned cells were also reserved on ice as a negative control. At the end of the 30-minute dye incubation period, the cells were pelleted by centrifugation and resuspended in 100 µL of PBS buffer. The cells were then stained with CD271 (LNGFR)-APC, human and mouse (clone: REA648, Miltenyi Biotec). To achieve a 1:11 dilution, 10 µL of antibody was added to each 100 µL sample. The cells were incubated with antibody for 10 minutes at 4° C. in the dark. Controls stained only with AlDeSense or Ctrl-AlDeSense were produced by incubating in PBS without antibody. At the end of the incubation period, all samples were spun down and resuspended in 500 µL of PBS and kept on ice until analysis. The samples were analyzed by a BD LSR II Flow Cytometry Analyzer using a 488 nm laser with a 530/30 bandpass filter for AlDeSense or Ctrl-AlDeSense and a 640 nm laser with a 660/20 bandpass filter for CD38- APC. Data analyzed on FCS Express 6.04.

Statistical Analyses.

Statistical analyses were performed in GraphPad Prism version 7.03. Sample sizes in all experiments were of sufficient size to detect at least a p value <0.05, which was considered to be significant. All data were analyzed using Student's t tests and were expressed as mean±SD, unless otherwise stated.

Example 4. Pharmaceutical Dosage Forms

The following formulations illustrate representative pharmaceutical dosage forms that may be used for the administration of a compound of a formula described herein, a compound specifically disclosed herein, or a pharmaceutically acceptable salt or solvate thereof (hereinafter referred to as 'Compound X'):

| (i) Tablet 1 | mg/tablet |
| --- | --- |
| 'Compound X' | 100.0 |
| Lactose | 77.5 |
| Povidone | 15.0 |

| (i) Tablet 1 | mg/tablet |
| --- | --- |
| Croscarmellose sodium | 12.0 |
| Microcrystalline cellulose | 92.5 |
| Magnesium stearate | 3.0 |
| | 300.0 |

| iii) Tablet 2 | mg/tablet |
| --- | --- |
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |
| (iii) Capsule | mg/capsule |
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |
| (iv) Injection 1 (1 mg/mL) | mg/mL |
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |
| (v) Injection 2 (10 mg/mL) | mg/mL |
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula II:

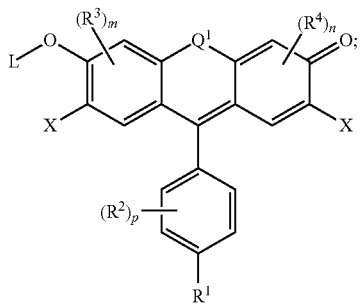

or a salt thereof, wherein
$Q^1$ is O, S, $C(R^A)_2$, $Si(R^A)_2$, or $P(=O)R^A$, wherein each $R^A$ is independently H, —$(C_1$-$C_6)$alkyl, or —$O(C_1$-$C_6)$alkyl;
L is H or an enzymatically labile group;
each X is independently H, halo, nitro, or alkylsulfonyl;
$R^1$ is —CH(=O), —C(=O)$(C_1$-$C_6)$alkyl, or —CH(OR)$_2$ wherein each R is independently H, —$(C_1$-$C_6)$alkyl, or two R taken together form an acetal;
$R^2$, $R^3$ and $R^4$ are each independently halo, OH, —$(C_1$-$C_6)$alkyl, —$O(C_1$-$C_6)$alkyl, nitro, or phenyl wherein —$(C_1$-$C_6)$alkyl and phenyl are optionally substituted with 1-5 substituents;
m and n are independently 0-2; and
p is 1-4.

2. The compound of claim 1 wherein L is the enzymatically labile group and the labile group comprises an ester moiety.

3. The compound of claim 2 wherein the labile group is —$C(R^C)_2OC(=O)$alkyl wherein each $R^C$ is independently H or —$(C_1$-$C_6)$alkyl.

4. The compound of claim 1 wherein $Q^1$ is O, and $R^2$ is —$(C_1$-$C_6)$alkyl.

5. A compound of Formula I:

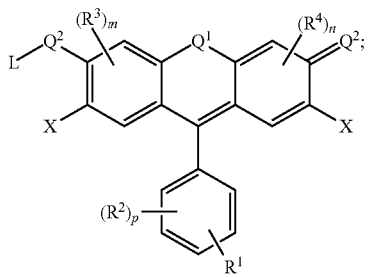

or a salt thereof,
wherein $Q^1$ is $Si(R^A)_2$;
each $Q^2$ is independently O, S or $NR^B$, wherein $R^B$ is H or —$(C_1$-$C_6)$alkyl;
L is H or an enzymatically labile group;
each X is independently H, halo, nitro, or alkylsulfonyl;
$R^1$ is —CH(=O), —C(=O)$(C_1$-$C_6)$alkyl, or —CH(OR)$_2$ wherein each R is independently H, —$(C_1$-$C_6)$alkyl, or two R taken together form an acetal;

$R^2$, $R^3$ and $R^4$ are each independently halo, OH, —$(C_1$-$C_6)$alkyl, —$O(C_1$-$C_6)$alkyl, nitro, or phenyl wherein —$(C_1$-$C_6)$alkyl and phenyl are optionally substituted with 1-5 substituents;
m and n are independently 0-2; and
p is 0-4.

6. The compound of claim 1 wherein X is halo and each $R^2$ is independently halo or —$(C_1$-$C_6)$alkyl.

7. The compound of claim 5 wherein X is H and each $R^2$ is independently halo or —$(C_1$-$C_6)$alkyl wherein at least one $R^2$ comprises halo.

8. The compound of claim 1 wherein $Q^1$ is O or $Si(R^A)_2$.

9. The compound of claim 8 wherein
each X is independently H or halo; and
each $R^2$ is independently halo or —$(C_1$-$C_6)$alkyl.

10. The compound of claim 1 wherein the compound of Formula II is a compound of Formula III:

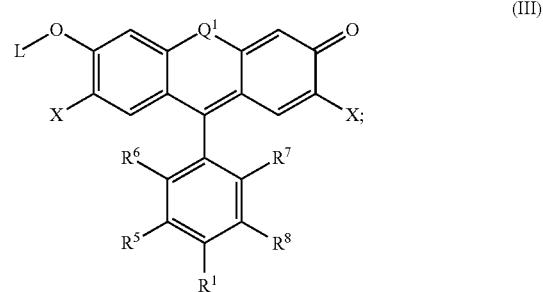

wherein
$Q^1$ is O or $Si(R^A)_2$;
L is H or —$CH_2OC(=O)$alkyl;
X is H or halo; and
$R^5$, $R^6$, $R^7$ and $R^8$ are each independently H, halo, OH, —$(C_1$-$C_6)$alkyl, —$O(C_1$-$C_6)$alkyl, or nitro wherein —$(C_1$-$C_6)$alkyl is optionally substituted with 1-5 substituents.

11. The compound of claim 10 wherein $R^7$ is —$(C_1$-$C_6)$alkyl or —$(C_2$-$C_6)$alkyl.

12. The compound of claim 10 wherein $R^5$, $R^6$ and $R^8$ are each independently H or halo.

13. The compound of claim 10 wherein $R^5$, $R^6$ and $R^8$ are H; and
L is H and $R^7$ is —$(C_1$-$C_6)$alkyl; or
$R^1$ is —CH(=O), —CH(OCH$_3$)$_2$, or —C(=O)CH$_3$; or
X is halo and $R^7$ is —$(C_1$-$C_6)$alkyl; or
X is fluoro, L is H and $R^7$ is —$(C_1$-$C_6)$alkyl.

14. The compound of claim 13 wherein X is fluoro and L is —$CH_2OC(=O)CH_3$.

15. The compound of claim 14 wherein $R^1$ is —CH(=O); or $R^1$ is —C(=O)CH$_3$.

16. The compound of claim 1 wherein the compound of Formula II is a compound of Formula IV:

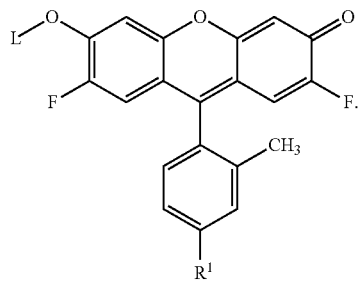
(IV)

17. The compound of claim 5 wherein the compound of Formula I is a compound of Formula V:

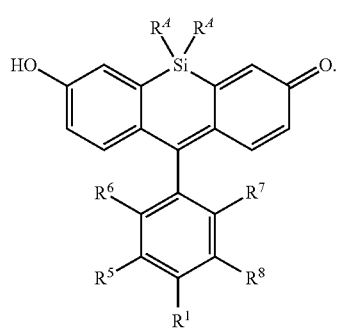
(V)

18. The compound of claim 17 wherein:

$R^A$ and $R^7$ are —($C_1$-$C_6$)alkyl;

$R^1$ is —CH(=O), —CH(OCH$_3$)$_2$, or —C(=O)CH$_3$; and $R^5$, $R^6$ and $R^8$ are each independently H or halo.

19. The compound of claim 18 wherein $R^5$ and $R^6$ are halo and $R^8$ is H.

20. The compound of claim 1 wherein the compound of Formula II is:

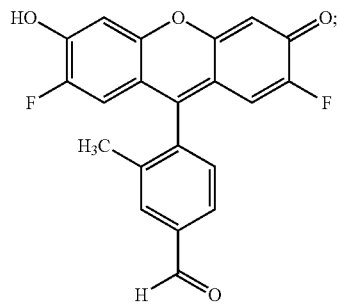
AlDeSense

-continued

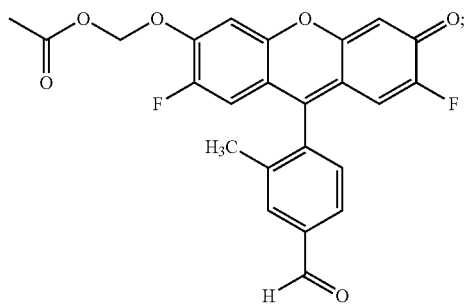
AlDeSense AM

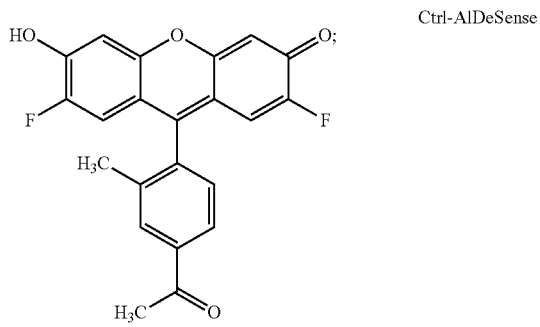
Ctrl-AlDeSense

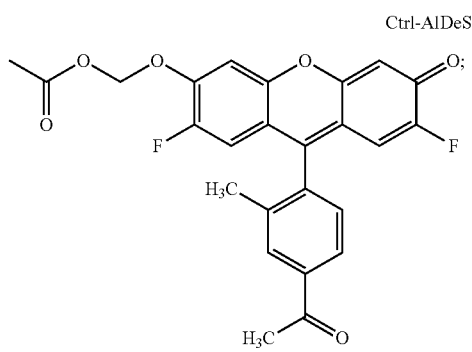
Ctrl-AlDeSense Am

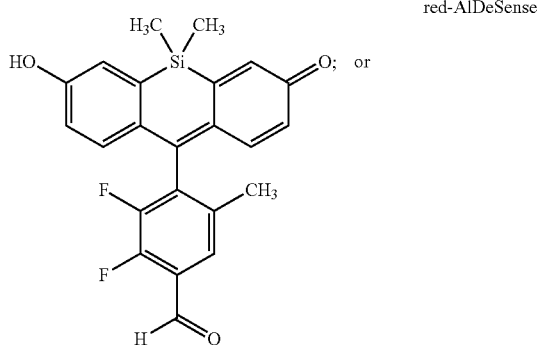
red-AlDeSense or

Ctrl-red-AlDeSense

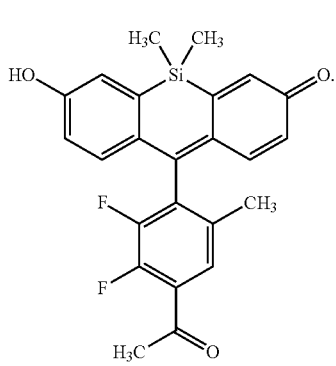

21. A method for imaging a cell comprising:
a) contacting a cell and a fluorescent probe of Formula II:

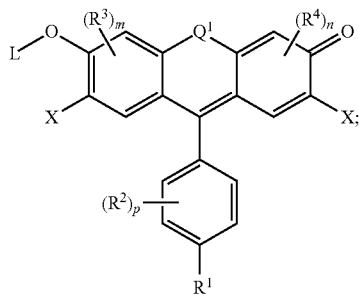

(II)

or a salt thereof, wherein
Q$^1$ is O, S, C(R$^A$)$_2$, Si(R$^A$)$_2$, or P(=O)R$^A$, wherein each R$^A$ is independently H, —(C$_1$-C$_6$)alkyl, or –O(C$_1$-C$_6$) alkyl;
L is H or an enzymatically labile group;
each X is independently H, halo, nitro, or alkylsulfonyl;
R$^1$ is —CH(=O), —C(=O)(C$_1$-C$_6$)alkyl, or —CH(OR)$_2$ wherein each R is independently H, —(C$_1$-C$_6$)alkyl, or two R taken together form an acetal;
R$^2$, R$^3$ and R$^4$ are each independently halo, OH, —(C$_1$-C$_6$)alkyl, —O(C$_1$-C$_6$)alkyl, nitro, or phenyl wherein —(C$_1$-C$_6$)alkyl and phenyl are optionally substituted with 1-5 substituents;
m and n are independently 0-2; and
p is 1-4; and
b) determining the fluorescent intensity in the contacted cell;
wherein aldehyde dehydrogenase-$_1$A$_1$ (ALDH$_1$A$_1$), when present in the contacted cell, oxidizes the aldehyde moiety R$^1$ is —CH(=O) of Formula I to a carboxyl moiety; and
wherein the fluorescent intensity of the contacted cell is modulated by the amount of ALDH$_1$A$_1$ present in the cell, thereby providing an image of aldehyde dehydrogenase activity in the contacted cell.

22. The method of claim 21 comprising contacting the cell and a control compound R$^1$ is —C(=O)(C$_1$-C$_6$)alkyl of Formula II and determining the difference in fluorescent intensity in the contacted cell relative to the control.

23. The method of claim 21 wherein an enzyme in the cell cleaves the enzymatically labile group L of Formula II to release a phenolic compound from the fluorescent probe, and ALDH$_1$A$_1$, when present in the contacted cell, oxidizes the aldehyde moiety R$^1$ is —CH(=O) of the phenolic compound to a carboxyl moiety.

* * * * *